(12) United States Patent
Finlay et al.

(10) Patent No.: US 9,458,133 B2
(45) Date of Patent: Oct. 4, 2016

(54) ISOQUINOLINES AS POTASSIUM ION CHANNEL INHIBITORS

(71) Applicant: BRISTOL-MYERS SQUIBB COMPANY, Princeton, NJ (US)

(72) Inventors: Heather Finlay, Skillman, NJ (US); Ashok Kumar Adisechan, Pondicherry (IN); Naveen Kumar Dhondi, Secunderabad (IN); Prashantha Gunaga, Bangalore (IN); John Lloyd, Yardley, PA (US); Srinivasu Pothukanuri, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/771,902

(22) PCT Filed: Mar. 10, 2014

(86) PCT No.: PCT/US2014/022264
§ 371 (c)(1),
(2) Date: Sep. 1, 2015

(87) PCT Pub. No.: WO2014/143609
PCT Pub. Date: Sep. 18, 2014

(65) Prior Publication Data
US 2016/0016933 A1    Jan. 21, 2016

Related U.S. Application Data

(60) Provisional application No. 61/775,735, filed on Mar. 11, 2013.

(51) Int. Cl.
| | | |
|---|---|---|
| *C07D 217/12* | (2006.01) | |
| *C07D 401/04* | (2006.01) | |
| *C07D 405/04* | (2006.01) | |
| *A61K 31/4709* | (2006.01) | |
| *C07D 401/12* | (2006.01) | |
| *C07D 401/14* | (2006.01) | |
| *C07D 405/14* | (2006.01) | |
| *C07D 405/12* | (2006.01) | |
| *A61K 31/4725* | (2006.01) | |
| *A61K 31/497* | (2006.01) | |
| *A61K 31/5377* | (2006.01) | |
| *C07D 417/14* | (2006.01) | |

(52) U.S. Cl.
CPC ......... *C07D 401/12* (2013.01); *A61K 31/4725* (2013.01); *A61K 31/497* (2013.01); *A61K 31/5377* (2013.01); *C07D 401/04* (2013.01); *C07D 401/14* (2013.01); *C07D 405/04* (2013.01); *C07D 405/12* (2013.01); *C07D 405/14* (2013.01); *C07D 417/14* (2013.01)

(58) Field of Classification Search
None
See application file for complete search history.

(56) References Cited

U.S. PATENT DOCUMENTS

| | | |
|---|---|---|
| 8,575,184 B2 | 11/2013 | Johnson et al. |
| 9,050,345 B2 | 6/2015 | Finlay et al. |
| 9,242,966 B2 | 1/2016 | Finlay et al. |
| 2012/0232068 A1 | 9/2012 | Johnson et al. |
| 2014/0031345 A1 | 1/2014 | Johnson et al. |
| 2014/0256719 A1 | 9/2014 | Finlay et al. |
| 2014/0303168 A1 | 10/2014 | Finlay et al. |
| 2016/0009719 A1 | 1/2016 | Finlay et al. |

FOREIGN PATENT DOCUMENTS

| | | |
|---|---|---|
| DE | 196 51 099 A1 | 6/1998 |
| JP | 2013-32343 A | 2/2013 |
| WO | WO 03/013523 A1 | 2/2003 |
| WO | WO 2005/030130 A2 | 4/2005 |
| WO | WO 2006/097441 A1 | 9/2006 |
| WO | WO 2006/127329 A1 | 11/2006 |
| WO | WO 2007/117161 A1 | 10/2007 |
| WO | WO 2008/003702 A2 | 1/2008 |
| WO | WO 2011/028741 A1 | 3/2011 |
| WO | WO 2011/082337 A1 | 7/2011 |
| WO | WO 2011/163610 A2 | 12/2011 |
| WO | WO 2013/012915 A1 | 1/2013 |
| WO | WO 2014/143606 A1 | 9/2014 |
| WO | WO 2014/143607 A1 | 9/2014 |
| WO | WO 2014/143608 A1 | 9/2014 |

OTHER PUBLICATIONS

Thaimattam et al, Bioorganic & Medicinal Chemistry, 13 (2005) 4704-4712.*
International Preliminary Report on Patentability for PCT/US2014/022264 issued Sep. 15, 2015.*
Finlay et al., U.S. Appl. No. 14/772,152, filed Sep. 2, 2015.

* cited by examiner

*Primary Examiner* — Zinna Northington Davis
(74) *Attorney, Agent, or Firm* — Mary K. VanAtten

(57) ABSTRACT

A compound of formula (I) (I) wherein A, R1, R1a, R3 and R24 are described herein. The compounds are useful as inhibitors of potassium channel function and in the treatment and prevention of arrhythmia, IKur-associated disorders, and other disorders mediated by ion channel function.

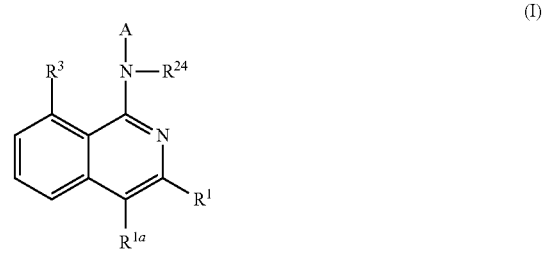

(I)

18 Claims, No Drawings

ISOQUINOLINES AS POTASSIUM ION CHANNEL INHIBITORS

CROSS-REFERENCE TO RELATED APPLICATIONS

This application is the National Stage filed under 35 U.S.C. §371 of PCT Application No. PCT/US2014/022264, filed Mar. 10, 2014, which claims the benefit of U.S. Provisional Patent Application Ser. No. 61/775,735 filed Mar. 11, 2013, whose contents are herein incorporated by reference in their entirety.

FIELD OF THE INVENTION

The present invention provides for isoquinolines useful as inhibitors of potassium channel function (especially inhibitors of the $K_v1$ subfamily of voltage gated $K^+$ channels, more especially inhibitors of $K_v1.5$ (which have been linked to the ultra-rapidly activating delayed rectifier $K^+$ current $I_{Kur}$), and/or $K_v1.3$ channels, and/or $K_v1.1$ channels) and to pharmaceutical compositions containing such compounds. The present invention further provides for methods of using such compounds in the treatment and prevention of arrhythmia, $I_{Kur}$-associated disorders, and other disorders mediated by ion channel function.

BACKGROUND OF THE INVENTION

The ultra-rapidly activating delayed rectifier $K^+$ current ($I_{Kur}$) is believed to represent the native counterpart to a cloned potassium channel designated $K_v1.5$ and, while present in human atrium, it appears to be absent in human ventricle. Furthermore, because of its rapidity of activation and limited slow inactivation, $I_{Kur}$ is believed to contribute significantly to repolarization in human atrium. Consequently, a specific blocker of $I_{Kur}$, that is a compound which blocks $K_v1.5$, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III antiarrhythmic agents. (Antiarrhythmic agents of Class III are drugs that cause a selective prolongation of the duration of the action potential without significant cardiac depression.)

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves' ophthalmopathy and asthma. Although the underlying pathogenesis of each of these conditions may vary, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, lymphocytes recognize the foreign tissue antigens and begin to produce immune mediators which lead to graft rejection or graft-vs-host rejection.

One end result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion in which both the normal and autoimmune responses are shut off. Indeed, patients treated with such nonspecific immunosuppressive agents are as likely to succumb to infection as they are to their autoimmune disease.

Cyclosporin A, which was approved by the US FDA in 1983 is currently the leading drug used to prevent rejection of transplanted organs. In 1993, FK-506 (PROGRAF®) was approved by the US FDA for the prevention of rejection in liver transplantation. Cyclosporin A and FK-506 act by inhibiting the body's immune system from mobilizing its vast arsenal of natural protecting agents to reject the transplant's foreign protein. In 1994, Cyclosporin A was approved by the US FDA for the treatment of severe psoriasis and has been approved by European regulatory agencies for the treatment of atopic dermatitis. Though these agents are effective in fighting transplant rejection, Cyclosporin A and FK-506 are known to cause several undesirable side effects including nephrotoxicity, neurotoxicity, and gastrointestinal discomfort. Therefore, a selective immunosuppressant without these side effects still remains to be developed. Potassium channel inhibitors as described here promise to be the solution to this problem, since inhibitors of $K_v1.3$, for example, are immunosuppressive. See Wulff et al., "Potassium channels as therapeutic targets for autoimmune disorders", *Curr. Opin. Drug Discov. Devel.*, 6(5):640-647 (September 2003); Shah et al, "Immunosuppressive effects of a $K_v1.3$ inhibitor", *Cell Immunol.*, 221(2):100-106 (February 2003); Hanson et al., "UK-78, 282, a novel piperidine compound that potently blocks the $K_v1.3$ voltage-gated potassium channel and inhibits human T cell activation", *Br. J. Pharmacol.*, 126(8):1707-1716 (April 1999).

Inhibitors of $K_v1.5$ and other $K_v1.x$ channels stimulate gastrointestinal motility. Thus, the compounds of the invention are believed to be useful in treating motility disorders such as reflux esophagitis. See Frey et al., "Blocking of cloned and native delayed rectifier K channels from visceral smooth muscles by phencyclidine", *Neurogastroenterol. Motil.*, 12(6):509-516 (December 2000); Hatton et al., "Functional and molecular expression of a voltage-dependent K(+) channel ($K_v1.1$) in interstitial cells of Cajal", *J. Physiol.*, 533(Pt 2):315-327 (Jun. 1, 2001); Vianna-Jorge et al., "Shaker-type $K_v1$ channel blockers increase the peristaltic activity of guinea-pig ileum by stimulating acetylcholine and tachykinins release by the enteric nervous system", *Br. J. Pharmacol.*, 138(1):57-62 (January 2003); Koh et al., "Contribution of delayed rectifier potassium currents to the electrical activity of murine colonic smooth muscle", *J. Physiol.*, 515(Pt. 2):475-487 (Mar. 1, 1999).

Inhibitors of $K_v1.5$ relax pulmonary artery smooth muscle. Thus, the compounds of the invention are believed to be useful in treating hypertension and otherwise improving vascular health. See Davies et al., "$K_v$ channel subunit expression in rat pulmonary arteries", *Lung*, 179(3):147-161 (2001), Epub. Feb. 4, 2002; Pozeg et al., "In vivo gene transfer of the 02-sensitive potassium channel $K_v1.5$ reduces pulmonary hypertension and restores hypoxic pulmonary vasoconstriction in chronically hypoxic rats", *Circulation*, 107(15):2037-2044 (Apr. 22, 2003), Epub. Apr. 14, 2003.

Inhibitors of $K_v1.3$ increase insulin sensitivity. Hence, the compounds of the invention are believed to be useful in treating diabetes. See Xu et al., "The voltage-gated potassium channel $K_v1.3$ regulates peripheral insulin sensitivity", *Proc. Natl. Acad. Sci. U.S.A.*, 101(9):3112-3117 (Mar. 2, 2004), Epub. Feb. 23, 2004; MacDonald et al., "Members of the K$_v$1 and K$_v$2 voltage-dependent K(+) channel families regulate insulin secretion", *Mol. Endocrinol.*, 15(8):1423-1435 (August 2001); MacDonald et al., "Voltage-dependent K(+) channels in pancreatic beta cells: role, regulation and potential as therapeutic targets", *Diabetologia*, 46(8):1046-1062 (August 2003), Epub. Jun. 27, 2003.

Stimulation of K$_v$1.1 is believed to reduce seizure activity by hyperpolarizing neurons. Thus, the compounds of the invention are believed to be useful in treating seizures, including seizures associated with epilepsy and other neurological diseases. See Rho et al., "Developmental seizure susceptibility of kv1.1 potassium channel knockout mice", *Dev. Neurosci.*, 21(3-5):320-327 (November 1999); Coleman et al., "Subunit composition of K$_v$1 channels in human CNS", *J. Neurochem.*, 73(2):849-858 (August 1999); Lopantsev et al., "Hyperexcitability of CA3 pyramidal cells in mice lacking the potassium channel subunit K$_v$1.1", *Epilepsia*, 44(12):1506-1512 (December 2003); Wickenden, "Potassium channels as anti-epileptic drug targets", *Neuropharmacology*, 43(7):1055-1060 (December 2002).

Inhibition of K$_v$1.x channels improves cognition in animal models. Thus, the compounds of the invention are believed to be useful in improving cognition and/or treating cognitive disorders. See Cochran et al., "Regionally selective alterations in local cerebral glucose utilization evoked by charybdotoxin, a blocker of central voltage-activated K+-channels", *Eur. J. Neurosci.*, 14(9):1455-1463 (November 2001); Kourrich et al., "Kaliotoxin, a K$_v$1.1 and K$_v$1.3 channel blocker, improves associative learning in rats", *Behav. Brain Res.*, 120(1):35-46 (Apr. 8, 2001).

SUMMARY OF THE INVENTION

In accordance with the present invention, acyclic compounds and related compounds are provided that have the general structure of formula (I):

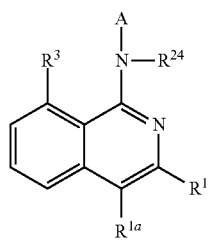

(I)

wherein A, R$^1$, R$^{1a}$, R$^3$, and R$_{24}$ are defined below.

By use of a respective effective amount of at least one compound described herein, provided are methods of treating (including ameliorating), reducing the risk of or preventing arrhythmias, atrial fibrillation, atrial flutter, supraventricular arrhythmias, gastrointestinal disorders (such as reflux esophagitis or a motility disorder), inflammatory or immunological disease (such as chronic obstructive pulmonary disease), diabetes, cognitive disorders, migraine, epilepsy, hypertension, or treating I$_{Kur}$-associated conditions, or controlling heart rate.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti-thrombotic/anti-thrombolytic agent (such as tPA, recombinant tPA, TNK, nPA, factor VIIa inhibitors, factor Xa inhibitors (such as apixaban), factor XIa inhibitors or thrombin inhibitors), or at least one anti-coagulant (such as warfarin or a heparin), or at least one HMG-CoA reductase inhibitor (pravastatin, lovastatin, atorvastatin, simvastatin, NK-104 or ZD-4522), or at least one anti-diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

Another aspect of this invention is directed to methods of treating, inhibiting, or ameliorating the symptoms of a disease or disorder that is modulated or otherwise affected by inhibitors of potassium channel function (especially inhibitors of the K$_v$1 subfamily of voltage gated K$^+$ channels, more especially inhibitors of K$_v$1.5 (which have been linked to the ultra-rapidly activating delayed rectifier K$^+$ current I$_{Kur}$), and/or K$_v$1.3 channels, and/or K$_v$1.1 channels), comprising administering to a subject in need thereof a therapeutically effective amount of a compound of the present invention or an individual isomer or mixture of isomers or a pharmaceutically acceptable salt thereof.

Another aspect of this invention is directed to methods of treating, inhibiting, or ameliorating arrhythmia, or maintaining normal sinus rhythm, comprising administering to a subject in need thereof a therapeutically effective amount of a compound of the present invention or an individual isomer or mixture of isomers or a pharmaceutically acceptable salt thereof.

Another aspect of this invention is directed to methods of controlling heart rate, comprising administering to a subject in need thereof a therapeutically effective amount of a compound of the present invention or an individual isomer or mixture of isomers or a pharmaceutically acceptable salt thereof.

DEFINITIONS

The terms "alk" or "alkyl" refer to straight or branched chain hydrocarbon groups having 1 to 12 carbon atoms, or 1 to 8 carbon atoms, 1 to 6 carbon atoms, 1 to 4 carbon atoms, or 1 to 3 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of R$^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be fused, bridged and/or joined through one or more spiro unions. The term "substituted cycloalkyl" refers to a cycloalkyl group substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The term "haloalkyl" is intended to include both branched and straight-chain saturated aliphatic hydrocarbon groups, for example $CF_3$, having the specified number of carbon atoms, substituted with one or more halogen, up to and including perhalo alkyls (where all hydrogen atoms are replaced with a halogen).

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

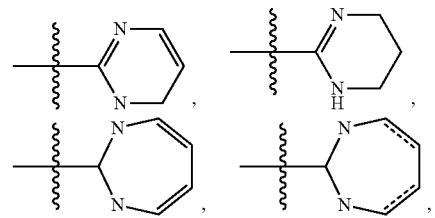

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

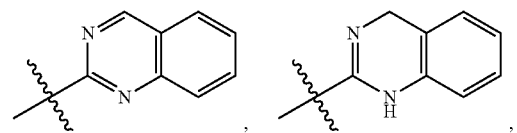

-continued

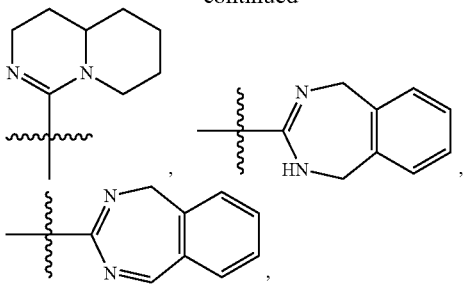

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

The term "alkanoyl" refers to alkyl group (which may be optionally substituted as described above) linked to a carbonyl group (i.e., —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

Compounds described herein may form salts or solvates which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety and an acidic moiety, zwitterions ("inner salts") may be formed and are included within the term "salt(s)" as used herein. In one embodiment, the salts are pharmaceutically acceptable (i.e., non-toxic, physiologically acceptable), although other salts are also useful, e.g., in isolation or purification steps which may be employed during preparation. Salts of the compounds described herein may be formed, for example, by reacting a compound with an amount of acid or base, such as an equivalent amount, in a medium such as one in which the salt precipitates or in an aqueous medium followed by lyophilization.

The present invention is intended to cover the compounds in their neutral state, salts of those compounds, or mixtures of the compounds in their neutral state with one or more salt forms, or mixtures of salt forms.

The compounds described herein which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds described herein which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Any compound that can be converted in vivo to provide the bioactive agent (i.e., the compound of formula (I)) is a prodrug within the scope and spirit of the invention.

The term "prodrugs" as employed herein includes esters and carbonates formed by reacting one or more hydroxyls of compounds of formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) Bundgaard, H., ed., *Design of Prodrugs*, Elsevier (1985);

c) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

The various compounds described herein, or their pharmaceutically acceptable salts, may contain one or more asymmetric centers and may thus give rise to isomers, such as enantiomers, diastereomers, and other stereoisomeric forms. Such forms may be defined, in terms of absolute stereochemistry, as (R)- or (S)-, or as (D)- or (L)- for amino acids. The present invention is meant to include all such possible individual stereoisomers and mixtures thereof, including their racemic and optically pure enantiomeric or diastereomeric forms. The compounds may be prepared as racemates and can conveniently be used as such, or optically active (+) and (−), (R)- and (S)-, or (D)- and (L)-isomers or corresponding diastereomers may be prepared using chiral synthons or chiral reagents, or they may be resolved from racemic mixtures using conventional techniques, such as chiral chromatography or reverse phase HPLC. When the compounds described herein contain olefinic double bonds or other centers of geometric asymmetry, and unless specified otherwise, it is intended that the compounds include both E and Z geometric isomers.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^{2}$H or D and $^{3}$H or T, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^{3}$H, and carbon-14, $^{14}$C, are particularly useful for this purpose in view of their ease of incorporation and ready means of detection. Substitution with heavier isotopes such as deuterium, $^{2}$H or D, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{18}$F, $^{15}$O, and $^{13}$N, can be useful in Positron Emission Topography (PET) studies for examining substrate receptor occupancy.

To the extent that compounds described herein, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms are contemplated within the scope of this invention. Individual stereoisomers of the compounds of the invention may, for example, be substantially free of other isomers, or may be admixed, for example, as racemates or with all other, or other selected, stereoisomers.

"Stable compound" and "stable structure" are meant to indicate a compound that is sufficiently robust to survive isolation to a useful degree of purity from a reaction mixture, and formulation into an efficacious therapeutic agent. The present invention is intended to cover stable compounds.

When any variable (e.g., $R^{13}$) occurs more than one time in any constituent or formula for a compound, its definition at each occurrence is independent of its definition at every other occurrence. Thus, for example, if a group is shown to be substituted with 0-2 $R^{13}$, then said group may optionally be substituted with up to two $R^{13}$ groups and $R^{13}$ at each occurrence is selected independently from the definition of $R^{13}$. Also, combinations of substituents and/or variables are permissible only if such combinations result in stable compounds.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Treating" or "treatment" as used herein covers the treatment, prophylaxis, and/or reducing the risk, of a disease or disorder described herein, or treatment, prophylaxis, or reducing the risk of a symptom of a disease or disorder, in a subject, such as a human, and includes:

i. inhibiting a disease or disorder, i.e., arresting its development; or ii. relieving a disease or disorder, i.e., causing regression of the disorder.

"Subject" refers to a warm blooded animal such as a mammal, such as a human, or a human child, which is afflicted with, or has the potential to be afflicted with one or more diseases and disorders described herein.

The terms "including", "such as", "for example" and the like are intended to refer to exemplary embodiments and not to limit the scope of the present invention.

DETAILED DESCRIPTION OF THE INVENTION

In accordance with the present invention, compounds of formula (I) are provided

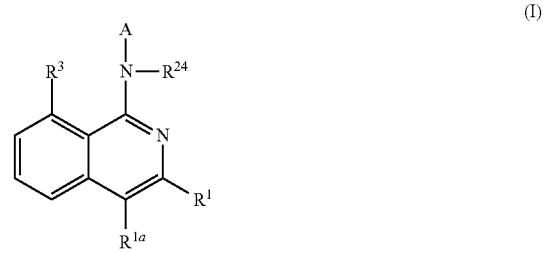

(I)

or enantiomers, diastereomers, tautomers, prodrugs or salts thereof, wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

one of R$^1$ or R$^{1a}$ is C$_{1-10}$ alkyl substituted with 1-2 —OH, haloC$_{1-10}$ alkyl, C$_{2-12}$ alkenyl, or C$_{3-10}$ cycloalkyl, wherein the cycloalkyl may be substituted with 0-2 R$^{13}$; or $R^1$ is

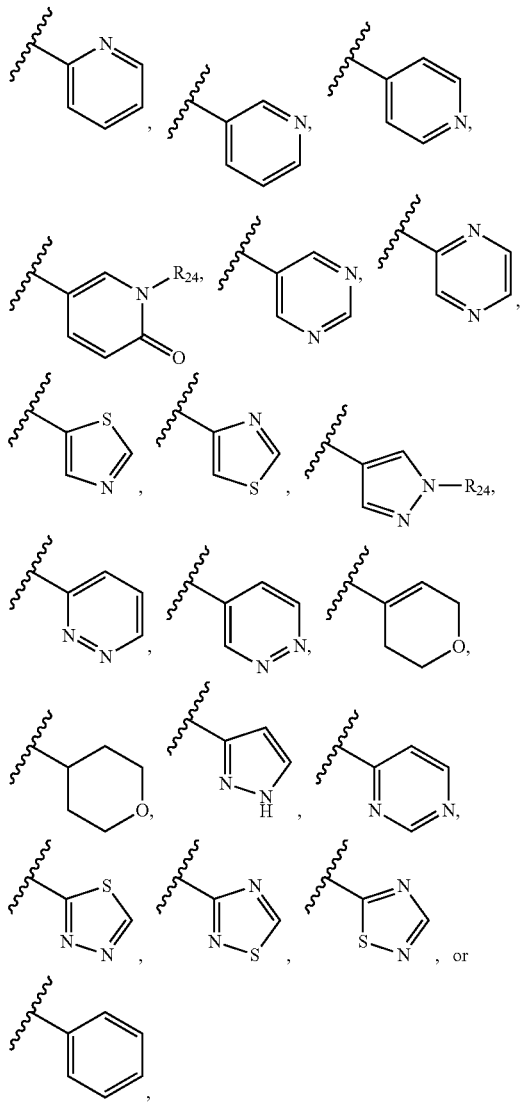

any of which may be substituted with 0-2 $R^{13}$;

the other of $R^1$ or $R^{1a}$ is hydrogen, $C_{1-3}$alkyl, —C(O)—NH$_2$, —S—CH$_3$, cyano, or halo;

$R^2$ is phenyl, cyclopentyl, pyridinyl, pyrazinyl, pyrimidinyl, piperidinyl, pyridinone, pyrrolidinyl, tetrahydropyranyl, or thiazolyl, any of which are substituted with 0-2 $R^{2a}$;

$R^{2a}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_m$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NR$^{14}$COR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyran, or tetrahydropyran, any of which may be substituted with 0-1 $R^{3a}$;

$R^{3a}$ is halo, CN, NH$_2$, —O—$C_{1-3}$alkyl, or morpholinyl;

$R^{13}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$, —NR$^{14}$COR$^{14}$, or OR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$^{26}$, —CO$_2$NR$^{24}$R$^{24}$, —OCF$_3$, —OR$^{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, —SO$_2$NR$^{24}$R$^{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{3-6}$cycloalkyl, or phenyl;

$R^{26}$, at each occurrence, is independently selected from hydrogen, $C_{1-10}$alkyl, $C_{3-6}$cycloalkyl, or phenyl;

m is 0 to 4;

n is 0 to 4; and n–1 is 2 to 4.

In another aspect, the present invention provides compound of formula (Ia), wherein:

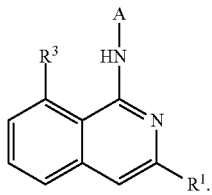
(Ia)

In another aspect, the present invention provides compound of formula (Ib), or an enantiomer, diastereomer, tautomer, or salt thereof, wherein:

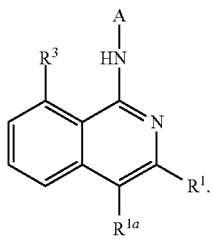
(Ib)

In another aspect, the present invention provides compound of formula (Ib), or an enantiomer, diastereomer, tautomer, or salt thereof, wherein:

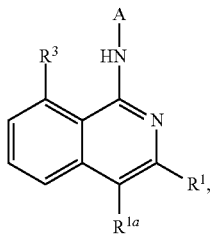
(Ib)

and wherein
$R^1$ is selected from hydrogen or halo; and
$R^{1a}$ is selected from

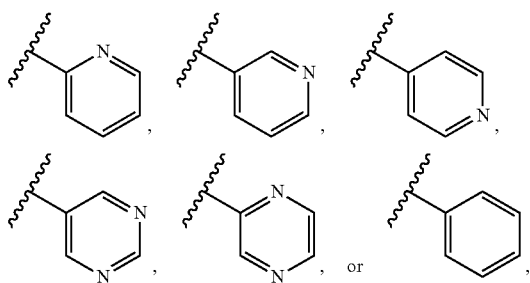

any of which may be substituted with 0-2 $R^{13}$.

In another aspect, the present invention provides compound of formula (Ib), or an enantiomer, diastereomer, tautomer, or salt thereof,

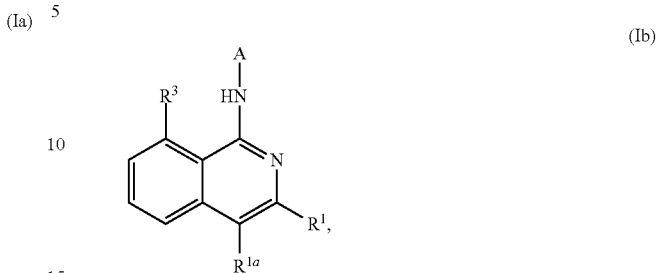
(Ib)

wherein:
$R^1$ is phenyl or

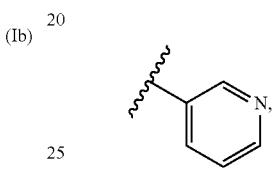

any of which may be substituted with 0-2 $R^{13}$.

In another aspect, the present invention provides compound of formula (I), (Ia) or (Ib), wherein:
one of $R^1$ or $R^{1a}$ is $C_{1-10}$ alkyl substituted with 1-2 —OH, halo$C_{1-10}$ alkyl, or $C_{3-10}$ cycloalkyl, wherein the cycloalkyl may be substituted with 0-2 $R^{13}$; or

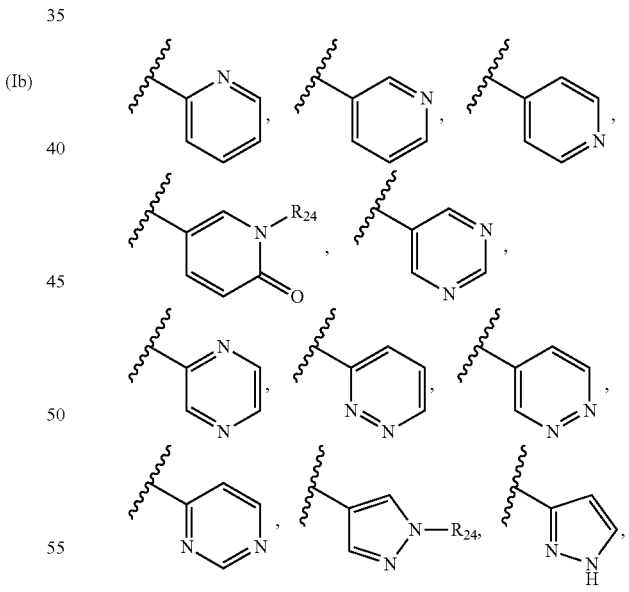

any of which may be substituted with 0-2 $R^{13}$.

In another aspect, the present invention provides compound of formula (I), (Ia) or (Ib), or enantiomers, diastereomers, tautomers, prodrugs or salts thereof wherein one of $R^1$ or $R^{1a}$ is $C_{1-10}$ alkyl substituted with 1-2 —OH, haloC$_{1-10}$ alkyl, or $C_{3-10}$ cycloalkyl, wherein the cycloalkyl may be substituted with 0-2 $R^{13}$; or $R^1$ is

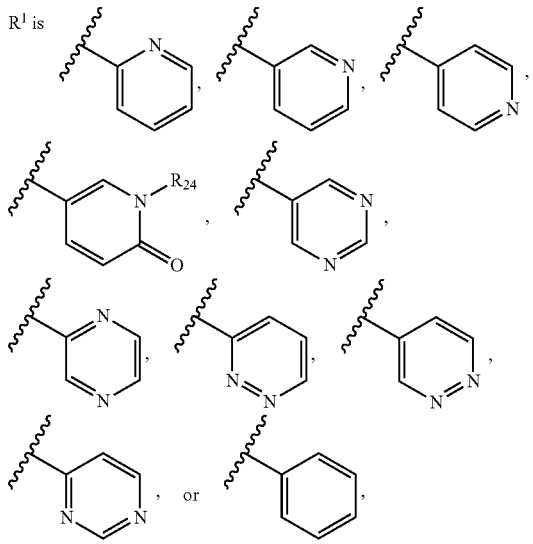

any of which may be substituted with 0-2 $R^{13}$.

In another aspect, the present invention provides compound of formula (I), (Ia) or (Ib), or enantiomers, diastereomers, tautomers, prodrugs or salts thereof wherein $R^1$ is $C_{1-10}$ alkyl substituted with 1-2 —OH, haloC$_{1-10}$ alkyl, or $C_{3-10}$ cycloalkyl, wherein the cycloalkyl may be substituted with 0-1 $R^{13}$; or $R^1$ is

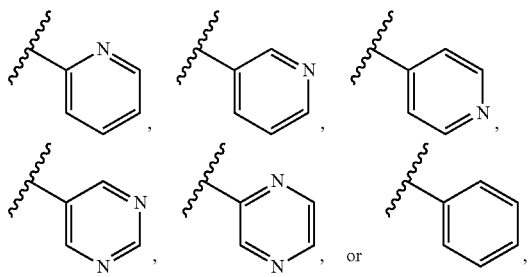

any of which may be substituted with 0-2 $R^{13}$.

In another aspect, the present invention provides compound of formula (I), (Ia) or (Ib), or enantiomers, diastereomers, tautomers, prodrugs or salts thereof wherein $R^1$ is $C_{1-10}$ alkyl substituted with 1-2 —OH, haloC$_{1-10}$ alkyl, or $C_{3-10}$ cycloalkyl, wherein the cycloalkyl may be substituted with 0-1 $R^{13}$; or $R^1$ is

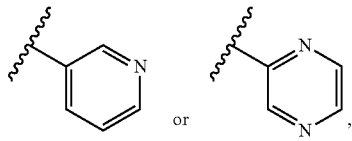 [SMILES: *c1cccnc1 ; *c1cnccn1]

any of which may be substituted with 0-2 $R^{13}$.

In another aspect, the present invention provides compound of formula (I), (Ia) or (Ib), or enantiomers, diastereomers, tautomers, prodrugs or salts thereof wherein $R^1$ is

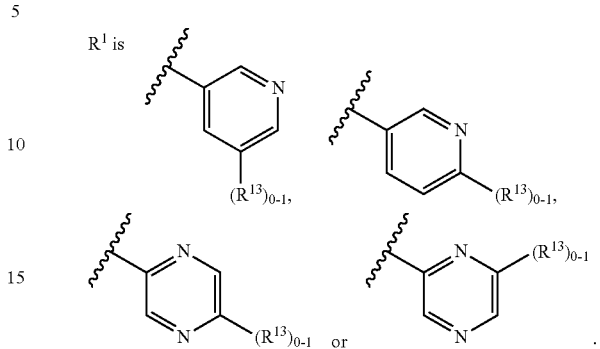

In another aspect, the present invention provides compound of formula (I), (Ia) or (Ib), or enantiomers, diastereomers, tautomers, prodrugs or salts thereof wherein $R^{13}$, at each occurrence, is independently H, —OH, F, Cl, Br, I, $C_{1-6}$ alkyl, $C_{1-6}$ alkoxy, haloC$_{1-6}$ alkyl, $C_{3-6}$ cycloalkyl, phenyl, or a 4- to 12-membered heteroaryl, wherein the heteroaryl is selected from tetrazolyl, —CN, —NO$_2$, —(CH$_2$)$_m$—SO$_2$R$^{14}$, —NR$^{14}$SO$_2$R$^{14}$, —CONR$^{14}$R$^{14}$, —(CH$_2$)$_m$—SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —NR$^{14}$CO$_2$R$^{14}$, —CO$_2$R$^{14}$, or —NR$^{14}$R$^{14}$, wherein the alkyl, cycloalkyl, phenyl, and heteroaryl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or alternatively, two $R^{14b}$'s are taken together with the atoms to which they are attached to form a cyclic ring, wherein the cyclic ring is morpholinyl, piperidinyl, or piperazinyl, and may be substituted with 0-1 $C_{1-6}$alkyl; and $R^{14a}$, at each occurrence, is independently selected from F, Cl, Br, I, $C_{1-6}$ alkyl, haloC$_{1-6}$alkyl, phenyl, or $C_{3-6}$cycloalkyl.

In another aspect, the present invention provides compound of formula (I) or (Ia), or enantiomers, diastereomers, tautomers, prodrugs or salts thereof wherein $R^{13}$, at each occurrence, is independently H, —OH, F, Cl, Br, I, $C_{1-6}$ alkyl, $C_{1-6}$ alkoxy, haloC$_{1-6}$ alkyl, $C_{3-6}$ cycloalkyl, phenyl, or a 4- to 12-membered heteroaryl, wherein the heteroaryl is selected from tetrazolyl, —CN, —NO$_2$, —(CH$_2$)$_m$—SO$_2$R$^{14}$, —NR$^{14}$SO$_2$R$^{14}$, —CONR$^{14}$R$^{14}$, —(CH$_2$)$_m$—SO$_2$NR$^{14}$R$^{14}$, —NR$^{14}$CO$_2$NR$^{14}$R$^{14}$, —NR$_{14}$CO$_2$NR$_{14}$R$^{1b}$, —NR$^{14}$COR$^{14}$, —NR$^{14}$CO$_2$R$^{14}$, —CO$_2$R$^{14}$, or —NR$^{14}$R$^{14}$, wherein the alkyl, cycloalkyl, phenyl, and heteroaryl may be substituted with 0-2 $R^{14a}$, and the heteroaryl and heterocyclyl consist of carbon atoms and 1, 2, 3, or 4 heteroatoms independently selected from the group consisting of N, S, or O; $R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or alternatively, two $R^{14}$'s are taken together with the atoms to which they are attached to form a cyclic ring, wherein the cyclic ring is morpholinyl, piperidinyl, or piperazinyl, and may be substituted with 0-1 $C_{1-6}$alkyl; and $R^{14a}$, at each occurrence, is independently selected from F, Cl, Br, I, $C_{1-6}$ alkyl, halo$C_{1-6}$alkyl, phenyl, or $C_{3-6}$cycloalkyl.

In another aspect, the present invention provides compound of formula (I) or (Ia), or enantiomers, diastereomers, tautomers, prodrugs or salts thereof wherein $R^{13}$, at each occurrence, is independently H, $C_{1-6}$ alkyl, or a 4- to 12-membered heteroaryl, wherein the heteroaryl is selected from tetrazolyl, —CN, —NR$^{14}$SO$_2$R$^{14}$, —CONR$^{14}$R$^{14}$, —SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —CO$_2$R$^{14}$, or —NR$^{14}$R$^{14}$, wherein the alkyl, and heteroaryl may be substituted with 0-2 $R^{14a}$;

$R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or two $R^{14b}$'s are taken together with the atoms to which they are attached to form a cyclic ring, wherein the cyclic ring is morpholinyl, and may be substituted with 0-1 $C_{1-6}$alkyl; and $R^{14a}$, at each occurrence, is independently selected from F, Cl, Br, I, $C_{1-6}$ alkyl, halo$C_{1-6}$alkyl, phenyl, or $C_{3-6}$cycloalkyl.

In another aspect, the present invention provides compound of formula (I) or (Ia), or enantiomers, diastereomers, tautomers, prodrugs or salts thereof wherein $R^{13}$, at each occurrence, is independently H, $C_{1-6}$ alkyl, or a 4- to 12-membered heteroaryl, wherein the heteroaryl is selected from tetrazolyl, —CN, —NR$^{14}$SO$_2$R$^{14}$, —CONR$^{14}$R$^{14}$, —SO$_2$NR$^{14}$R$^{14}$, —NR$^{14}$CO$_2$NR$^{14}$R$^{14}$, —NR$^{14}$CO$_2$NR$^{14}$R$^{14}$, —NR$^{14}$COR$^{14}$, —CO$_2$R$^{14}$, or —NR$^{14}$R$^{14}$, wherein the alkyl, and heteroaryl may be substituted with 0-2 $R^{14a}$;

$R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or two $R^{14}$'s are taken together with the atoms to which they are attached to form a cyclic ring, wherein the cyclic ring is morpholinyl, and may be substituted with 0-1 $C_{1-6}$alkyl; and $R^{14a}$, at each occurrence, is independently selected from F, Cl, Br, I, $C_{1-6}$ alkyl, halo$C_{1-6}$alkyl, phenyl, or $C_{3-6}$cycloalkyl.

In another aspect, the present invention provides compound of formula (I) or (Ia), or enantiomers, diastereomers, tautomers, prodrugs or salts thereof wherein $R^{13}$, at each occurrence, is independently H, —CN, —NHSO$_2$R$^{14}$, —CONH$_2$, —SO$_2$NR$^{14}$R$^{14}$, —NHCO$_2$NR$^{14b}$R$^{14b}$, —NHCOR$^{14}$, or —NH$_2$; and $R^{14}$, at each occurrence, is independently selected from hydrogen, or methyl.

In another aspect, the present invention provides compound of formula (I) or (Ia), or enantiomers, diastereomers, tautomers, prodrugs or salts thereof wherein $R^{13}$, at each occurrence, is independently H, —CN, —NHSO$_2$R$^{14}$, —CONH$_2$, —SO$_2$NR$^{14}$R$^{14}$, —NHCO$_2$NR$^{14}$R$^{14}$, —NHCOR$^{14}$, or —NH$_2$; and $R^{14}$, at each occurrence, is independently selected from hydrogen or methyl.

In another aspect, the present invention provides compound of formula (I) or (Ia), or enantiomers, diastereomers, tautomers, prodrugs or salts thereof wherein $R^{13}$, at each occurrence, is —SO$_2$NH$_2$.

In another aspect, the present invention provides compound of formula (I) or (Ia), or enantiomers, diastereomers, tautomers, prodrugs or salts thereof wherein A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

$R^2$ is phenyl, pyridinyl, pyrazinyl, pyrimidinyl, piperidinyl, or pyridinone, any of which are substituted with 0-2 $R^{2a}$; and $R^{2a}$, at each occurrence, is independently H, —OH, F, $C_{1-6}$ alkyl, $C_{1-6}$ alkoxy, or 6-SO$_2$NR$^{14}$R$^{14}$.

In another aspect, the present invention provides compound of formula (I) or (Ia), or enantiomers, diastereomers, tautomers, prodrugs or salts thereof wherein A is —(CH$_2$)—R$^2$;
$R^2$ is phenyl,

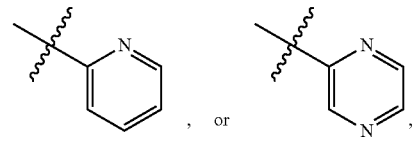 [SMILES: *c1ccccn1 ; *c1cnccn1]

, or any of which are substituted with 0-1 $R^{2a}$; and $R^{2a}$, at each occurrence, is independently H, —OH, F, $C_{1-6}$ alkyl, $C_{1-6}$ alkoxy, $C_{1-6}$ haloalkoxy, or SO$_2$NR$^{14}$R$^{14}$.

In another aspect, the present invention provides compound of formula (I) or (Ia), or enantiomers, diastereomers, tautomers, prodrugs or salts thereof wherein A is —(CH$_2$)—R$^2$;
$R^2$ is phenyl,

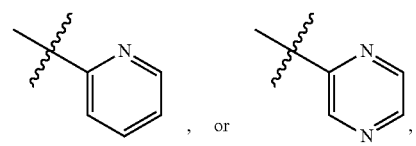 [SMILES: *c1ccccn1 ; *c1cnccn1]

, or any of which are substituted with 0-1 $R^{2a}$; and $R^{2a}$, at each occurrence, is independently H, —OH, F, $C_{1-6}$ alkyl, $C_{1-6}$ alkoxy, $C_{1-6}$ haloalkoxy, or SO$_2$NR$^{14}$R$^{14}$.

In another aspect, the present invention provides compound of formula (I) or (Ia), or enantiomers, diastereomers, tautomers, prodrugs or salts thereof wherein A is —(CH$_2$)—R$^2$; and
$R^2$ is phenyl or

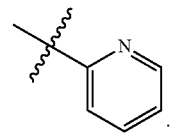 [SMILES: *c1ccccn1]

In another aspect, the present invention provides compound of formula (I) or (Ia), or enantiomers, diastereomers, tautomers, prodrugs or salts thereof wherein A is —(CH$_2$)—R$^2$;
R$^2$ is phenyl,

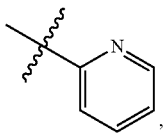

or C$_{1-6}$alkyl, any of which are substituted with 0-1 R$^{2a}$; and
R$^{2a}$, at each occurrence, is independently H or F.

In another aspect, the present invention provides compound of formula (I) or (Ia), or enantiomers, diastereomers, tautomers, prodrugs or salts thereof wherein
R$^3$ is phenyl.

In another aspect, the present invention provides compound of formula (I) or (Ia), or enantiomers, diastereomers, tautomers, prodrugs or salts thereof wherein
R$^{24}$, at each occurrence, is independently selected from hydrogen, C$_{1-6}$alkyl, C$_{3-6}$cycloalkyl, or phenyl;
R$^{25}$, at each occurrence, is independently selected from hydrogen, C$_{1-6}$alkyl, C$_{3-6}$cycloalkyl, or phenyl; and
R$^{26}$, at each occurrence, is independently selected from hydrogen, C$_{1-6}$alkyl, C$_{3-6}$cycloalkyl, or phenyl.

In another aspect, the present invention provides compound of formula (I) or (Ia), or enantiomers, diastereomers, tautomers, prodrugs or salts thereof wherein
R$^{24}$, at each occurrence, is independently selected from hydrogen, methyl or ethyl;
R$^{25}$, at each occurrence, is independently selected from hydrogen methyl or ethyl; and
R$^{26}$, at each occurrence, is independently selected from hydrogen, methyl or ethyl.

In another aspect, the present invention provides compound of formula (I) or (Ia), or enantiomers, diastereomers, tautomers, prodrugs or salts thereof wherein
m is 0-2; and
n–1 is 1-2.

In another aspect, the present invention provides compound of formula (I) or (Ia), or enantiomers, diastereomers, tautomers, prodrugs or salts thereof wherein
m is 1 or 2;
n–1 is 2; and
n is 1.

In another aspect, the present invention provides compound of formula (I) or (Ia), or enantiomers, diastereomers, tautomers, prodrugs or salts thereof wherein
R$^2$ is phenyl, cyclopentyl, pyridinyl, pyrazinyl, pyrimidinyl, piperidinyl, pyridinone, pyrrolidinyl, tetrahydropyranyl or thiazolyl, any of which are substituted with 0-2 R$^{2a}$; and
R$^2$ is C$_{1-6}$ alkyl.

In another aspect, the present invention provides compound of formula (I) or (Ia), or enantiomers, diastereomers, tautomers, prodrugs or salts thereof wherein R$^2$ is phenyl, cyclopentyl, pyridinyl, pyrazinyl, pyrimidinyl, piperidinyl, pyridinone, pyrrolidinyl, tetrahydropyranyl or thiazolyl, any of which are substituted with 0-2 R$^{2a}$; and
R$^2$ is C$_{1-6}$ alkyl.

In another aspect, the present invention provides compound of formula (I) or (Ia) or (Ib), or enantiomers, diastereomers, tautomers, prodrugs or salts thereof wherein
A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;
one of R$^1$ or R$^{1a}$ is C$_{1-10}$ alkyl substituted with 1-2 —OH, haloC$_{1-10}$ alkyl, C$_{2-12}$ alkenyl, or C$_{3-10}$ cycloalkyl, wherein the cycloalkyl may be substituted with 0-2 R$^{13}$; or
R$^1$ is

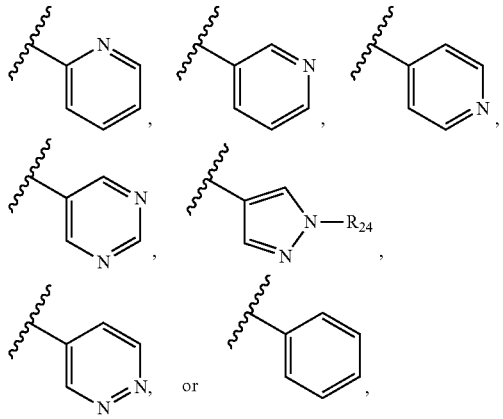

any of which may be substituted with 0-2 R$^{13}$;
the other of R$^1$ or R$^{1a}$ is hydrogen or halo;
R$^2$ is phenyl, cyclopentyl, pyridinyl, pyrimidinyl, pyrrolidinyl, or tetrahydropyranyl any of which are substituted with 0-2 R$^{2a}$;
R$^{2a}$, at each occurrence, is independently H, F, Cl, Br, I, C$_{1-6}$ alkyl, C$_{1-6}$ alkoxy, —NR$^{14}$R$^{14}$, —NR$_{14}$CONR$^{14}$, —C(=NOR$^{14}$)NR$^{14}$R$^{14}$, —CONR$^{14}$OR$^{14}$, or —NCOR$^{14}$, wherein the alkyl and alkoxy may be substituted with 0-2 R$^{14a}$;
R$^3$ is phenyl, pyridinyl, pyrimidinyl, dihydropyranyl, or tetrahydropyran, any of which may be substituted with 0-1 R$^{3a}$; and
R$^{3a}$ is halo.

In another embodiment, compounds, enantiomers, diastereomers, tautomers, or salt thereof, of the present invention are selected from the compounds exemplified in the examples.

In one embodiment, pharmaceutical compositions comprising a therapeutically effective amount of at least one compound of formula (I), (Ia), and/or compounds exemplified in the examples.

In another embodiment, pharmaceutical compositions comprising a therapeutically effective amount of at least one compound of formula (I), (Ia), and/or compounds exemplified in the examples, and at least one other therapeutic agent, for example, anti-arrhythmic agents, calcium channel blockers, anti-platelet agents, anti-hypertensive agents, anti-thrombotic/anti-thrombolytic agents, anti-coagulants, HMG-CoA reductase inhibitors, anti-diabetic agents, thyroid mimetics, mineralocorticoid receptor antagonists, and cardiac glycosides, are provided.

In yet another embodiment, pharmaceutical compositions comprising a therapeutically effective amount of at least one compound of formula (I), (Ia), or compounds exemplified in the examples, and at least one other therapeutic agent, for example, sotalol, dofetilide, diltiazem, verapamil, clopidogrel, cangrelor, ticlopidine, CS-747, ifetroban, aspirin, a beta adrenergic blocker, an ACE inhibitor, an A II antagonist, an ET antagonist, a dual ET/A II antagonist, a vasopepsidase inhibitor, tPA, recombinant tPA, TNK, nPA, a factor VIIa inhibitor, a factor Xa inhibitor, a factor XIa inhibitor, a thrombin inhibitor, warfarin, a heparin, pravastatin, lovastatin, atorvastatin, simvastatin, NK-104, ZD-4522, a biguanide, a biguanide/glyburide combination, spironolactone, eplerinone, digitalis and ouabain, are provided.

In still yet another embodiment, pharmaceutical compositions comprising a therapeutically effective amount of at least one compound of formula (I), (Ia), or compounds exemplified in the examples, and at least one other therapeutic agent, for example, captopril, zofenopril, fosinopril, enalapril, ceranopril, cilazopril, delapril, pentopril, quinapril, ramipril, lisinopril, omapatrilat, gemopatrilat, and apixaban, are provided.

In one embodiment, methods of treating or preventing arrhythmia comprising administering to a patient in need thereof an effective amount of at least one compound of formula (I), (Ia), or compounds exemplified in the examples, are provided.

In another embodiment, methods of treating or preventing supraventricular arrhythmia, for example, atrial fibrillation and atrial flutter, comprising administering to a patient in need thereof an effective amount of at least one compound of formula (I), (Ia), or compounds exemplified in the examples, are provided.

In one embodiment, a method of controlling heart rate comprising administering to a patient in need thereof an effective amount of at least one compound of formula (I), (Ia), or compounds exemplified in the examples, is provided.

In another embodiment, methods of treating an $I_{Kur}$-associated conditions, for example, gastrointestinal disorders, such as reflux esophagitis and a motility disorder; inflammatory and/or immunological diseases, such as chronic obstructive pulmonary disease; diabetes; cognitive disorders; migraines; epilepsy; and hypertension, comprising administering to a patient in need thereof an effective amount of at least one compound of formula (I), (Ia), or compounds exemplified in the examples, are provided.

Another aspect of this invention is directed to a composition comprising a compound of the invention together with a pharmaceutically acceptable carrier, diluent, or excipient. When water is a carrier or diluent, the composition optionally further comprises another pharmaceutically acceptable carrier or diluent and/or a pharmaceutically acceptable excipient. Within this aspect are such compositions for pharmaceutical use.

Another aspect of this invention is directed to treatment of diseases or disorders associated with inhibition of potassium channel function, wherein the disease or disorder is atrial fibrillation, controlling heart rate, and/or prophylactically treating arrhythmia, comprising administering a therapeutically effective amount of a compound of the present invention or an individual isomer or mixture of isomers or a pharmaceutically acceptable salt thereof.

The compounds of the invention may be useful in therapy.

The compounds of the invention may be used for the manufacture of a medicament for the treatment and/or prophylaxis of diseases or disorders associated with inhibition of potassium channel function, of the $K_v1$ subfamily of voltage gated $K^+$ channels, of $K_v1.5$ (which have been linked to the ultra-rapidly activating delayed rectifier $K^+$ current $I_{Kur}$, and/or $K_v1.3$ channels, and/or $K_v1.1$ channels.

The compounds of the invention can be used alone, in combination with other compounds of the present invention, or in combination with one or more, preferably one to two other agent(s).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The compounds of the present invention may be prepared by the exemplary processes described in the following schemes and working examples, as well as relevant published literature procedures that are used by one skilled in the art. Exemplary reagents and procedures for these reactions appear hereinafter and in the working examples. Protection and de-protection of functional groups in the processes below may be carried out by procedures generally known in the art (see, for example, Greene, T. W. et al., *Protecting Groups in Organic Synthesis*, Third Edition, Wiley (1999). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure*, Fourth Edition, Wiley & Sons, New York, N.Y. (1992); Katritzky, A. R. et al., eds., *Comprehensive Organic Functional Groups Transformations*, First Edition, Elsevier Science Inc., Tarrytown, N.Y. (1995); Larock, R. C., *Comprehensive Organic Transformations*, VCH Publishers, Inc., New York, N.Y. (1989); and references therein.

ABBREVIATIONS

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "Rt" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, SFC for supercritical fluid chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Solvents, temperatures, pressures, and other reaction conditions may readily be selected by one of ordinary skill in the art. Starting materials are commercially available or can be readily prepared by one of ordinary skill in the art using known methods. For all of the schemes and compounds described below $X^1$, $X^2$, A and $R^1$ are as described for a compound of Formula (I). The following are the definitions of symbols used throughout the Schemes and the Examples:

| | |
|---|---|
| AcOH or HOAc | Acetic acid |
| AIBN | Azobisisobutyronitrile |
| AlCl$_3$ | Aluminum chloride |
| Ar | Aryl |
| Bn | Benzyl |
| Boc | tert-butyloxycarbonyl |
| BOP | (Benzotriazol-1-yloxy)tris(dimethylamino)phosphonium hexafluorophosphate |
| Bu | Butyl |
| i-Bu | Isobutyl |
| t-Bu | tert-butyl |
| t-BuOH | tert-butanol |
| CH$_2$Cl$_2$ | dichloromethane |
| CH$_3$CN or ACN | Acetonitrile |
| CDCl$_3$ | deutero-chloroform |
| CHCl$_3$ | Chloroform |
| mCPBA or m-CPBA | meta-chloroperbenzoic acid |
| Cs$_2$CO$_3$ | cesium carbonate |
| DCM | dichloromethane |
| DEA | Diethylamine |
| DIC | diisopropylcarbodiimide |
| DIPEA or Hunig's base | diisopropylethylamine |
| DMSO | dimethyl sulfoxide |
| Dppp | (R)-(+)-1,2-bis(diphenylphosphino)propane |
| EDC | N-(3-dimthylaminopropyl)-N'-ethylcarbodiimide |
| Et$_3$N or TEA | Triethylamine |
| EtOAc | ethyl acetate |
| Et$_2$O | diethyl ether |
| Et | Ethyl |
| EtOH | Ethanol |
| HCl | hydrochloric acid |
| HOBt | 1-hydroxybenzotriazole |
| H$_2$SO$_4$ | sulfuric acid |
| K$_2$CO$_3$ | potassium carbonate |
| KOAc | potassium acetate |
| K$_3$PO$_4$ | potassium phosphate |
| LG | leaving group |
| LiOH | lithium hydroxide |
| MeOH | Methanol |
| MgSO$_4$ | magnesium sulfate |
| MsOH or MSA | methylsulfonic acid |
| NaCl | sodium chloride |
| NaH | sodium hydride |
| NaHCO$_3$ | sodium bicarbonate |
| Na$_2$CO$_3$ | sodium carbonate |
| NaOH | sodium hydroxide |
| Na$_2$SO$_3$ | sodium sulfite |
| Na$_2$SO$_4$ | sodium sulfate |
| NBS | N-bromo succinimide |
| NH$_3$ | Ammonia |
| NH$_4$Cl | ammonium chloride |
| NH$_4$OH | ammonium hydroxide |
| Pd(OAc)$_2$ | palladium(II) acetate |
| Pd/C | palladium on carbon |
| Pd(dppf)Cl$_2$ | [1,1'-bis(diphenylphosphino)-ferrocene]dichloropalladium(II) |
| Ph$_3$PCl$_2$ | triphenylphosphine dichloride |
| Ph | Phenyl |
| PG | protecting group |
| POCl$_3$ | phosphorus oxychloride |
| i-PrOH or IPA | Isopropanol |
| Pr | Propyl |
| i-Pr | Isopropyl |
| PyBrop | Bromo-tris-pyrrolidino phosphoniumhexafluorophosphate |
| SiO$_2$ | silica oxide |
| SnCl$_2$ | tin(II) chloride |
| TFA | trifluoroacetic acid |
| THF | Tetrahydrofuran |

Synthesis

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Wiley and Sons (1991)).

General Schemes

Scheme 1

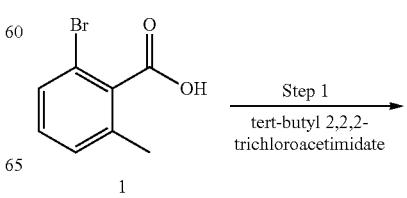

1

Step 1 tert-butyl 2,2,2-trichloroacetimidate

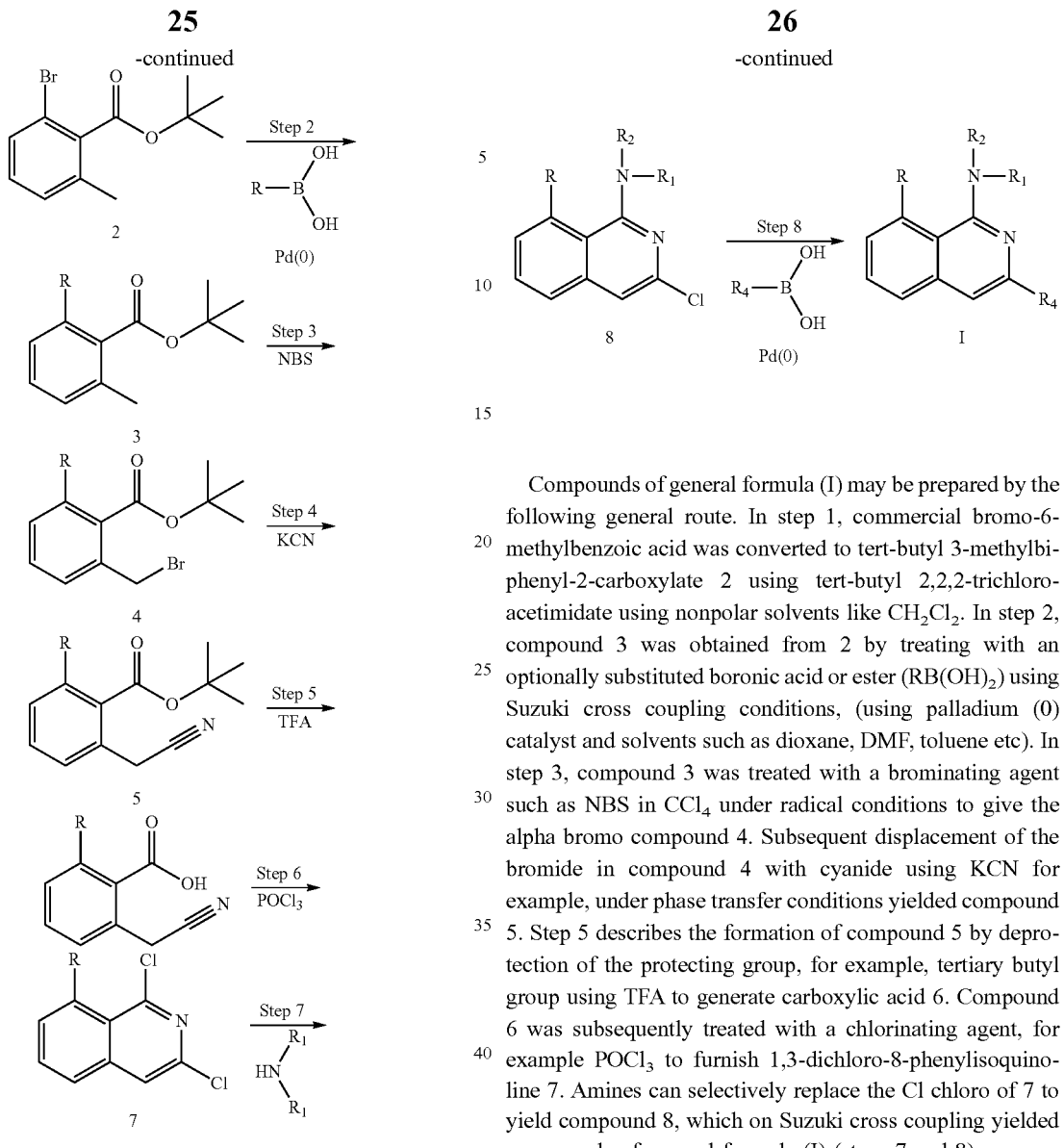

Compounds of general formula (I) may be prepared by the following general route. In step 1, commercial bromo-6-methylbenzoic acid was converted to tert-butyl 3-methylbiphenyl-2-carboxylate 2 using tert-butyl 2,2,2-trichloroacetimidate using nonpolar solvents like $CH_2Cl_2$. In step 2, compound 3 was obtained from 2 by treating with an optionally substituted boronic acid or ester ($RB(OH)_2$) using Suzuki cross coupling conditions, (using palladium (0) catalyst and solvents such as dioxane, DMF, toluene etc). In step 3, compound 3 was treated with a brominating agent such as NBS in $CCl_4$ under radical conditions to give the alpha bromo compound 4. Subsequent displacement of the bromide in compound 4 with cyanide using KCN for example, under phase transfer conditions yielded compound 5. Step 5 describes the formation of compound 5 by deprotection of the protecting group, for example, tertiary butyl group using TFA to generate carboxylic acid 6. Compound 6 was subsequently treated with a chlorinating agent, for example $POCl_3$ to furnish 1,3-dichloro-8-phenylisoquinoline 7. Amines can selectively replace the Cl chloro of 7 to yield compound 8, which on Suzuki cross coupling yielded compounds of general formula (I) (steps 7 and 8).

Scheme 2

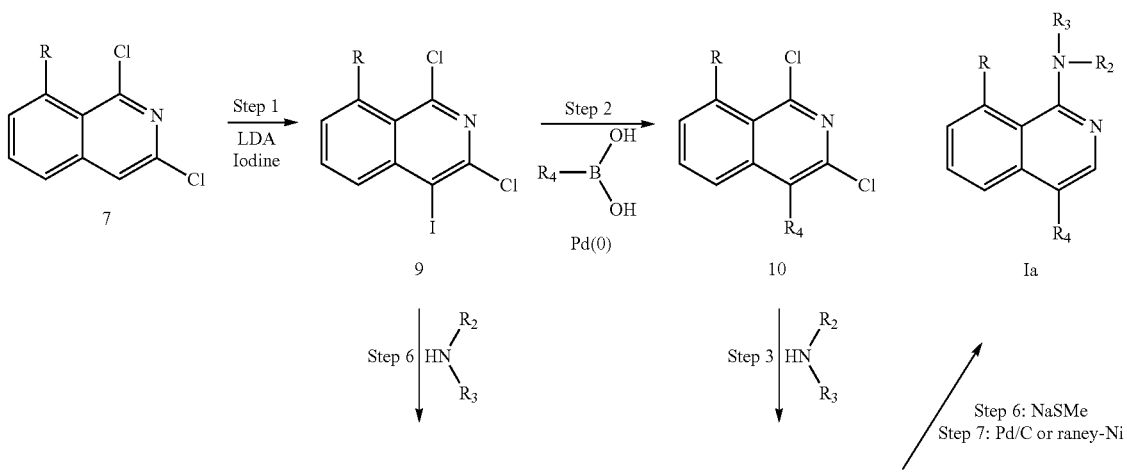

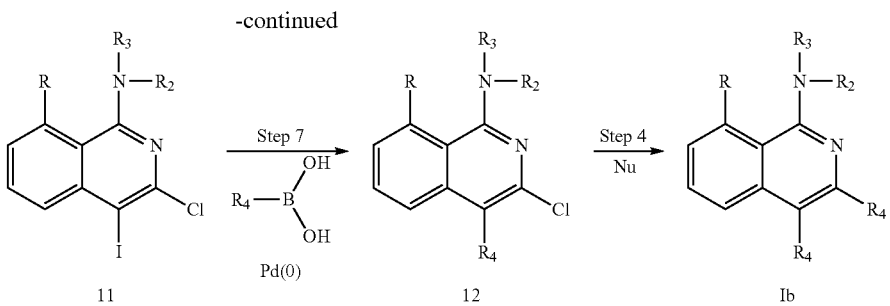

Alternatively, compounds of general formula (I) may be prepared by the general route shown in Scheme 2. 1,3-Dichloro-isoquinoline 7 was treated with a strong base, for example, LDA and treated subsequently with iodine to provide compound 9. In step 2, palladium mediated Suzuki cross coupling generated 10 (preferred solvents are DMF, dioxane, toluene etc.). Step 3 indicates that amines can selectively displace the Cl chloro of 10 to yield compound 12 using an additional base for example, DIPEA, Et$_3$N etc). Step 4 describes the cross coupling or displacement of a halogen at C3 to introduce different functional groups (e.g., alkyl group via corresponding boronic acids or esters or cyano group via nucleophilic replacement) to yield compounds of general formula (Ib). Alternatively, compound 12 can be obtained from 9 via step 6 and step 7 by following the protocol used in step 3 and step 2 respectively. Dehalogenation at C3 to generate compounds of general formula (Ia) was achieved via two step sequence. In step 6, a displaceable group such as thiomethyl was introduced via nucleophilic displacement; and in step 7 the thiomethyl intermediate was hydrogenated for example, using palladium on carbon or Raney-Ni under hydrogen pressure to generate compounds of the general formula (Ia).

Scheme 3

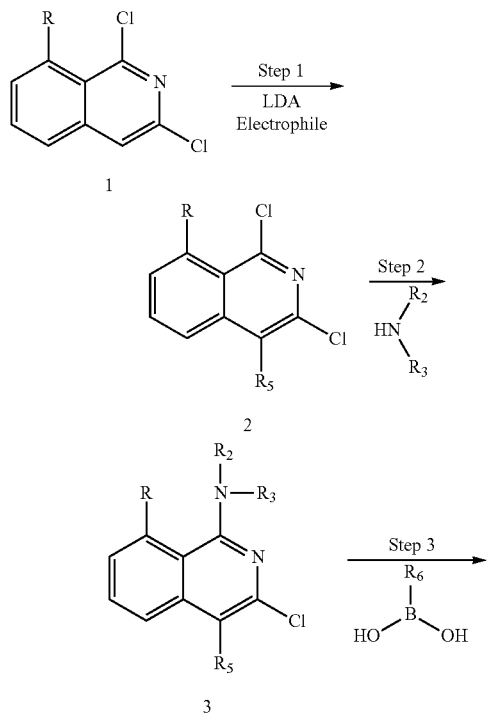

Alternatively, compounds of general formula (I) may be prepared by the general route shown in Scheme 3. In step 1 (Scheme 3) 1,3-dichloro-isoquinoline 7 was treated with a strong base for example LDA followed by an electrophile for example, methyltrifluoromethanesulfonate to provide compounds of general formula 2. Regioselective displacement of the Cl chloro of 2 by amines yielded compound 3 in the presence of base (for example, DIPEA, Et$_3$N, etc.) and solvent, for example, dioxane as shown in step 2. In step 3, palladium mediated Suzuki cross coupling with boronic acids or esters generates compounds of the general formula (I), (preferred solvents are DMF, dioxane, toluene etc.).

EXAMPLES

The following Examples illustrate, but are not intended to limit the preferred embodiments of the application or to limit the scope of the invention. Abbreviations and chemical symbols have their usual and customary meanings unless otherwise indicated. Unless otherwise indicated, compounds described have been prepared, isolated and characterized using the general schemes disclosed.

General Methods

The following methods were used in the working examples, except where noted otherwise.
Analytical HPLC and HPLC/MS Methods Employed in Characterization of Examples
Reverse phase analytical HPLC/MS was performed on Shimadzu LC10AS systems coupled with Waters ZMD Mass Spectrometers or Waters AQUITY® system coupled with a Waters MICROMASS® ZQ Mass Spectrometer.
Chiral analytical LC was performed on a Berger Analytical SFC instrument.
Condition B-1:
Column=XBridge Phenyl, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)

Start % B=10; Final % B=100
Gradient time=12 min; Stop time=23 min
Isocratic time=3 min
Flow Rate=1 mL/min; Wavelength=220 and 254 nm
Condition B-2:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=23 min
Isocratic time=3 min
Flow Rate=1 mL/min; Wavelength=220 and 254 nm
Condition B-3:
Column=YMC triart, 4.6×150 mm, 5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=15 min
Isocratic time=3 min
Flow Rate=1 mL/min; Wavelength=220 and 254 nm
Condition B-4:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=0; Final % B=50
Gradient time-1=15 min
Final % B=100
Gradient time-2=3 min
Isocratic time=5 min
Stop time=28 min
Flow Rate=1 mL/min; Wavelength=220 and 254 nm
Condition B-5:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=25 min; Stop time=30 min
Isocratic time=5 min
Flow Rate=1 mL/min; Wavelength=220 and 254 nm
Condition B-6:
Column=XBridge Phenyl, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=25 min; Stop time=30 min
Isocratic time=5 min
Flow Rate=1 mL/min; Wavelength=220 and 254 nm
Condition B-7:
Column=Eclipse XDB C18, 4.6×150 mm, 3.5 μm
Solvent A=20 mM $NH_4OAc$ in $H_2O$
Solvent B=$CH_3CN$
Start % B=10; Final % B=100
Gradient time=25 min; Stop time=36 min
Isocratic time=5 min
Flow Rate=1 mL/min; Wavelength=220 and 254 nm
Condition B-8:
Column=Eclipse XDB C18, 4.6×150 mm, 3.5 μm
Solvent A=20 mM $NH_4OAc$ in $H_2O$
Solvent B=$CH_3CN$
Start % B=10; Final % B=100
Gradient time=12 min; Stop time=26 min
Isocratic time=8 min
Flow Rate=1 mL/min; Wavelength=220 and 254 nm
Condition B-9:
Column=ZORBAX® SB C18, 4.6×50 mm, 5 μm
Solvent A=MeOH (10%)+0.1% TFA in $H_2O$ (90%)
Solvent B=MeOH (90%)+0.1% TFA in $H_2O$ (10%)
Start % B=0; Final % B=100
Gradient time=2 min; Stop time=3 min
Flow Rate=5 mL/min; Wavelength=220 nm
Condition B-10:
Column=PUROSPHER® STAR RP-18, 4.0×55 mm, 3 μm
Solvent A=$CH_3CN$ (10%)+20 mM $NH_4OAc$ in $H_2O$ (90%)
Solvent B=$CH_3CN$ (90%)+20 mM $NH_4OAc$ in $H_2O$ (10%)
Start % B=0; Final % B=100
Gradient time=2 min; Stop time=3 min
Isocratic time=0.5 min
Flow Rate=2.5 mL/min; Wavelength=220 nm
Condition B-11:
Column=PUROSPHER® STAR RP-18, 4.0×55 mm, 3 μm
Solvent A=$CH_3CN$ (10%)+20 mM $NH_4OAc$ in $H_2O$ (90%)
Solvent B=$CH_3CN$ (90%)+20 mM $NH_4OAc$ in $H_2O$ (10%)
Start % B=0; Final % B=100
Gradient time=1.8 min; Stop time=4 min
Isocratic time=1.5 min
Flow Rate=2.5 mL/min; Wavelength=220 nm
Condition B-12:
Column=Ascentis Express C18, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.4 min; Stop time=4 min
Isocratic time=1.6 min
Flow Rate=1 mL/min; Wavelength=220 nm
Condition B-13:
Column=Ascentis Express C8, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Isocratic time=1.7 min
Flow Rate=1 mL/min; Wavelength=220 nm
Condition B-14:
Column=Ascentis Express C8, 2.1×50 mm, 2.7 μm
Solvent A=$CH_3CN$ (10%)+10 mM $NH_4COOH$ in $H_2O$ (90%)
Solvent B=$CH_3CN$ (90%)+10 mM $NH_4COOH$ in $H_2O$ (10%)
Start % B=0; Final % B=100
Gradient time=1.6 min; Stop time=4 min
Isocratic time=1.6 min
Flow Rate=1 mL/min; Wavelength=220 nm
Condition B-15:
Column=Ascentis Express C18 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Isocratic time=1.7 min
Flow Rate=1 mL/min; Wavelength=220 nm
Condition B-16:
Column=Acquity BEH C18, 2.1×50 mm, 3 μm
Solvent A=$CH_3CN$ (5%)+5 mM $NH_4OAc$ in $H_2O$ (95%)
Solvent B=$CH_3CN$ (95%)+5 mM $NH_4OAc$ in $H_2O$ (5%)

Start % B=5; Final % B=95
Gradient time=1.1 min; Stop time=2.4 min
Isocratic time=0.6 min
Flow Rate=0.8 mL/min; Wavelength=220 nm
Condition B-17:
Column=ACE Excel 2 C18, 3.0×50 mm, 2.0 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=5; Final % B=100
Gradient time=1.8 min; Stop time=4 min
Isocratic time=0.8 min
Flow Rate=1.2 mL/min; Wavelength=220 nm
Condition B-18:
Column=BEH C18, 3.0×50 mm, 5.0 μm
Solvent A=$CH_3CN$ (5%)+10 mM $NH_4OAc$ in $H_2O$ (95%)
Solvent B=$CH_3CN$ (95%)+10 mM $NH_4OAc$ in $H_2O$ (5%)
Start % B=5; Final % B=100
Gradient time=1.8 min; Stop time=4 min
Isocratic time=1.4 min
Flow Rate=1.2 mL/min; Wavelength=220 nm
Condition B-19:
Column=XBridge C18, 2.1×50 mm, 2.5 μm
Solvent A=$CH_3CN$ (5%)+10 mM $NH_4HCO_3$ in $H_2O$ (95%)
Solvent B=$CH_3CN$ (95%)+10 mM $NH_4HCO_3$ in $H_2O$ (5%)
Start % B=0; Final % B=100
Gradient time=1.7 min; Stop time=4 min
Isocratic time=1.5 min
Flow Rate=1 mL/min; Wavelength=220 nm
Condition B-20:
Column=ZORBAX® SB-Aq, 4.6×50 mm, 3.5 μm
Solvent A=$CH_3CN$ (5%)+10 mM $NH_4COOH$ in $H_2O$ (95%)
Solvent B=$CH_3CN$ (95%)+10 mM $NH_4COOH$ in $H_2O$ (5%)
Start % B=5; Final % B=95
Gradient time=1.7 min; Stop time=4 min
Isocratic time=1.5 min
Flow Rate=1 mL/min; Wavelength=220 nm
Condition B-21:
Column=Ascentis Express C18, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.6 min; Stop time=4 min
Isocratic time=1.6 min
Flow Rate=1 mL/min; Wavelength=220 nm
Condition B-22:
Column=Ascentis Express C8, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Isocratic time=1.7 min
Flow Rate=1 mL/min; Wavelength=220 nm
Condition B-23:
Column=ZORBAX® SB C18, 4.6×50 mm, 3.5 μm
Solvent A=$CH_3CN$ (10%)+20 mM $NH_4OAc$ in $H_2O$ (90%)
Solvent B=$CH_3CN$ (90%)+20 mM $NH_4OAc$ in $H_2O$ (10%)
Start % B=0; Final % B=100
Gradient time=2.5 min; Stop time=3 min
Flow Rate=2.5 mL/min; Wavelength=220 nm
Condition B-24:
Column=ZORBAX® SB C18, 2.1×30 mm, 3.5 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=6; Final % B=100
Gradient time=1.5 min; Stop time=3 min
Isocratic time=1.7 min
Flow Rate=2.5 mL/min; Wavelength=220 nm
Condition B-25:
Column=ZORBAX® SB-Aq, 4.6×50 mm, 3.5 μm
Solvent A=$CH_3CN$ (10%)+0.1% HCOOH in $H_2O$ (90%)
Solvent B=$CH_3CN$ (90%)+0.1% HCOOH in $H_2O$ (10%)
Start % B=0; Final % B=20
Gradient time-1=1.5 min;
Final % B=95
Gradient time-2=2.5 min; Stop time=4 min
Flow Rate=1 mL/min; Wavelength=220 nm
Condition B-26:
Column=XBridge BEH C18, 2.1×50 mm, 2.5 μm
Solvent A=0.1% HCOOH in $H_2O$
Solvent B=0.07% HCOOH in $CH_3CN$
Start % B=10; Final % B=100
Gradient time=2.0 min; Stop time=4.0 min
Isocratic time=1 min
Flow Rate=1.2 mL/min; Wavelength=220 nm
Condition B-27:
Column=ZORBAX® SB C18, 2.1×30 mm, 3.5 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=6; Final % B=100
Gradient time=1.5 min; Stop time=3 min
Isocratic time=0.7 min
Flow Rate=1.5 mL/min; Wavelength=220 nm
Condition B-28:
Column=Ascentis Express C18, 4.6×50 mm, 2.7 μm
Solvent A=$CH_3CN$ (5%)+10 mM $NH_4COOH$ in $H_2O$ (95%)
Solvent B=$CH_3CN$ (95%)+10 mM $NH_4COOH$ in $H_2O$ (5%)
Start % B=0; Final % B=100
Gradient time=4 min; Stop time=5 min
Flow Rate=4 mL/min; Wavelength=220 nm
Condition B-29:
Column=XBridge C18, 2.1×50 mm, 2.5 μm
Solvent A=10 mM $NH_4HCO_3$
Solvent B=$CH_3CN$
Start % A=100; Final % B=100
Gradient time=1.7 min; Stop time=4 min
Isocratic time=1.5 min
Flow Rate=1 mL/min; Wavelength=220 nm
Condition B-30:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=18 min
Isocratic time=3 min
Flow Rate=1 mL/min; Wavelength=220 and 254 nm
Condition B-31:
Column=XBridge, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=18 min
Isocratic time=3 min
Flow Rate=1 mL/min; Wavelength=220 and 254 nm
Condition B-32:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100

Gradient time=12 min; Stop time=15 min
Isocratic time=3 min
Flow Rate=1 mL/min; Wavelength=220 and 254 nm
Condition B-33:
Column=ZORBAX®-SB-CN, 4.6×150 mm, 5.0 μm
Solvent A=CH$_3$CN (10%)+10 mM NH$_4$COOH in H$_2$O (90%)
Solvent B=CH$_3$CN (90%)+10 mM NH$_4$COOH in H$_2$O (10%)
Start % B=10; Final % B=100
Gradient time=20 min; Stop time=27 min
Isocratic time=5 min
Flow Rate=1 mL/min; Wavelength=220 and 254 nm
Condition B-34:
Column=Kinetex C-18, 2.1×50 mm, 2.6 μm
Solvent A=CH$_3$CN (2%)+0.1% NH$_4$COOH in H$_2$O (98%)
Solvent B=CH$_3$CN (98%)+0.1% NH$_4$COOH in H$_2$O (2%)
Start % B=0; Final % B=100
Gradient time=1.7 min; Stop time=4 min
Isocratic time=1.5 min
Flow Rate=1 mL/min; Wavelength=220 nm
Condition B-35:
Column=XBridge Phenyl, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=18 min
Isocratic time=3 min
Flow Rate=1 mL/min; Wavelength=220 and 254 nm
Condition B-36:
Column=Eclipse XDB C18, 4.6×150 mm, 3.5 μm
Solvent A=10 mM NH$_4$OAc in H$_2$O
Solvent B=CH$_3$CN
Start % B=10; Final % B=100
Gradient time=12 min; Stop time=17 min
Isocratic time=3 min
Flow Rate=1 mL/min; Wavelength=220 and 254 nm
Condition B-37:
Column=ZORBAX® SB C18, 4.6×50 mm, 3.5 μm
Solvent A=CH$_3$CN (10%)+20 mM NH$_4$OAc in H$_2$O (90%)
Solvent B=CH$_3$CN (90%)+20 mM NH$_4$OAc in H$_2$O (10%)
Start % B=10; Final % B=100
Gradient time=2.0 min; Stop time=3 min
Flow Rate=2.5 mL/min; Wavelength=220 nm
Condition B-38:
Column=Ascentis Express C18, 5×2.1 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Flow Rate=1 mL/min; Wave length=220 nm
Condition B-39:
Column=Ascentis Express C18, 5×2.1 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=1.7 min
Flow Rate=1 mL/min; Wavelength=220 nm
Condition B-40:
Column=Acquity BEH C18, 2.1×50 mm, 1.7 μm
Solvent A=Buffer: CH$_3$CN (95:5)
Solvent B=Buffer: CH$_3$CN (5:95)
Buffer=10 mM NH$_4$OAc in H$_2$O (pH 5, adjusted with HCOOH)
Start % B=5; Final % B=95
Gradient time=1.1 min; Stop time=2.4 min
Isocratic time=0.6 min
Flow Rate=0.8 mL/min; Wave length=220 nm
Condition B-41:
Column: Acquity BEH C18, 2.1×50 mm, 1.7 μm
Solvent A=0.1% TFA in H$_2$O
Solvent B=0.1% TFA in CH$_3$CN
Start % B=2; Final % B=98
Gradient time=1 min; Stop time=2.2 min
Isocratic time=0.6 min
Flow Rate=0.8 mL/min; Wave length=220 nm
Condition B-42:
Column=ZORBAX® SB C18, 4.6×50 mm, 3.5 μm
Solvent A=MeOH (10%)+0.1% TFA in H$_2$O (90%)
Solvent B=MeOH (90%)+0.1% TFA in H$_2$O (10%)
Start % B=10; Final % B=100
Gradient time=1.8 min; Stop time=3 min
Isocratic time=0.5 min
Flow Rate=4 mL/min; Wave length=220 nm
Condition B-43:
Column=XBridge BEH C18, 2.1×50 mm, 2.5 μm
Solvent A=CH$_3$CN (2%)+0.1% TFA in H$_2$O (98%)
Solvent B=CH$_3$CN (98%)+0.1% TFA in H$_2$O (2%)
Start % B=3; Final % B=100
Gradient time=1.3 min; Stop time=3 min
Isocratic time=0.5 min
Flow Rate=11 mL/min; Wave length=220 nm
Condition B-44:
Column=POROSHELL® 120, 50×3.0 mm, 2.7 μm
Solvent A=Buffer: CH$_3$CN (90:10)
Solvent B=Buffer: CH$_3$CN (10:90)
Buffer=10 mM NH$_4$OAc in H$_2$O (pH 5, adjusted with HCOOH)
Start % B=5; Final % B=100
Gradient time=1.5 min; Stop time=3 min
Isocratic time=0.7 min
Flow Rate=1.5 mL/min; Wave length=220 nm
Condition B-45:
Column=Ascentis Express C18, 5×2.1 mm, 2.7 μm
Solvent A=10 mM NH$_4$HCO$_3$
Solvent B=CH$_3$CN
Start % B=0; Final % B=100
Gradient time=1.7 min; Stop time=4 min
Isocratic time=1.5 min
Flow Rate=1 mL/min; Wave length=220 nm
Condition B-46:
Column=Ascentis Express C18, 5×2.1 mm, 2.7 μm
Solvent A=0.1% HCOOH in H$_2$O
Solvent B=0.07% HCOOH in CH$_3$CN
Start % B=10; Final % B=100
Gradient time=2 min; Stop time=4 min
Isocratic time=1 min
Flow Rate=1.2 mL/min; Wave length=220 nm
Condition B-47:
Column=XBridge BEH C18, 2.1×50 mm, 2.5 μm
Solvent A=CH$_3$CN (2%)+0.1% TFA in H$_2$O (98%)
Solvent B=CH$_3$CN (98%)+0.05% TFA in H$_2$O (2%)
Start % B=2; Final % B=100
Gradient time=2.6 min; Stop time=4.1 min
Isocratic time=0.6 min
Flow Rate=1.2 mL/min; Wave length=220 nm
Condition B-48:
Column=Inertsil 3 V ODS C18, 20×250 mm, 5 μm
Solvent A=10 mM NH$_4$OAc in H$_2$O
Solvent B=CH$_3$CN
Start % B=70; Final % B=90

Gradient time=16 min; Stop time=30 min
Isocratic time=9 min
Flow Rate=16 mL/min; Wave length=220 nm
Condition B-49:
Column=XBridge Phenyl, 4.6×150 mm, 3.5 μm
Solvent A=10 mM NH$_4$OAc in H$_2$O (pH 5.0)
Solvent B=Methanol
Buffer: 10 mM NH$_4$OAc in H$_2$O
Start % B=20; Final % B=70
Gradient time-1=8 min;
Start % B=70; Final % B=100
Gradient time-2=4 min; Stop time=20 min
Isocratic time=3 min
Flow Rate=1 mL/min; Wave length=220 nm
Condition B-50:
Column=CHIRALCEL® OJH, 250×4.6 mm, 5 μm
Solvent A=n-Hexane
Solvent B=Ethanol
Isocratic=A: B (50:50)
Flow=1 mL/min; Wave length=220 nm
Condition B-51:
Column=SunFire C18, 20×250 mm, 5.0 μm
Solvent A=10 mM NH$_4$OAc in H$_2$O (pH 4.6, adjusted with AcOH)
Solvent B=CH$_3$CN
Start % B=20; Final % B=90
Gradient time=15 min; Stop time=35 min
Flow=15 mL/min; Wave length=220 nm
Condition B-52:
Column=CHIRALCEL® OJH, 250×4.6 mm, 5 μm
Solvent A=CO$_2$
Solvent B=0.3% DEA in MeOH
Isocratic=A: B (40:60)
Flow=3 mL/min; Wave length=220 nm
Condition B-53:
Column=Inertsil ods, 20×250 mm, 5.0 μm
Solvent A=10 mM NH$_4$OAc in H$_2$O
Solvent B=CH$_3$CN
Start % B=15; Final % B=95
Gradient time=14 min; Stop time=25 min
Flow=15 mL/min; Wave length=220 nm
Condition B-54:
Column=Atlantis C18, 19×250 mm, 5.0 μm
Solvent A=10 mM NH$_4$OAc in H$_2$O (pH 4.6, adjusted with AcOH)
Solvent B=CH$_3$CN
Start % B=10; Final % B=80
Gradient time=20 min; Stop time=35 min
Flow=17 mL/min; Wave length=220 nm
Condition B-55:
Column=SunFire C18, 4.6×150 mm, 3.5 μm
Solvent A=Buffer: CH$_3$CN (95:5)
Solvent B=Buffer: CH$_3$CN (5:95)
Buffer=0.05% TFA in H$_2$O
Start % B=10; Final % B=100
Gradient time=25 min; Stop time=30 min
Isocratic time=5 min
Flow=1 mL/min; Wave length=220 nm
Condition B-56:
Column=XBridge BEH C18, 2.1×50 mm, 2.5 μm
Solvent A=1% HCOOH in H$_2$O
Solvent B=CH$_3$CN
Start % B=5; Final % B=100
Gradient time=2.5 min; Stop time=4 min
Flow=1 mL/min; Wave length=220 nm
Condition B-57:
Column=PHENOMENEX® C18, 19×250 mm, 5 μm
Solvent A=10 mM NH$_4$OAc in H$_2$O (pH 4.5, adjusted with AcOH)
Solvent B=CH$_3$CN
Start % B=6; Final % B=60
Gradient time=20 min; Stop time=35 min
Flow=16 mL/min; Wave length=220 nm
Condition B-58:
Column=SunFire C18, 20×250 mm, 5 μm
Solvent A=10 mM NH$_4$OAc in H$_2$O (pH 4.5, adjusted with AcOH)
Solvent B=CH$_3$CN
Start % B=50; Final % B=90
Gradient time=10 min; Stop time=20 min
Isocratic time=5 min
Flow=16 mL/min; Wave length=220 nm
Condition B-59:
Column=YMC C18, 150×20 mm, 5 μm
Solvent A=10 mM NH$_4$OAc in H$_2$O (pH 4.6, adjusted with AcOH)
Solvent B=CH$_3$CN
Start % B=30; Final % B=70
Gradient time-1=10 min;
Start % B=70; Final % B=100
Gradient time-2=7.1 min; Stop time=20 min
Isocratic time=5 min
Flow=15 mL/min; Wave length=220 nm
Condition B-60:
Column=SYMMETRY® C18, 21.2×250 mm, 7 μm
Solvent A=10 mM NH$_4$OAc in H$_2$O (pH 4.5, adjusted with AcOH)
Solvent B=CH$_3$CN
Start % B=30; Final % B=65
Gradient time=5 min; Stop time=25 min
Flow=16 mL/min; Wave length=220 nm
Condition B-61:
Column=Luna C18, 19×250 mm, 7 μm
Solvent A=10 mM NH$_4$OAc in H$_2$O
Solvent B=CH$_3$CN
Start % B=30; Final % B=100
Gradient time=8 min; Stop time=20 min
Isocratic time=7 min
Flow=16 mL/min; Wave length=220 nm
Condition B-62:
Column=SYMMETRY® C18, 300×19 mm, 7 μm
Solvent A=10 mM NH$_4$OAc in H$_2$O
Solvent B=CH$_3$CN
Start % B=20; Final % B=60
Gradient time=10 min; Stop time=24 min
Flow=16 mL/min; Wave length=220 nm
Condition B-63:
Column=XBridge Phenyl, 4.6×150 mm, 3.5 μm
Solvent A=10 mM NH$_4$HCO$_3$ (pH 9.5, adjusted with dilute NH$_3$)
Solvent B=Methanol
Start % B=10; Final % B=100
Gradient time=25 min; Stop time=30 min
Isocratic time=5 min
Flow=1 mL/min; Wave length=220 nm
Condition B-64:
Column=XTERRA® C18, 250×19 mm, 10 μm
Solvent A=10 mM NH$_4$OAc in H$_2$O (pH 4.5, adjusted with AcOH)
Solvent B=CH$_3$CN
Start % B=30; Final % B=50
Gradient time-1=10 min;
Isocratic time=7 min
Start % B=50; Final % B=100

Gradient time-2=1 min; Stop time=22 min
Flow=16 mL/min; Wave length=220 nm
Condition B-65:
Column=CHIRALPAK® OJH, 19×250 mm, 5 μm
Solvent A=n-Hexane
Solvent B=EtOH
Isocratic=A: B (80:20)
Flow=15 mL/min; Wave length=220 nm
Condition B-66:
Column=YMC triat C18, 150×19 mm, 5 μm
Solvent A=10 mM NH₄OAc in H₂O
Solvent B=CH₃CN
Start % B=60; Final % B=90
Gradient time=10 min; Stop time=19 min
Flow=15 mL/min; Wave length=220 nm
Condition B-67:
Column=Atlantis DC18, 250×19 mm, 10 μm
Solvent A=10 mM NH₄OAc in H₂O
Solvent B=CH₃CN
Start % B=20; Final % B=75
Gradient time-1=10 min;
Isocratic time=4 min
Start % B=75; Final % B=100
Gradient time=0.2 min; Stop time=23 min
Isocratic time=3.8 min
Flow=15 mL/min; Wave length=220 nm
Condition B-68:
Column=SYMMETRY® C18, 250×19 mm, 7 μm
Solvent A=10 mM NH₄OAc in H₂O (pH 4.5, adjusted with AcOH)
Solvent B=CH₃CN
Start % B=50; Final % B=90
Gradient time=10 min; Stop time=19 min
Isocratic time=5 min
Flow=17 mL/min; Wave length=220 nm
Condition B-69:
Column=SunFire C18, 19×150 mm, 5 μm
Solvent A=10 mM NH₄OAc in H₂O (pH 4.5, adjusted with AcOH)
Solvent B=CH₃CN
Isocratic=A: B (20:80)
Flow=16 mL/min; Wave length=220 nm
Condition B-70:
Column=Atlantis C18, 19×250 mm, 5 μm
Solvent A=10 mM NH₄OAc in H₂O (pH 4.5, adjusted with AcOH)
Solvent B=CH₃CN
Isocratic=A: B (30:70)
Flow=16 mL/min; Wave length=220 nm
Condition B-71:
Column=XSelect C18, 19×150 mm, 5 μm
Solvent A=10 mM NH₄OAc in H₂O
Solvent B=CH₃CN
Start % B=30; Final % B=70
Gradient time-1=12 min;
Start % B=70; Final % B=100
Gradient time=3 min; Stop time=19 min
Flow=16 mL/min; Wave length=220 nm
Condition B-72:
Column=XBridge C18, 19×150 mm, 5 μm
Solvent A=10 mM NH₄OAc in H₂O (pH 4.5, adjusted with AcOH)
Solvent B=CH₃CN
Start % B=30; Final % B=70
Gradient time-1=8 min;
Start % B=70; Final % B=100
Gradient time=7 min; Stop time=19 min Flow=17 mL/min; Wave length=220 nm
NMR Employed in Characterization of Examples ¹H NMR spectra were obtained with Bruker or JEOL® Fourier transform spectrometers operating at frequencies as follows: ¹H NMR: 400 MHz (Bruker or JEOL®) or 500 MHz (JEOL®). ¹³C NMR: 100 MHz (Bruker or JEOL®). Spectra data are reported in the format: chemical shift (multiplicity, coupling constants, and number of hydrogens). Chemical shifts are specified in ppm downfield of a tetramethylsilane internal standard (δ units, tetramethylsilane=0 ppm) and/or referenced to solvent peaks, which in ¹H NMR spectra appear at 2.49 ppm for CD₂HSOCD₃, 3.30 ppm for CD₂HOD, and 7.24 ppm for CHCl₃, and which in ¹³C NMR spectra appear at 39.7 ppm for CD₃SOCD₃, 49.0 ppm for CD₃OD, and 77.0 ppm for CDCl₃. All ¹³C NMR spectra were proton decoupled.

Example 1

5-(8-Phenyl-1-(pyridin-2-ylmethylamino)isoquinolin-3-yl)pyridine-3-sulfonamide

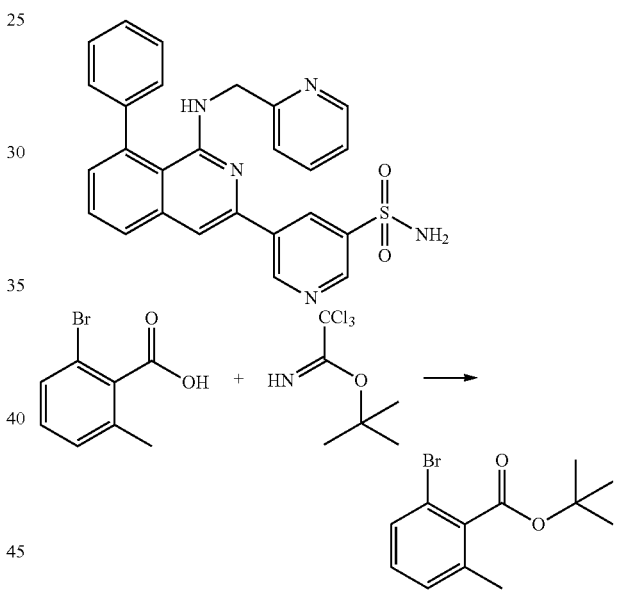

To a solution of 2-bromo-6-methylbenzoic acid (10.00 g, 46.50 mmol) in DCM (150 mL) was added tert-butyl 2,2,2-trichloroacetimidate (16.66 mL, 93.00 mmol) at room temperature. The contents were stirred at room temperature for 12 h. The reaction mixture was concentrated under reduced pressure and the resulting residue was purified by silica gel column chromatography using CombiFlash (40 g REDISEP® column) using 5% ethyl acetate in hexane as an eluent to yield tert-butyl 2-bromo-6-methylbenzoate (12 g, 95%). ¹H NMR (400 MHz, DMSO-d₆) δ ppm: 1.56 (s, 9H), 2.29 (s, 3H), 7.24-7.30 (m, 2H), 7.47-7.49 (m, 1H).

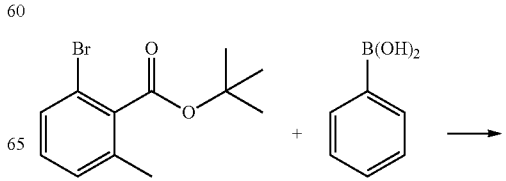

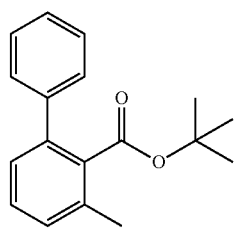
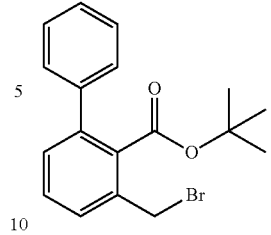

To a stirred solution of tert-butyl 2-bromo-6-methylbenzoate (12.00 g, 44.30 mmol) in 1,4-dioxane/water (120/30 mL) was added phenylboronic acid (6.48 g, 53.1 mmol) and potassium carbonate (18.35 g, 13.00 mmol). The contents were purged with nitrogen for 30 min and bis(triphenylphosphine)palladium(II) chloride (1.55 g, 2.21 mmol) was added. The reaction mixture was heated at 100° C. in a sealed tube for 12 h and allowed to cool room temperature. The reaction mixture was filtered through a pad of CELITE®. The filtrate was evaporated under reduced pressure to yield a brown residue.

The residue was dissolved in ethyl acetate and washed with water (2×100 mL). The organic layer was separated, dried over anhydrous sodium sulfate, filtered and evaporated and the residue was purified by silica gel column chromatography using CombiFlash (40 g REDISEP® column) with 5% ethyl acetate in hexane as an eluent to yield tert-butyl 3-methyl-[1,1'-biphenyl]-2-carboxylate (11 g, 93%). $^1$H NMR (400 MHz, DMSO-$d_6$) δ ppm: 1.25 (s, 9H), 2.33 (s, 3H), 7.17-7.27 (m, 1H), 7.28-7.32 (m, 1H), 7.32-7.34 (m, 2H), 7.37-7.44 (m, 4H).

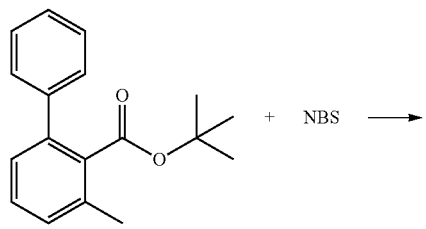
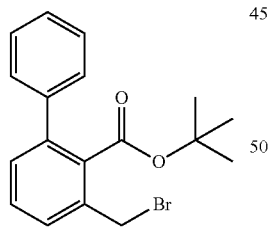

To a solution of tert-butyl 3-methyl-[1,1'-biphenyl]-2-carboxylate (11.00 g, 41.00 mmol) in $CCl_4$ (220 mL) was added AIBN (1.35 g, 8.20 mmol) followed by N-bromo succinimide (8.03 g, 45.1 mmol). The reaction mixture was stirred at 80° C. for 12 h and allowed to cool room temperature and concentrated under reduced pressure to give a brown residue. The residue was purified by silica gel column chromatography (40 g REDISEP® column) with 20% ethyl acetate in hexane as an eluent to yield tert-butyl 3-(bromomethyl)-[1,1'-biphenyl]-2-carboxylate (13 g, 91%). $^1$H NMR (400 MHz, DMSO-$d_6$) δ ppm: 1.25 (s, 9H), 4.79 (s, 2H), 7.32-7.54 (m, 8H).

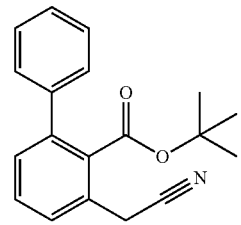

To a stirred solution of tert-butyl 3-(bromomethyl)-[1,1'-biphenyl]-2-carboxylate (13.00 g, 37.40 mmol) in dichloromethane (100 mL) was added tetrabutylammonium bromide (1.81 g, 5.60 mmol) followed by water (100 mL) and potassium cyanide (7.31 g, 112 mmol). The resulting solution was allowed to stir at room temperature 12 h. The reaction mixture was diluted with saturated sodium bicarbonate solution and extracted with dichloromethane (3×30 mL). The combined organic extracts were dried over anhydrous sodium sulfate and evaporated under reduced pressure and the residue was purified by silica gel column chromatography using CombiFlash (40 g REDISEP® column) with 10% ethyl acetate in hexane as an eluent to yield tert-butyl 3-(cyanomethyl)-[1,1'-biphenyl]-2-carboxylate (8.0 g, 73%). $^1$H NMR (400 MHz, DMSO-$d_6$) δ ppm: 1.24 (s, 9H), 4.03 (s, 2H), 7.31-7.32 (m, 2H), 7.33-7.42 (m, 4H), 7.43-7.51 (m, 2H).

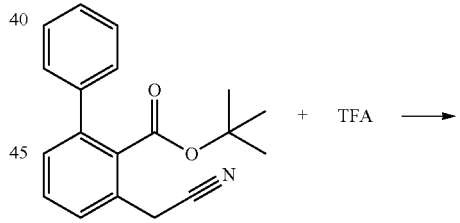
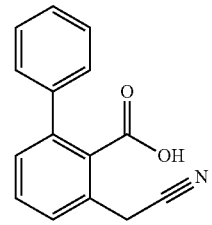

To a solution of tert-butyl 3-(cyanomethyl)-[1,1'-biphenyl]-2-carboxylate (2.30 g, 7.84 mmol) in methanol (25 mL) and water (25 mL) was added concentrated HCl (6.00 mL, 197 mmol) at 0° C. The resulting solution was allowed to stir for 6 h at 70° C. The reaction mixture was diluted with cold water (100 mL) and extracted with ethyl acetate (3×30 mL). The combined organic extracts were dried over anhydrous sodium sulfate and evaporated under reduced pressure to give 3-(cyanomethyl)biphenyl-2-carboxylic acid which was used without further purification. LCMS Method B-10:

retention time 1.07 min, [M−1]=236.20. $^1$H NMR (400 MHz, DMSO-$d_6$) δ ppm: 4.06 (s, 2H), 7.38-7.45 (m, 7H), 7.53-7.57 (m, 1H).

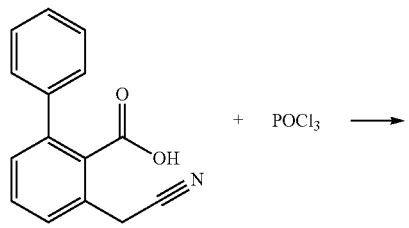

To a solution of 3-(cyanomethyl)-[1,1'-biphenyl]-2-carboxylic acid (2.00 g, 8.43 mmol) in POCl$_3$ (25 mL) was added PCl$_5$ (4.39 g, 21.1 mmol) at room temperature. The reaction mixture was heated at 70° C. for 14 h. The reaction mixture was allowed to cool and evaporated under reduced pressure to give a residue. The residue was diluted with saturated sodium bicarbonate solution (200 mL) and extracted with dichloromethane (3×30 mL). The combined organic extracts were dried over sodium sulfate and evaporated under reduced pressure to give a residue which was purified by silica gel column chromatography using CombiFlash (24 g REDISEP® column) with 20% ethyl acetate in hexane as an eluent to yield 1,3-dichloro-8-phenylisoquinoline (0.40 g, 17%) as a yellow solid. LCMS Method B-10: retention time 2.18 min, [M+1]=274.00. $^1$H NMR (400 MHz, DMSO-$d_6$) δ ppm: 7.36-7.38 (m, 2H), 7.44-7.47 (m, 3H), 7.60 (dd, J=7.2 Hz, J=7.2 Hz, 1H), 7.90-7.94 (m, 1H), 8.10-8.13 (m, 1H), 8.24 (s, 1H).

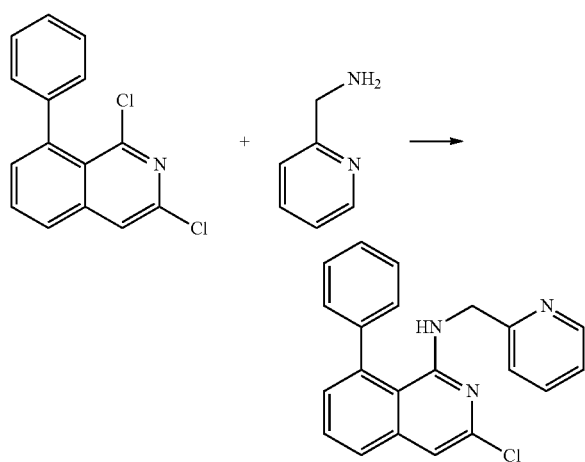

To a solution of 1,3-dichloro-8-phenylisoquinoline (0.40 g, 1.5 mmol) in DMF (10 mL) was added 2-(aminomethyl)pyridine (0.30 mL, 2.9 mmol) followed by DIPEA (0.51 mL, 2.9 mmol) at room temperature. The resulting reaction mixture was heated at 100° C. for 12 h in a sealed tube. The reaction mixture was diluted with iced water (150 mL) and extracted with ethyl acetate (2×50 mL). The combined organic layer was dried over anhydrous sodium sulfate, filtered and evaporated under reduced pressure to give a residue which was purified by silica gel column chromatography using CombiFlash (12 g REDISEP® column) with 10% ethyl acetate in hexane as an eluent to yield 3-chloro-8-phenyl-N-(pyridin-2-ylmethyl)isoquinolin-1-amine (0.23 g, 34%). LCMS Method B-10: retention time 2.33 min, [M+1]=346.00. $^1$H NMR (400 MHz, DMSO-$d_6$) δ ppm:4.48 (d, J=4.4 Hz, 2H) 6.43 (t, J=4.0 Hz, 1H), 7.17 (s, 1H), 7.19-26 (m, 3H), 7.43-7.52 (m, 5H), 7.65-7.71 (m, 2H) 7.77 (dd, J=8.0 Hz, J=8.4 Hz, 1H), 8.20 (d, J=4.4 Hz, 1H).

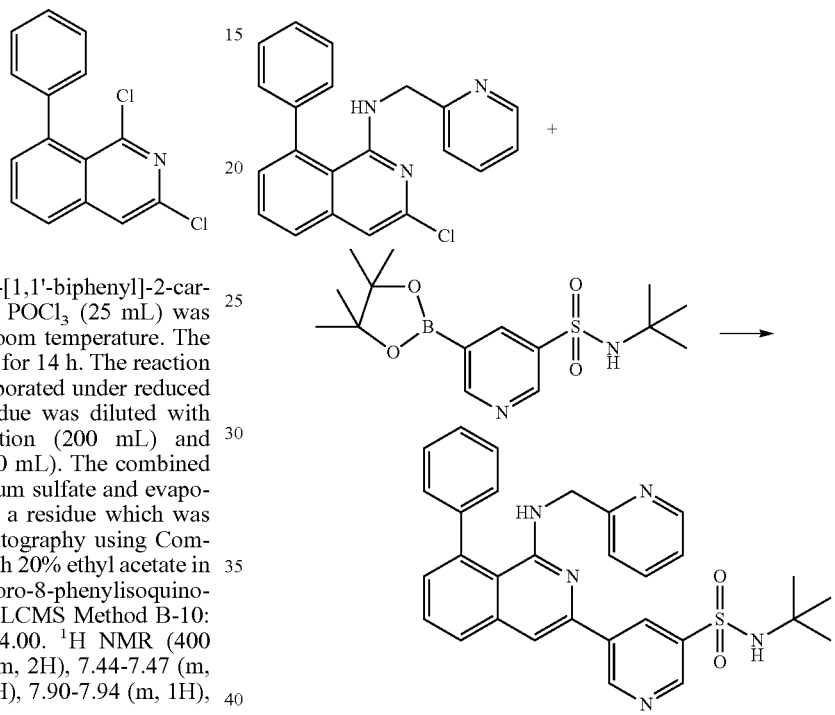

To a solution of 3-chloro-8-phenyl-N-(pyridin-2-ylmethyl)isoquinolin-1-amine (0.23 g, 0.66 mmol) in 1,4-dioxane (15 mL) and water (4 mL) was added N-(tert-butyl)-5-(4,4,5,5-tetramethyl-1,3,2-dioxaborolan-2-yl)pyridine-3-sulfonamide (prepared according to WO 2011/028741) (0.34 g, 0.99 mmol) and potassium carbonate (0.28 g, 2.0 mmol). The reaction mixture was purged with N$_2$ for 10 min. 1,1'-Bis(diphenylphosphino)ferrocene-palladium(II)dichloride dichloromethane complex (0.03 g, 0.03 mmol) was added to the reaction mixture and heated at 100° C. in a sealed tube for 12 h. The reaction mixture was allowed to cool and filtered through a pad of CELITE®. The filtrate was concentrated under reduced pressure to give a residue which was suspended in water (100 mL) and extracted with ethyl acetate (3×100 mL). The combined organic layer was dried over anhydrous sodium sulfate and evaporated under reduced pressure to give a residue which was purified by silica gel column chromatography using CombiFlash (12 g REDISEP® column) with 10% ethyl acetate in hexane as an eluent to yield N-(tert-butyl)-5-(8-phenyl-1-((pyridin-2-ylmethyl)amino)isoquinolin-3-yl)pyridine-3-sulfonamide (0.20 g, 47%). LCMS Method B-10: retention time 2.10 min, [M+1]=524.20. $^1$H NMR (400 MHz, DMSO-$d_6$) δ ppm:1.17 (s, 9H), 4.65 (d, J=4.4 Hz, 2H), 6.18 (t, J=4 Hz, 1H), 7.19-7.23 (m, 2H), 7.31 (dd, J=6.8 Hz, J=7.2 Hz, 1H), 7.48-7.53 (m, 5H), 7.66-7.73 (m, 2H), 7.90-7.93 (m, 2H), 7.95 (s, 1H), 8.27-8.31 (m, 1H) 8.89 (t, J=2 Hz, 1H), 8.95 (d, J=2 Hz, 1H), 9.52 (d, J=2 Hz, 1H).

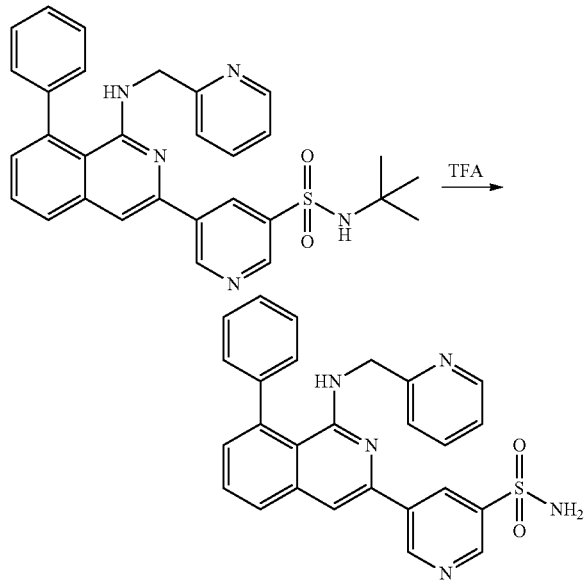

N-(tert-Butyl)-5-(8-phenyl-1-((pyridin-2-ylmethyl) amino)isoquinolin-3-yl)pyridine-3-sulfonamide (0.20 g, 0.38 mmol) was dissolved in TFA (15 mL) and stirred at room temperature for 12 h. TFA was removed under reduced pressure and the reaction mixture was diluted with saturated sodium bicarbonate (100 mL) and extracted with ethyl acetate (3×30 mL). The combined organic layer was dried over sodium sulfate and evaporated under reduced pressure to give a residue which was purified by silica gel column chromatography using CombiFlash (12 g REDISEP® column) with 3% methanol in chloroform as an eluent to yield 5-(8-phenyl-1-((pyridin-2-ylmethyl)amino)isoquinolin-3-yl)pyridine-3-sulfonamide (0.060 g, 34%) as a yellow solid. LCMS Method B-10: retention time 1.91 min, [M+1]= 468.20. HPLC Method B-2: retention time 7.20 min, Purity 98%. $^1$H NMR (400 MHz, DMSO-$d_6$) δ ppm: 4.65 (d, J=4 Hz, 2H), 6.18 (t, J=4 Hz, 1H), 7.30-7.32 (m, 3H), 7.48-7.52 (m, 5H), 7.66-7.73 (m, 4H), 7.90 (s, 1H), 7.93 (dd, J=8.0 Hz, J=0.8 Hz, 1H), 8.28 (dd, J=4.8 Hz, J=0.4 Hz, 1H), 8.88 (t, J=2 Hz, 1H), 8.97 (d, J=2 Hz, 1H), 9.54 (d, J=2 Hz, 1H).

Example 2

3-(5-Aminopyridin-3-yl)-8-phenyl-N-(pyridin-2-ylmethyl)isoquinolin-1-amine

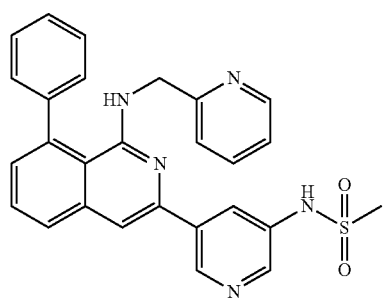

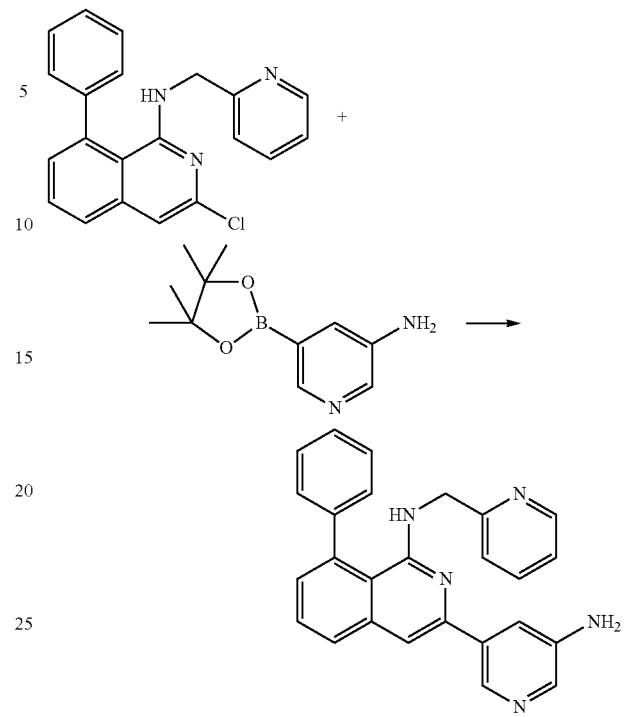

3-Chloro-8-phenyl-N-(pyridin-2-ylmethyl)isoquinolin-1-amine (prepared as described in Example 1) (0.10 g, 0.29 mmol) was converted to 3-(5-aminopyridin-3-yl)-8-phenyl-N-(pyridin-2-ylmethyl)isoquinolin-1-amine via Suzuki cross coupling using the conditions described in Example 1. Following reagents are utilized for this reaction: 5-(4,4,5,5-tetramethyl-1,3,2-dioxaborolan-2-yl)pyridin-3-amine (0.090 g, 0.43 mmol), potassium carbonate (0.12 g, 0.87 mmol) and 1,1'-bis(diphenylphosphino)ferrocene-palladium (II)dichloride dichloromethane complex (0.01 g, 0.01 mmol). The resulting residue was purified by preparative HPLC (Condition B-69 as described in general methods) to yield 3-(5-aminopyridin-3-yl)-8-phenyl-N-(pyridin-2-ylmethyl)isoquinolin-1-amine (0.030 g, 30%). LCMS Method B-10: retention time 1.95 min, [M+1]=404.20. HPLC Method B-2: retention time 5.69 min, Purity 99.34%. $^1$H NMR (400 MHz, DMSO-$d_6$) δ ppm: 4.64 (d, J=4 Hz, 2H), 5.36 (s, 2H), 6.03 (t, J=4.4 Hz, 1H), 7.19-7.24 (m, 3H), 7.45-7.51 (m, 5H), 7.62-7.70 (m, 4H), 7.86 (dd, J=8.4 Hz, J=1.2 Hz, 1H), 7.94 (d, J=2.4 Hz, 1H), 8.28 (dd, J=5.2 Hz, J=1.6 Hz, 1H), 8.51 (d, J=2 Hz, 1H).

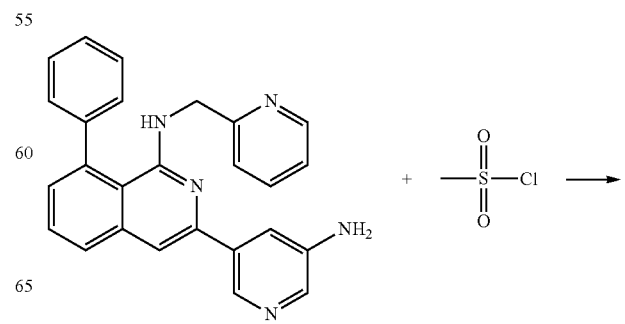

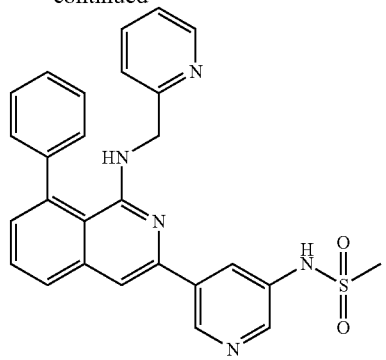

To a solution of 3-(5-aminopyridin-3-yl)-8-phenyl-N-(pyridin-2-ylmethyl)isoquinolin-1-amine (0.15 g, 0.37 mmol) in CH$_2$Cl$_2$ (15 mL) was added pyridine (0.06 mL, 0.7 mmol) followed by methanesulfonyl chloride (0.03 mL, 0.4 mmol) at room temperature. The reaction mixture was stirred for 12 h and was diluted with water (100 mL). The aqueous mixture was extracted into CH$_2$Cl$_2$ (2×50 mL). The combined organic layer was dried over anhydrous sodium sulfate, filtered and evaporated under reduced pressure to give a residue which was purified by preparative HPLC (Condition B-69 as described in general methods) to yield N-(5-(8-phenyl-1-((pyridin-2-ylmethyl)amino)isoquinolin-3-yl)pyridin-3-yl)methanesulfonamide (0.030 g, 20%). LCMS Method B-13: retention time 2.01 min, [M−1]= 480.00. HPLC Method B-2: retention time 7.09 min, Purity 95.27%. $^1$H NMR (400 MHz, DMSO-d$_6$) δ ppm: 3.11 (s, 3H), 4.64 (d, J=4 Hz, 2H), 6.09 (t, J=4.4 Hz, 1H), 7.19-7.26 (m, 3H), 7.47-7.52 (m, 5H), 7.66-7.71 (m, 2H), 7.77 (s, 1H), 7.92 (dd, J=8 Hz, J=0.8 Hz, 1H), 8.27 (m, 1H), 8.39 (t, J=2.4 Hz, 1H), 8.45 (d, J=2.4 Hz, 1H), 9.09 (d, J=2 Hz, 1H), 10.09 (s, 1H).

Example 3

N-(5-(8-Phenyl-1-(pyridin-2-ylmethylamino)isoquinolin-3-yl)pyridin-3-yl)acetamide

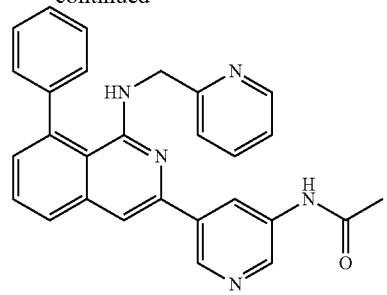

To a solution of 3-(5-aminopyridin-3-yl)-8-phenyl-N-(pyridin-2-ylmethyl)isoquinolin-1-amine (prepared as described in EXAMPLE 2) (0.15 g, 0.37 mmol) in CH$_2$Cl$_2$ (15 mL) was added pyridine (0.06 mL, 0.7 mmol) followed by acetyl chloride (0.03 mL, 0.4 mmol) at room temperature. The reaction mixture was stirred for 6 h and was diluted with water (50 mL). The aqueous mixture was extracted into CH$_2$Cl$_2$ (2×50 mL). The combined organic layer was dried over anhydrous sodium sulfate, filtered and evaporated under reduced pressure to give a residue which was purified by preparative HPLC (Condition B-66 as described in general methods) to yield N-(5-(8-phenyl-1-(pyridin-2-ylmethylamino)isoquinolin-3-yl)pyridin-3-yl)acetamide (0.030 g, 20%). LCMS Method B-12: retention time 1.90 min, [M+1]=464.40. HPLC Method B-2: retention time 8.02 min, Purity 96.32%. $^1$H NMR (400 MHz, DMSO-d$_6$) δ ppm: 2.13 (s, 3H), 4.64 (d, J=4.4 Hz, 2H), 6.08 (t, J=4.0 Hz, 1H), 7.19-7.27 (m, 3H), 7.46-7.51 (m, 5H), 7.66-7.71 (m, 3H), 7.90-7.92 (m, 1H), 8.27-8.28 (m, 1H), 8.72 (t, J=2.4 Hz, 1H), 8.77 (d, J=2.4 Hz, 1H), 9.01 (s, 1H), 10.21 (s, 1H).

Example 4

1-(5-(8-Phenyl-1-(pyridin-2-ylmethylamino)isoquinolin-3-yl)pyridin-3-yl)urea

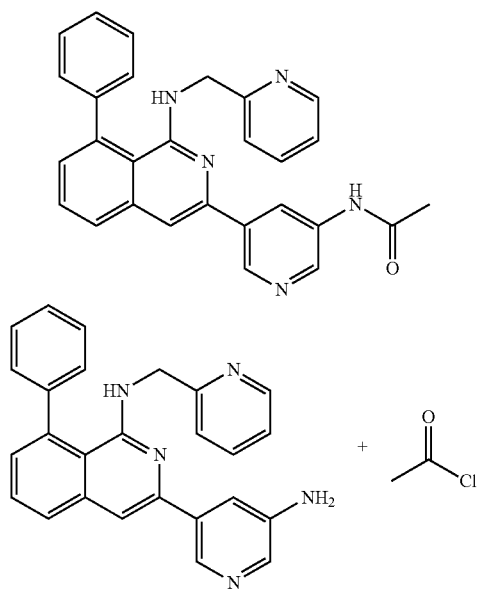

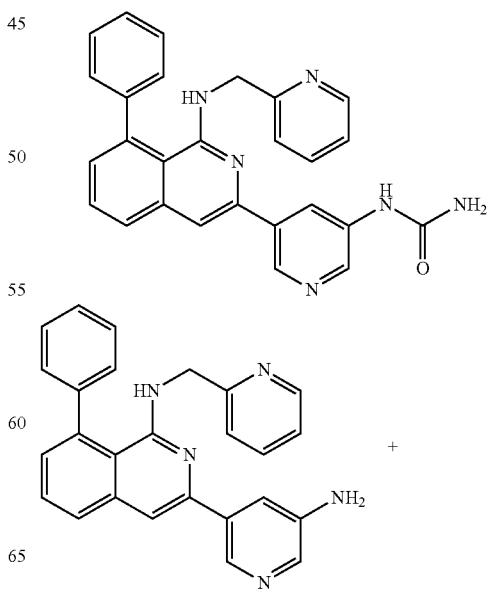

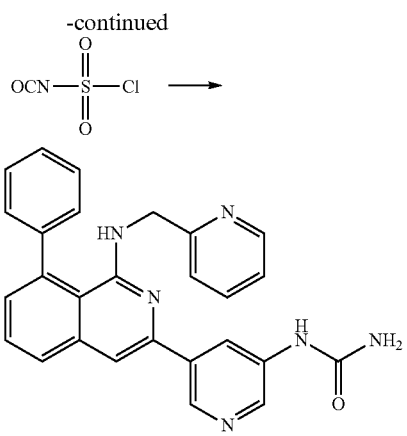

To a solution of 3-(5-aminopyridin-3-yl)-8-phenyl-N-(pyridin-2-ylmethyl)isoquinolin-1-amine described in Example 2, (0.10 g, 0.25 mmol) in dichloromethane (15 mL) was added chlorosulfonyl isocyanate (0.03 mL, 0.4 mmol) at room temperature. The reaction mixture was stirred at room temperature for 3 h. Concentrated HCl (5 mL) was added to the reaction mixture and diluted with water. The aqueous mixture was extracted with ethyl acetate (50 mL) and the aqueous layer was made basic by the addition of saturated NaOH solution. The basic solution was further extracted with ethyl acetate (2×500 mL) and the combined organic layer was dried over anhydrous sodium sulfate and filtered. The organic layer was evaporated under reduced pressure to give a residue which was purified by preparative HPLC (Condition B-72 as described in general methods) to yield 1-(5-(8-phenyl-1-((pyridin-2-ylmethyl)amino)isoquinolin-3-yl)pyridin-3-yl)urea (0.020 g, 20%). LCMS Method B-13: retention time 1.88 min, [M+1]=447.20. HPLC Method B-6: retention time 9.24 min, Purity 99.60%. $^1$H NMR (400 MHz, DMSO-d$_6$) δ ppm: 4.63 (d, J=4 Hz, 2H), 6.09 (m, 3H), 7.19-7.27 (m, 3H), 7.48-7.52 (m, 5H), 7.66-7.70 (m, 3H), 7.92 (d, J=8 Hz, 1H), 8.27 (d, J=4.4 Hz, 1H), 8.57 (t, J=2 Hz, 1H), 8.61 (d, J=2.4 Hz, 1H), 8.85 (s, 1H), 8.90 (d, J=1.6 Hz, 1H).

Example 5

3-(5-Aminopyridin-3-yl)-8-phenyl-N-(pyridin-2-ylmethyl)isoquinolin-1-sulfonyl urea

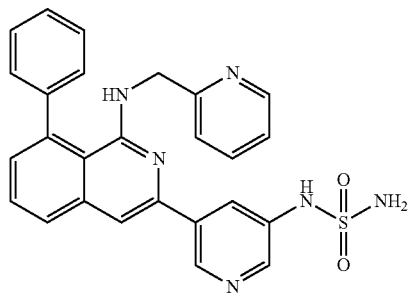

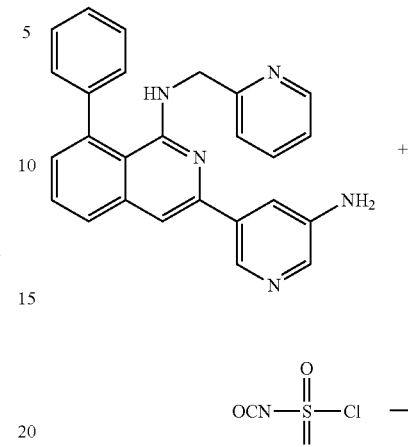

To a solution of chlorosulfonyl isocyanate (0.013 mL, 0.15 mmol) in dichloromethane (10 mL) was added t-BuOH (0.014 mL, 0.15 mmol) at room temperature. The reaction mixture was stirred at room temperature for 10 min. 3-(5-Aminopyridin-3-yl)-8-phenyl-N-(pyridin-2-ylmethyl)isoquinolin-1-amine described in Example 2, (0.050 g, 0.12 mmol) was added to the reaction mixture and stirred for 3 h. Concentrated HCl (5 mL) was added to the reaction mixture and diluted with water. The aqueous mixture was extracted with ethyl acetate (50 mL) and the aqueous layer was made basic by the addition of saturated NaOH solution. The basic solution was further extracted with ethyl acetate (2×500 mL) and the combined organic layer was dried over anhydrous sodium sulfate and filtered. The organic layer was evaporated under reduced pressure to give a residue which was purified by preparative HPLC (Condition B-64 as described in general methods) to yield 3-(5-aminopyridin-3-yl)-8-phenyl-N-(pyridin-2-ylmethyl)isoquinolin-1-sulfonyl urea (0.013 g, 22%). LCMS Method B-13: retention time 2.17 min, [M+1]=483.20. HPLC Method B-2: retention time 6.21 min, Purity 98.77%. $^1$H NMR (400 MHz, DMSO-d$_6$) δ ppm: 4.64 (d, J=4.4 Hz, 2H), 6.09 (t, J=4.4 Hz, 1H), 7.19-7.27 (m, 5H), 7.46-7.52 (m, 5H), 7.66-7.72 (m, 3H), 7.80 (dd, J=8.4 Hz, J=8.4 Hz, 1H), 8.26-8.41 (m, 2H), 8.96 (s, 1H), 8.99 (s, 1H) 10.01 (br s, 1H).

Example 6

N-(3-(8-Phenyl-1-(pyridin-2-ylmethylamino)isoquinolin-3-yl)phenyl)morpholine-4-carboxamide

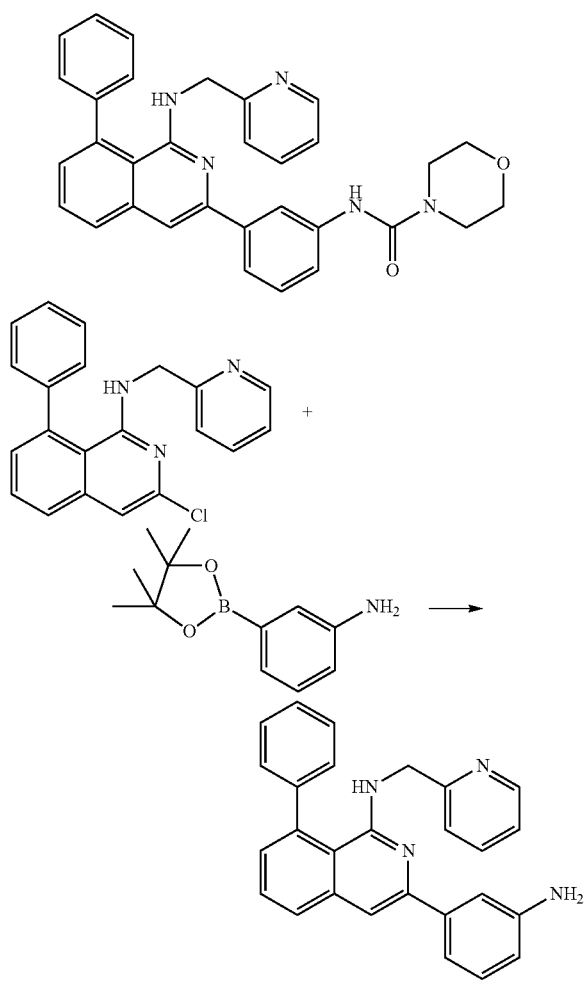

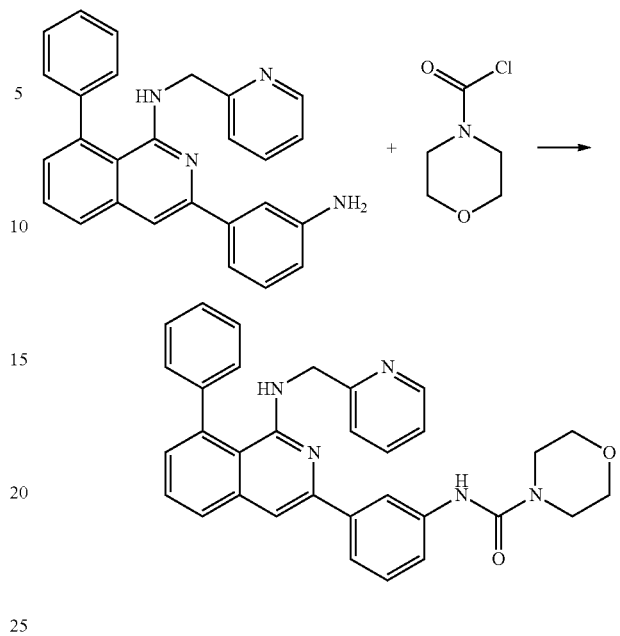

To a solution of 3-chloro-8-phenyl-N-(pyridin-2-ylmethyl)isoquinolin-1-amine (0.30 g, 0.87 mmol) was converted into 3-(3-aminophenyl)-8-phenyl-N-(pyridin-2-ylmethyl)isoquinolin-1-amine via Suzuki cross coupling using the conditions described in Example 1. Following reagents are used for the conversion: 3-(4,4,5,5-tetramethyl-1,3,2-dioxaborolan-2-yl)aniline (0.21 g, 0.95 mmol), potassium carbonate (0.36 g, 2.6 mmol), 1,1'-bis(diphenylphosphino)ferrocene-palladium(II)dichloride dichloromethane complex (0.03 g, 0.04 mmol). The resulting residue was purified by silica gel column chromatography using CombiFlash (12 g REDISEP® column) with 50% ethyl acetate in hexane an eluent to yield 3-(3-aminophenyl)-8-phenyl-N-(pyridin-2-ylmethyl)isoquinolin-1-amine (0.25 g, 72%). LCMS Method B-12: retention time 2.09 min, [M+1]=403.30. $^1$H NMR (400 MHz, DMSO-d$_6$) δ ppm: 4.64 (d, J=4.40 Hz, 2H), 5.19 (s, 2H), 5.98 (t, J=4.4 Hz, 1H), 6.58-6.61 (m, 1H), 7.09-7.12 (m, 3H), 7.19-7.20 (m, 1H), 7.20-7.21 (m, 1H), 7.21-7.51 (m, 6H), 7.53-7.68 (m, 2H), 7.84-7.86 (m, 2H), 8.28-8.29 (m, 1H).

To a solution of 3-(3-aminophenyl)-8-phenyl-N-(pyridin-2-ylmethyl)isoquinolin-1-amine (0.10 g, 0.25 mmol) in CH$_2$Cl$_2$ (20 mL) was added pyridine (0.040 mL, 0.49 mmol) followed by morpholine-4-carbonyl chloride (0.040 g, 0.27 mmol) at room temperature and stirred for 6 h. The reaction mixture was diluted with water (100 mL) and extracted into CH$_2$Cl$_2$ (2×50 mL). The combined organic layer was dried over anhydrous sodium sulfate, filtered and concentrated under reduced pressure to give a residue which was purified by preparative HPLC (Condition B-72 as described in general methods) to yield N-(3-(8-phenyl-1-((pyridin-2-ylmethyl)amino)isoquinolin-3-yl)phenyl)morpholine-4-carboxamide (0.070 g, 60%). LCMS Method B-12: retention time 2.08 min, [M+1]=516.50. HPLC Method B-2: retention time 7.80 min, Purity 99.00%. $^1$H NMR (400 MHz, DMSO-d$_6$) δ ppm: 3.47 (t, J=4.8 Hz, 4H), 3.64 (t, J=4.8 Hz, 4H), 4.64 (d, J=4 Hz, 2H), 6.01 (t, J=4.4 Hz, 1H), 7.21-7.36 (m, 4H), 7.46-7.54 (m, 5H), 7.57 (s, 1H), 7.63-7.70 (m, 3H), 7.76 (d, J=7.6 Hz, 1H), 7.89 (dd, J=8.0 Hz, J=0.8 Hz, 1H), 8.21 (t, J=2 Hz, 1H), 8.28 (d, J=2 Hz, 1H), 8.64 (s, 1H).

Example 7

2-(3-(8-Phenyl-1-(pyridin-2-ylmethylamino)isoquinolin-3-yl)phenylsulfonyl)acetamide

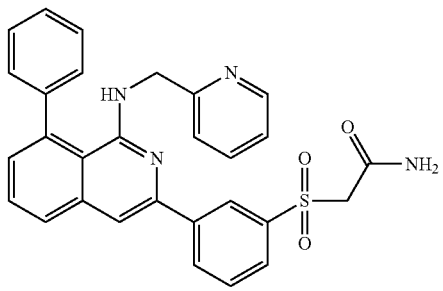

-continued

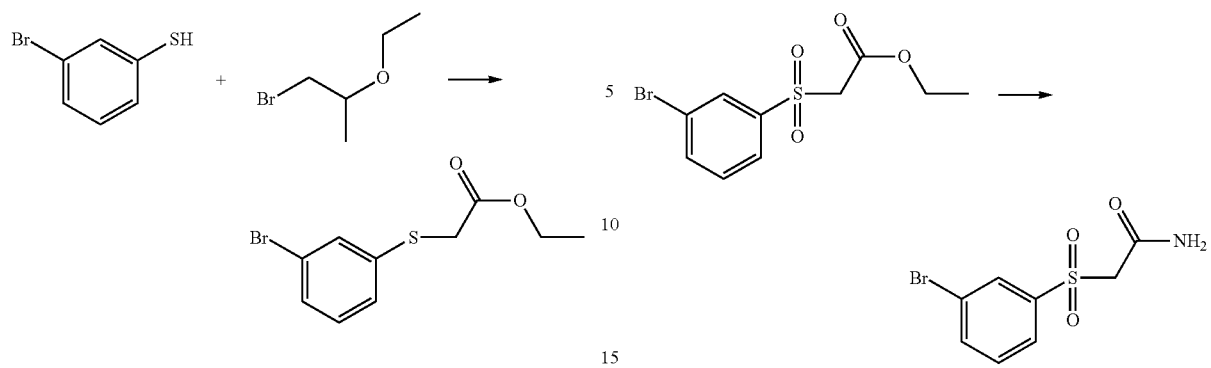

To a stirred solution of 3-bromobenzenethiol (0.15 g, 0.79 mmol) in DMF (5 mL) were added potassium carbonate (0.329 g, 2.38 mmol) and ethyl 2-bromoacetate (0.132 g, 0.793 mmol). The resulting mixture was heated at 120° C. for 16 h. The reaction mixture was diluted with water (100 mL) and extracted into EtOAc (2×50 mL). The combined organic layer was dried over anhydrous sodium sulfate, filtered and concentrated under reduced pressure. The resultant residue was purified by silica gel column chromatography using CombiFlash (12 g REDISEP® column) with 8% ethyl acetate in hexane as an eluent to yield ethyl 2-((3-bromophenyl)thio)acetate (0.14 g, 64%). $^1$H NMR (400 MHz, CDCl$_3$) δ ppm: 1.25 (t, J=7.2 Hz, 3H), 4.21 (q, J=7.2 Hz, 2H), 7.17 (t, J=7.6 Hz, 1H), 7.25-7.36 (m, 2H), 7.55 (d, J=1.6 Hz, 1H).

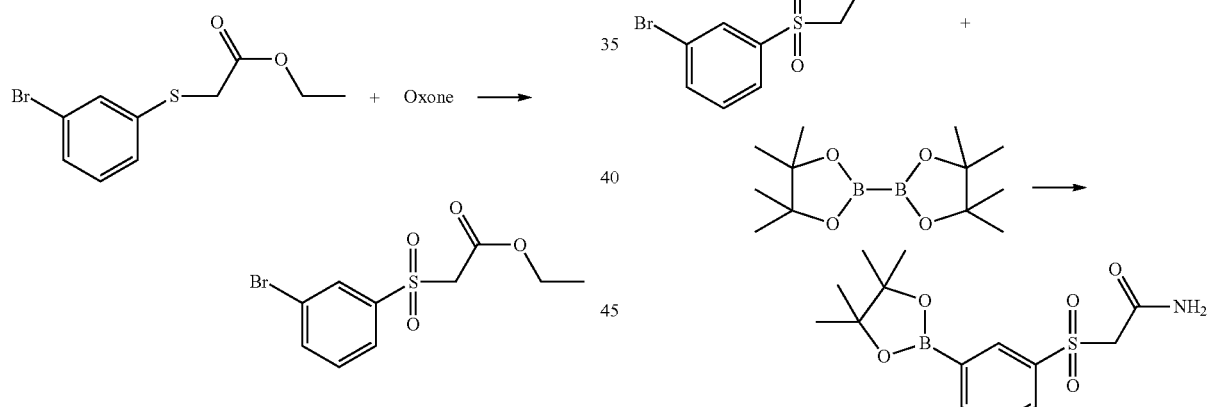

To a stirred solution of ethyl 2-((3-bromophenyl)thio)acetate (0.810 g, 2.91 mmol) in MeOH (8 mL) and water (2.5 mL) was added OXONE® (1.97 g, 3.20 mmol) and the resulting mixture was stirred over night at room temperature. The reaction mixture was diluted with water (100 mL) and extracted with EtOAc (2×25 mL). The combined organic layer were washed with brine, dried over sodium sulfate, filtered and concentrated under reduced pressure. The resulting residue was purified by silica gel column chromatography using CombiFlash (12 g REDISEP® column) with 20% ethyl acetate in hexane as an eluent to yield ethyl 2-((3-bromophenyl)sulfonyl)acetate (0.58 g, 65% yield). $^1$H NMR (400 MHz, CDCl$_3$) δ ppm: 1.25 (t, J=7.2 Hz, 3H), 4.20 (q, J=7.2 Hz, 2H), 7.47 (t, J=8.0 Hz, 1H), 7.80 (dd, J=0.8 Hz, J=0.8 Hz, 1H), 7.89 (dd, J=0.4 Hz, J=0.8 Hz, 1H), 8.12 (s, 1H).

To a solution of methyl 2-((3-bromophenyl)sulfonyl)acetate (0.10 g, 0.34 mmol) in MeOH (20 mL) was purged with ammonia at –78° C. in a sealed tube for 10 min. The reaction mixture was stirred for 14 h at room temperature and concentrated to give crude residue 2-((3-bromophenyl)sulfonyl)acetamide (80 mg, 84%). The crude residue was taken for the next step without further purification. LCMS Method B-10: retention time 0.89 min, [M+1]=279.0.

To a stirred solution of 2-((3-bromophenyl)sulfonyl)acetamide (0.100 g, 0.360 mmol) in dioxane was added bis(pinacolato)diboron (0.119 g, 0.467 mmol) and potassium acetate (0.106 g, 1.08 mmol). The contents were purged with nitrogen for 10 min and 1,1'-bis(diphenylphosphino)ferrocene-palladium(II)dichloride dichloromethane complex (0.023 g, 0.029 mmol) was added. The reaction mixture was heated at 100° C. for 12 h and allowed to cool room temperature. The reaction mixture was filtered through a pad of CELITE®. The filtrate was evaporated under reduced pressure to yield a brown residue (0.10 g, 86%). The residue was taken to next step without purification.

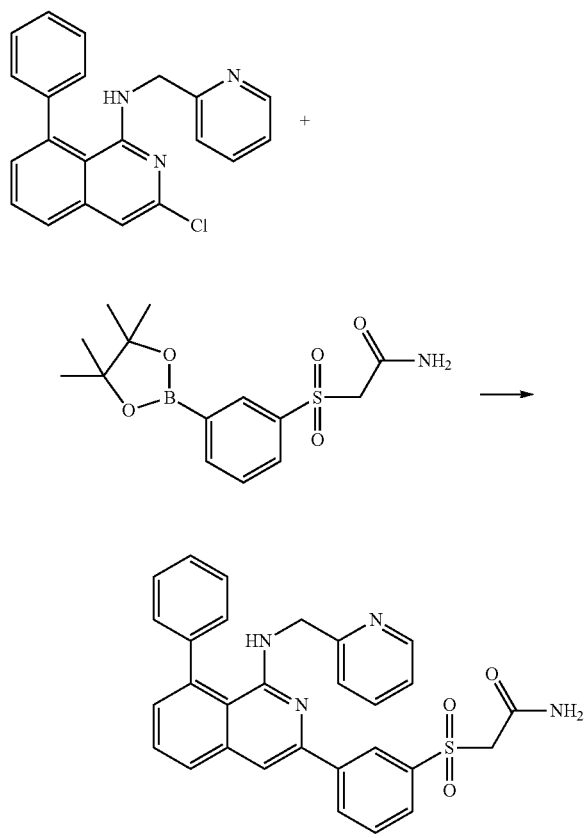

3-Chloro-8-phenyl-N-(pyridin-2-ylmethyl)isoquinolin-1-amine (prepared as described in Example 1) (0.10 g, 0.29 mmol) was converted to 2-(3-(8-phenyl-1-(pyridin-2-ylmethylamino)isoquinolin-3-yl)phenylsulfonyl)acetamide via Suzuki cross coupling using the conditions described in Example 1. Following reagents are utilized for this reaction: 2-(3-(4,4,5,5-tetramethyl-1,3,2-dioxaborolan-2-yl)phenylsulfonyl)acetamide (0.087 g, 0.27 mmol), potassium carbonate (0.12 g, 0.87 mmol) and 1,1'-bis(diphenylphosphino)ferrocene-palladium(II)dichloride dichloromethane complex (0.022 g, 0.027 mmol). The resulting residue was purified by preparative HPLC (Condition B-66 as described in general methods) to yield 2-(3-(8-phenyl-1-(pyridin-2-ylmethylamino)isoquinolin-3-yl)phenylsulfonyl)acetamide (0.030 g, 30%). LCMS Method B-13: retention time 2.06 min, [M+1]=509.20. HPLC Method B-2: retention time 7.24 min, Purity 98.85%. $^1$H NMR (400 MHz, DMSO-$d_6$) δ ppm: 4.33 (s, 1H), 4.64 (d, J=4 Hz, 2H), 6.09 (t, J=4.0 Hz, 1H), 7.19-7.22 (m, 2H), 7.25 (d, J=8 Hz, 1H), 7.29 (dd, J=7.2 Hz, J=1.2 Hz, 1H), 7.37 (br s, 1H), 7.49-7.53 (m, 5H), 7.61 (br s, 1H), 7.66-7.76 (m, 3H), 7.82 (s, 1H), 7.87-7.89 (m, 1H), 7.95 (dd, J=8.0 Hz, J=1.2 Hz, 1H), 8.29-8.31 (m, 1H), 8.50 (m, 1H), 8.63 (t, J=1.6 Hz, 1H).

Example 8

5-(4-Methyl-8-phenyl-1-(pyridin-2-ylmethylamino)isoquinolin-3-yl)pyridine-3-sulfonamide

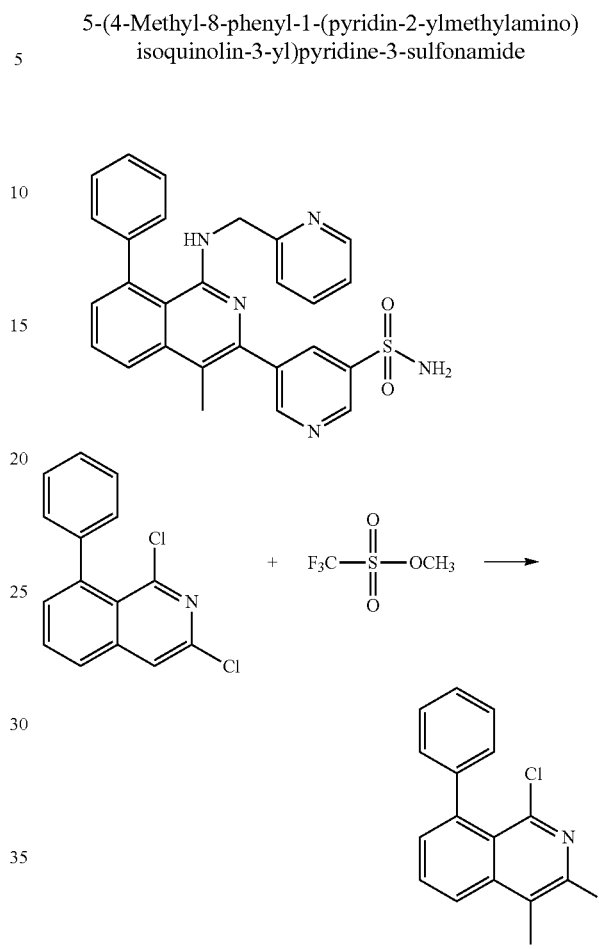

To a solution of diisopropylamine (0.31 mL, 2.2 mmol) in THF (5 mL) was added n-BuLi (1.60 M in hexane, 1.30 mL, 2.18 mmol) at −40° C. The reaction mixture was allowed to stir at −10° C. for 10 min. Then 1,3-dichloro-8-phenylisoquinoline (0.30 g, 1.1 mmol) (obtained as described for Example 1) in THF (10 mL) was added dropwise at −78° C. and stirred for 1 h. Methyl trifluoromethanesulfonate (0.36 mL, 3.3 mmol) in THF (5 mL) was added dropwise to the reaction mixture at −78° C. and stirred for 30 min. The reaction mixture was quenched by the addition of saturated ammonium chloride solution (50 mL) at 0° C. and the resulting mixture extracted with ethyl acetate (2×50 mL). The combined organic layer was dried over sodium sulfate, filtered and evaporated under reduced pressure to give a residue which was purified by silica gel column chromatography using CombiFlash (12 g REDISEP® column) with 30% ethyl acetate in hexane as an eluent to yield 1,3-dichloro-4-methyl-8-phenylisoquinoline (0.28 g, 75%). LCMS Method B-11: retention time 2.45 min, [M+l]= 288.00. $^1$H NMR (400 MHz, DMSO-$d_6$) δ ppm: 2.74 (s, 3H), 7.33-7.37 (m, 2H), 7.37-7.47 (m, 3H), 7.61-7.63 (m, 1H), 7.93-7.98 (m, 1H) 8.23-8.27 (m, 1H).

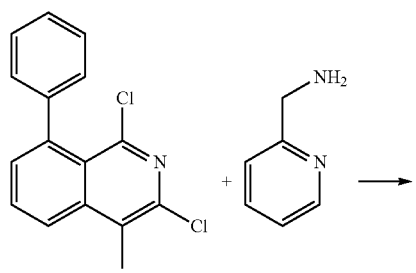

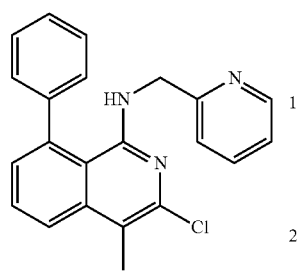

1,3-Dichloro-4-methyl-8-phenylisoquinoline (0.28 g, 0.97 mmol) was converted into 3-chloro-4-methyl-8-phenyl-N-(pyridin-2-ylmethyl)isoquinolin-1-amine as described in Example 1, using 2-(amino methyl)pyridine (5 mL) in a sealed tube at 100° C. The resulting residue was purified by preparative HPLC (Condition B-64 as described in general methods) to yield 3-chloro-4-methyl-8-phenyl-N-(pyridin-2-ylmethyl)isoquinolin-1-amine (0.22 g, 63%). $^1$H NMR (400 MHz, DMSO-d$_6$) δ ppm: δ 2.53 (s, 3H), 4.44 (d, J=4.02 Hz, 2H), 6.19-6.23 (m, 1H), 7.18-7.24 (m, 2H), 7.28 (d, J=7.03 Hz, 1H), 7.41-7.51 (m, 5H), 7.68 (t, J=7.65 Hz, 1H), 7.75 (t, J=7.78 Hz, 1H), 7.95 (d, J=8.53 Hz, 1H), 8.21 (d, J=4.52 Hz, 1H).

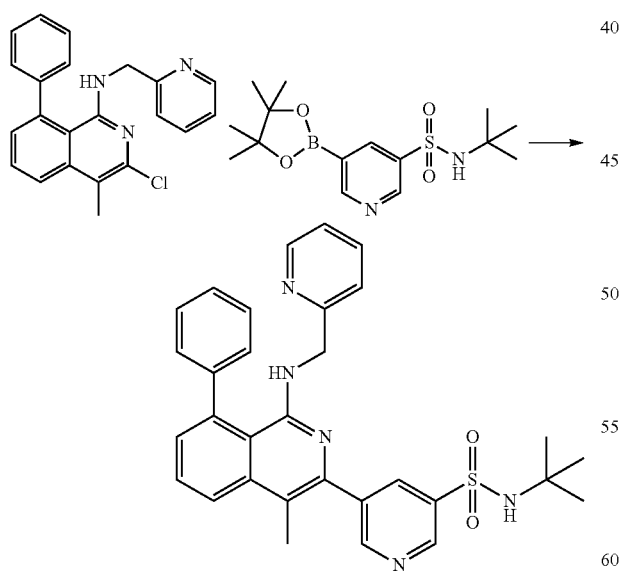

3-Chloro-4-methyl-8-phenyl-N-(pyridin-2-ylmethyl)isoquinolin-1-amine (0.20 g, 0.55 mmol), was converted to N-(tert-butyl)-5-(4-methyl-8-phenyl-1-((pyridin-2-ylmethyl)amino)isoquinolin-3-yl)pyridine-3-sulfonamide using the Suzuki cross coupling conditions as described for the preparation of Example 1. Following reagents are utilized for the conversion: N-(tert-butyl)-5-(4,4,5,5-tetramethyl-1,3,2-dioxaborolan-2-yl)pyridine-3-sulfonamide (0.28 g, 0.83 mmol), potassium carbonate (0.23 g, 1.7 mmol) and 1,1'-bis(diphenylphosphino)ferrocene-palladium(II)dichloride dichloromethane complex (0.02 g, 0.03 mmol). The resulting residue was purified by silica gel column chromatography using CombiFlash (12 g REDISEP® column) with 50% ethyl acetate in hexane an eluent to yield N-(tert-butyl)-5-(4-methyl-8-phenyl-1-((pyridin-2-ylmethyl)amino)isoquinolin-3-yl)pyridine-3-sulfonamide (0.15 g, 50%). LCMS Method B-11: retention time 2.29 min, [M+1]=538.20.

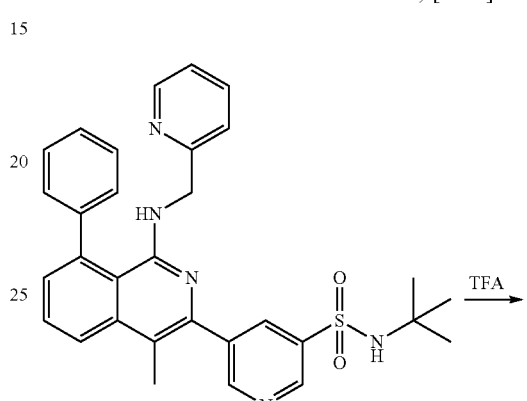

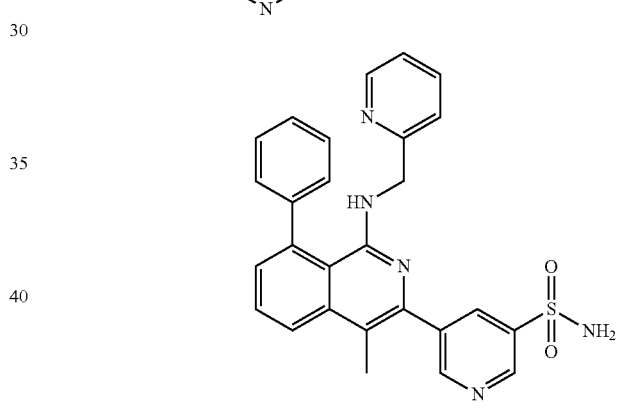

N-(tert-Butyl)-5-(4-methyl-8-phenyl-1-((pyridin-2-ylmethyl)amino)isoquinolin-3-yl)pyridine-3-sulfonamide (0.15 g, 0.27 mmol) was converted to 5-(4-methyl-8-phenyl-1-((pyridin-2-ylmethyl)amino)isoquinolin-3-yl)pyridine-3-sulfonamide using TFA (10 mL) by following the procedure described for Example 1. The resulting residue was purified by preparative HPLC (Condition B-64 as described in general methods) to yield 5-(4-methyl-8-phenyl-1-((pyridin-2-ylmethyl)amino)isoquinolin-3-yl)pyridine-3-sulfonamide (0.01 g, 7%). LCMS Method B-11: retention time 1.93 min, [M+1]=482.20. HPLC Method B-2: retention time 6.76 min, Purity 96.55%. $^1$H NMR (400 MHz, DMSO-d$_6$) δ ppm: 2.57 (s, 3H), 4.49 (d, J=4.4 Hz, 2H), 6.00 (t, J=4.4 Hz, 1H), 7.19-7.20 (m, 2H), 7.37 (dd, J=7.2 Hz, J=0.8 Hz, 1H), 7.46-7.51 (m, 5H), 7.63-7.69 (m, 3H), 7.80 (dd, J=8.4 Hz, J=7.2 Hz, 1H), 8.07 (dd, J=8.8 Hz, J=1.2 Hz, 1H), 8.25 (d, J=4.8 Hz, 1H), 8.38 (t, J=2 Hz, 1H), 8.99 (dd, J=4 Hz, J=2.4 Hz, 2H).

Example 9

5-(8-Phenyl-1-((pyridin-2-ylmethyl)amino)isoquinolin-3-yl)nicotinamide

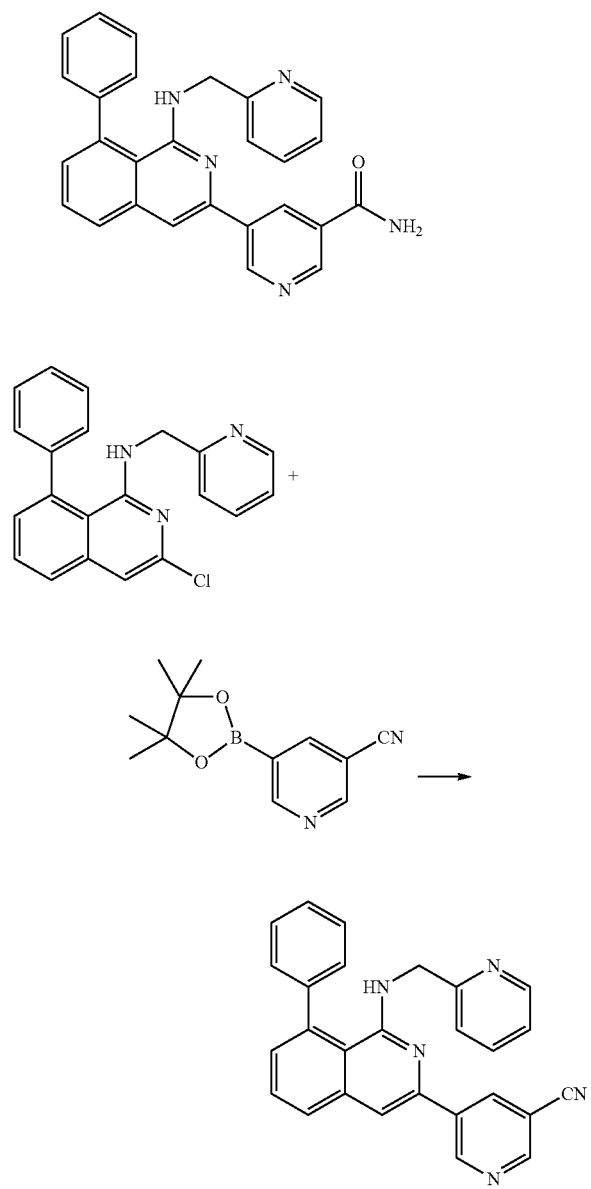

3-Chloro-8-phenyl-N-(pyridin-2-ylmethyl)isoquinolin-1-amine (0.10 g, 0.29 mmol) was converted into 5-(8-phenyl-1-((pyridin-2-ylmethyl)amino)isoquinolin-3-yl)nicotinonitrile using the Suzuki cross coupling as described for Example 1. Following reagents are utilized for the conversion: 5-(4,4,5,5-tetramethyl-1,3,2-dioxaborolan-2-yl)nicotinonitrile (0.80 g, 0.35 mmol), K$_2$CO$_3$ (0.12 mg, 0.87 mmol) and 1,1'-bis(diphenylphosphino)ferrocene-palladium(II)dichloride dichloromethane complex (0.011 mg, 0.010 mmol). The resulting residue was purified by silica gel column chromatography using CombiFlash (12 g REDISEP® column) with 50% ethyl acetate in hexane as an eluent to yield 5-(8-phenyl-1-((pyridin-2-ylmethyl)amino)isoquinolin-3-yl)nicotinonitrile (0.070 g, 60%) as an off-white solid. LCMS Method B-12 retention time 2.21 min, [M+1]= 414.20. HPLC Method B-6: retention time 9.76 min, Purity 95.50%. $^1$H NMR (400 MHz, DMSO-d$_6$) δ ppm: 4.65 (d, J=4.00 Hz, 2H), 6.23 (t, J=4.00 Hz, 1H), 7.19-7.28 (m, 3H), 7.30-7.33 (m, 5H), 7.48-7.54 (m, 2H), 7.65-7.73 (m, 1H), 7.90 (s, 1H), 8.28-8.29 (d, J=2.00 Hz, 1H), 8.91-8.92 (d, J=2.00 Hz, 1H), 9.01-9.03 (d, J=2.00 Hz, 1H), 9.65 (s, 1H).

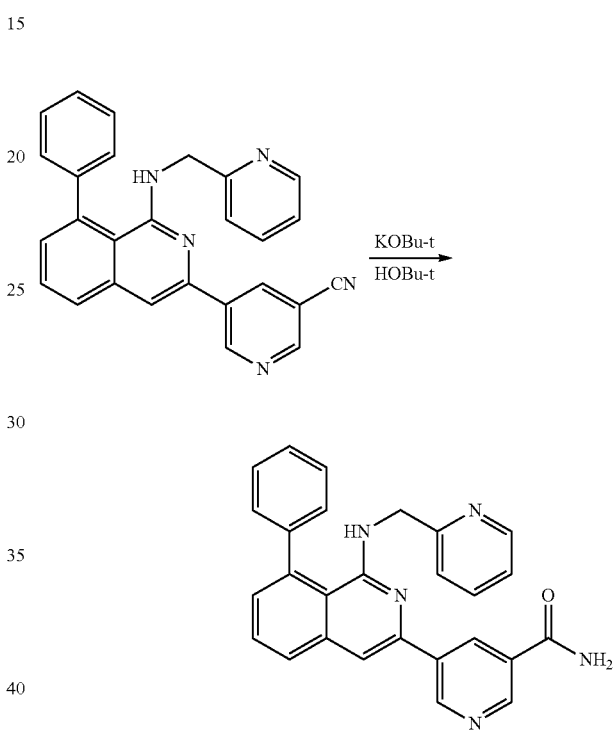

To a stirred solution of 3-(8-phenyl-1-((pyridin-2-ylmethyl)amino)isoquinolin-3-yl)benzonitrile (0.05 g, 0.1 mmol) in t-BuOH (1.74 mL, 18.2 mmol) was added potassium tert-butoxide (0.041 g, 0.36 mmol). The reaction mixture was stirred at 80° C. for 6 h and allowed to cool to room temperature. The reaction mixture was diluted in dichloromethane (20 mL) and the solution washed with 1.5 N HCl (5 mL). The organic layer was separated, dried over anhydrous sodium sulfate and concentrated to give a yellow solid which was purified over silica gel column chromatography using CombiFlash (12 g REDISEP® column) with 4% methanol in chloroform as an eluent to yield 5-(8-phenyl-1-((pyridin-2-ylmethyl)amino)isoquinolin-3-yl)nicotinamide (12 mg, 14%) as off-white solid. LCMS Method B-12 retention time 2.21 min, [M+1]=432.20. HPLC Method B-6: retention time 7.06 min, Purity 96.20%. $^1$H NMR (400 MHz, DMSO-d$_6$) δ ppm: 4.66-4.67 (d, J=4.00 Hz, 2H), 6.17 (t, J=4.00 Hz, 1H), 7.19-7.30 (m, 3H), 7.50-7.56 (m, 5H), 7.66-7.88 (m, 2H), 7.91-7.93 (m, 2H), 7.90 (s, 1H), 8.27-8.28 (m, 2H), 8.92 (d, J=2.00 Hz, 1H), 9.01 (d, J=2.00 Hz, 1H), 9.55 (s, 1H).

Example 10

5-(3-Chloro-8-phenyl-1-(pyridin-2-ylmethylamino)isoquinolin-4-yl)pyridine-3-sulfonamide

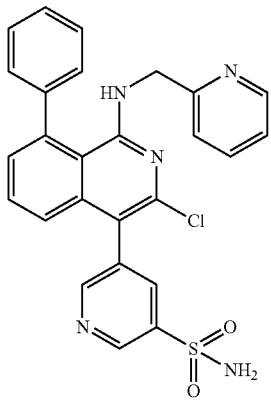

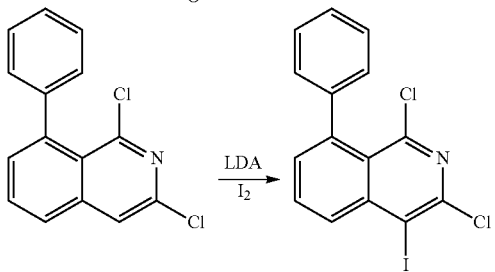

To a solution of diisopropylamine (2.08 mL, 14.6 mmol) in THF (5 mL) was added n-BuLi (1.6 M in hexane, 9.10 mL, 6.57 mmol) at −40° C. The reaction mixture was allowed to stir at −10° C. for 10 min. 1,3-dichloro-8-phenylisoquinoline (2.00 g, 7.30 mmol) in THF (10 mL) was added dropwise to the reaction mixture at −78° C. and stirred for 1 h. To this reaction mixture, iodine (5.55 g, 21.9 mmol) in THF (10 mL) was added dropwise at −78° C. After 10 min, the reaction mixture was quenched by the addition of saturated ammonium chloride solution (50 mL) at 0° C. The aqueous mixture was extracted with ethyl acetate (2×50 mL). The combined organic layer was dried over sodium sulfate, filtered and concentrated under reduced pressure to give a residue which was purified by silica gel column chromatography using CombiFlash (24 g REDISEP® column) with 30% ethyl acetate in hexane as an eluent to yield 1,3-dichloro-4-iodo-8-phenylisoquinoline (1.7 g, 58%). LCMS Method B-11: retention time 2.47 min, [M+1]= 400.0. $^1$H NMR (400 MHz, DMSO-d$_6$) δ ppm: 7.37-7.39 (m, 2H), 7.44-7.48 (m, 3H), 7.72 (d, J=1.2 Hz, 1H), 8.03 (t, J=7.2 Hz, 1H), 8.30 (d, J=1 Hz, 1H).

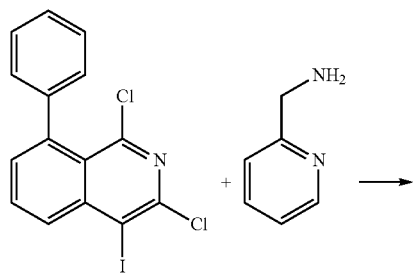

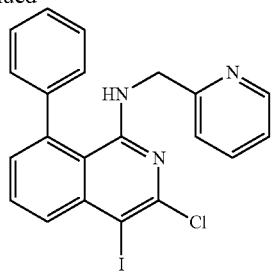

A solution of 1,3-dichloro-4-iodo-8-phenylisoquinoline (0.30 g, 0.75 mmol) in 2-(amino methyl)pyridine (10 mL) was heated in a sealed tube at 100° C. for 12 h. The reaction mixture was diluted with water (100 mL) and extracted with ethyl acetate (3×50 mL); the combined organic layer was dried over anhydrous sodium sulfate, filtered and evaporated under reduced pressure to give a residue which was purified by silica gel column chromatography using CombiFlash (12 g REDISEP® column) with 15% ethyl acetate in hexane as an eluent to yield 3-chloro-4-iodo-8-phenyl-N-(pyridin-2-ylmethyl)isoquinolin-1-amine (0.28 g, 79%). LCMS Method B-11: retention time 2.58 min, [M+1]=472.0. $^1$H NMR (400 MHz, DMSO-d$_6$) δ ppm: 4.45 (d, J=4 Hz, 2H), 6.56 (t, J=4 Hz, 1H), 7.20-7.37 (m, 3H), 7.43-7.51 (m, 5H), 7.64-7.80 (m, 2H), 8.07 (m, 1H), 8.17 (d, J=4 Hz, 1H).

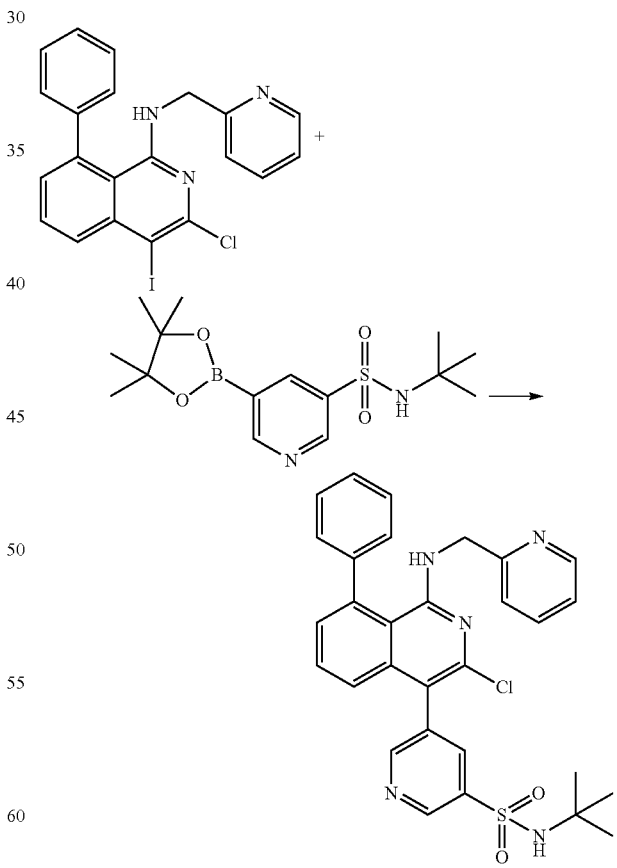

3-Chloro-4-iodo-8-phenyl-N-(pyridin-2-ylmethyl)isoquinolin-1-amine (0.20 g, 0.42 mmol) was converted into N-(tert-butyl)-5-(3-chloro-8-phenyl-1-((pyridin-2-ylmethyl)amino)isoquinolin-4-yl)pyridine-3-sulfonamide using the Suzuki cross coupling as described for Example 1. Following reagents are utilized for the conversion: N-(tert-butyl)-5-(4,4,5,5-tetramethyl-1,3,2-dioxaborolan-2-yl)pyridine-3-sulfonamide (0.22 g, 0.64 mmol), potassium carbonate (0.18 g, 1.3 mmol) and 1,1'-bis(diphenylphosphino)ferrocene-palladium(II)dichloride dichloromethane complex (0.02 g, 0.02 mmol). The resulting residue was purified by silica gel column chromatography using CombiFlash (12 g REDISEP® column) with 50% ethyl acetate in hexane as an eluent to yield N-(tert-butyl)-5-(3-chloro-8-phenyl-1-((pyridin-2-ylmethyl)amino)isoquinolin-4-yl)pyridine-3-sulfonamide (0.13 g, 55%). LCMS Method B-17: retention time 2.45 min, [M−1]=484.0. $^1$H NMR (400 MHz, DMSO-d$_6$) δ ppm: 1.18 (s, 9H), 4.56 (d, J=4 Hz, 2H), 6.68 (t, J=4 Hz, 1H), 7.15-7.34 (m, 4H), 7.0-7.55 (m, 5H), 7.64-7.72 (m, 2H), 7.86 (s, 1H), 8.21 (m, 2H), 8.81 (d, J=2 Hz, 1H), 9.08 (d, J=2 Hz, 1H).

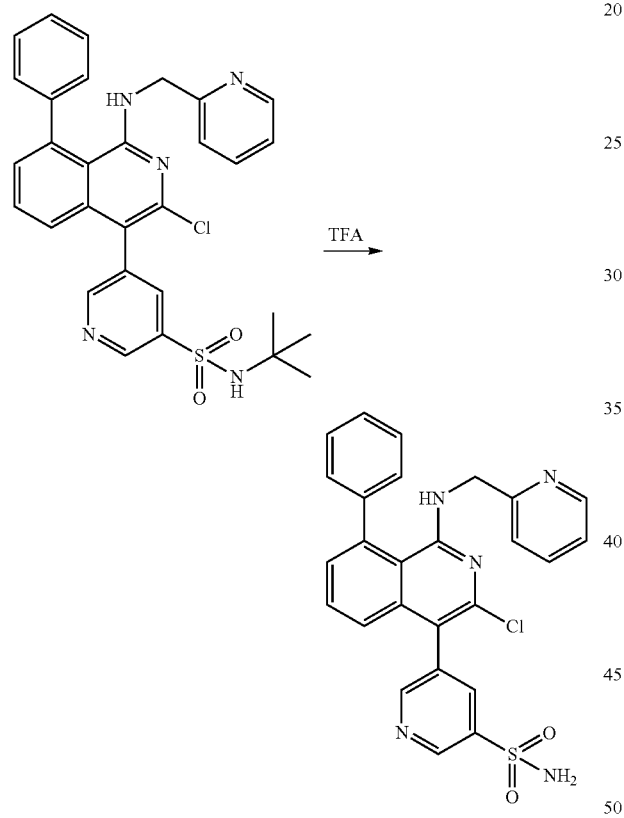

N-(tert-Butyl)-5-(3-chloro-8-phenyl-1-((pyridin-2-ylmethyl)amino)isoquinolin-4-yl)pyridine-3-sulfonamide (0.13 g, 0.23 mmol) was converted into 5-(3-chloro-8-phenyl-1-((pyridin-2-ylmethyl)amino)isoquinolin-4-yl)pyridine-3-sulfonamide using TFA (10 mL) at room temperature using the procedure described for Example 1. The resulting residue was purified by preparative HPLC (Condition B-64 as described in general methods) to yield 5-(3-chloro-8-phenyl-1-((pyridin-2-ylmethyl)amino)isoquinolin-4-yl)pyridine-3-sulfonamide (0.080 g, 70%). LCMS Method B-13: retention time 2.22 min, [M+1]=502.20. HPLC Method B-5: retention time 7.43 min, Purity 98.33%. $^1$H NMR (400 MHz, DMSO-d$_6$) δ ppm: 4.55 (d, J=4 Hz, 2H), 6.66 (t, J=4 Hz, 1H), 7.23-7.34 (m, 4H), 7.48-7.54 (m, 5H), 7.64-7.73 (m, 4H), 8.19 (t, J=2.4 Hz, 1H), 8.21 (d, J=4 Hz, 1H), 8.81 (d, J=2 Hz, 1H), 9.08 (d, J=2 Hz, 1H).

Example 11

5-(8-Phenyl-1-(pyridin-2-ylmethylamino)isoquinolin-4-yl)pyridine-3-sulfonamide

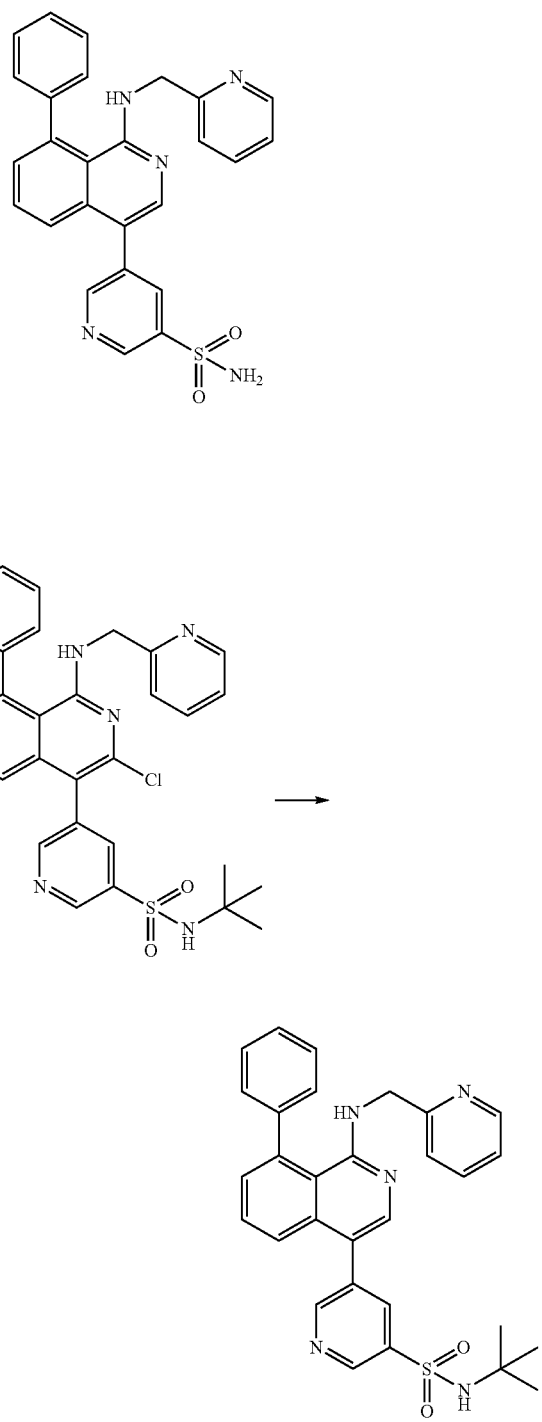

To a solution of N-(tert-butyl)-5-(3-chloro-8-phenyl-1-((pyridin-2-ylmethyl)amino)isoquinolin-4-yl)pyridine-3-sulfonamide (preparation described in Example 10) (0.30 g, 0.54 mmol) in methanol (50 mL) was added 10% palladium on carbon (0.50 g, 4.70 mmol). The reaction mixture was stirred at hydrogen pressure (5 kg/cm²) in an autoclave for 8 h. The reaction mixture was filtered through a pad of CELITE® and the filtrate was concentrated under reduced pressure to give a residue which was purified by preparative HPLC (Condition B-58 described in general methods) to yield N-(tert-butyl)-5-(8-phenyl-1-((pyridin-2-ylmethyl)amino)isoquinolin-4-yl)pyridine-3-sulfonamide (0.040 g, 10%). LCMS Method B-40: retention time 1.18 min, [M+1]=524.38. ¹H NMR (400 MHz, DMSO-d₆) δ ppm: 1.19 (s, 9H), 4.67 (d, J=4 Hz, 2H), 7.30-7.32 (m, 3H), 7.48-7.7.62 (m, 7H), 7.83-7.87 (m, 3H), 7.96 (s, 1H), 8.27 (m 2H), 8.93 (d, J=2 Hz, 1H), 9.08 (s, 1H).

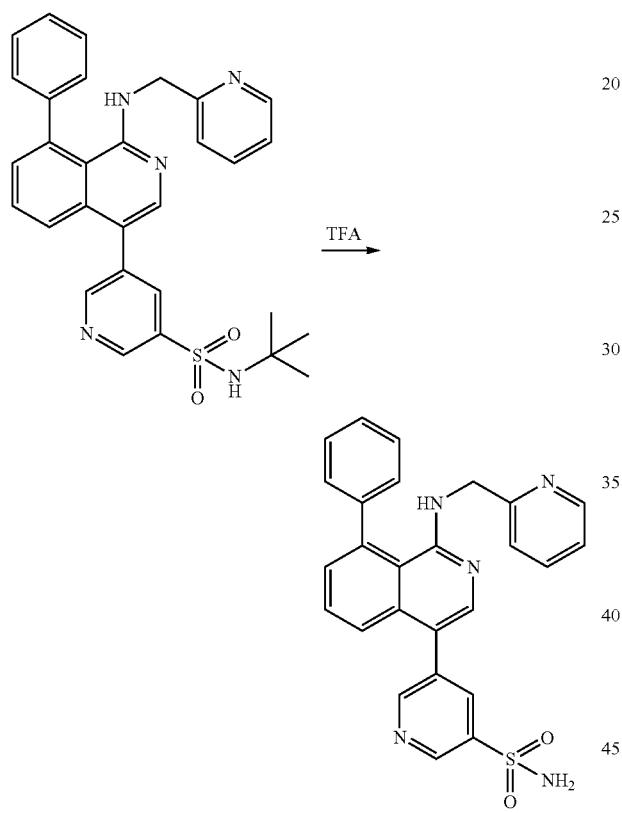

N-(tert-Butyl)-5-(8-phenyl-1-((pyridin-2-ylmethyl)amino)isoquinolin-4-yl)pyridine-3-sulfonamide (0.04 g, 0.08 mmol) was converted into 5-(8-phenyl-1-((pyridin-2-ylmethyl)amino)isoquinolin-4-yl)pyridine-3-sulfonamide using TFA (15 mL) as described for Example 1. The resulting residue was purified by preparative HPLC (Condition B-72 described in general methods) to yield 5-(8-phenyl-1-((pyridin-2-ylmethyl)amino)isoquinolin-4-yl)pyridine-3-sulfonamide (0.013 g, 36%). LCMS Method B-13: retention time 1.87 min, [M+1]=468.20. HPLC Method B-5: retention time 6.25 min, Purity 99.65%. ¹H NMR (400 MHz, DMSO-d₆) δ ppm:4.57 (d, J=4 Hz, 2H), 6.27 (t, J=4 Hz, 1H), 7.20-7.23 (m, 2H), 7.37 (dd, J=1.2 Hz, J=7.2 Hz, 1H), 7.49-7.63 (m, 5H), 7.64-7.74 (m, 5H), 7.99 (s, 1H), 8.25 (dd, J=1.6, J=5.2 Hz, 1H), 8.28 (t, J=2 Hz, 1H), 8.92 (d, J=2 Hz, 1H), 9.03 (d, J=2 Hz, 1H).

Example 12

5-(3-Chloro-8-phenyl-1-(pyridin-2-ylmethylamino)isoquinolin-4-yl)nicotinic acid

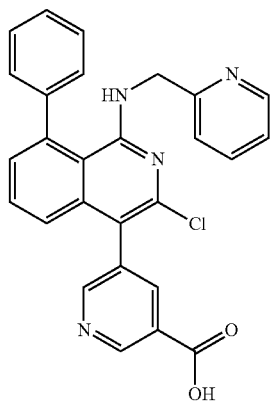

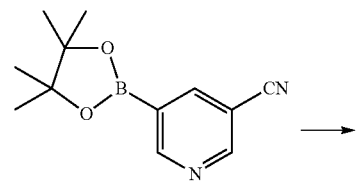

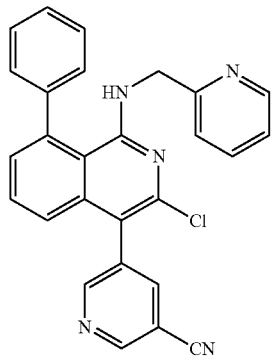

3-Chloro-4-iodo-8-phenyl-N-(pyridin-2-ylmethyl)isoquinolin-1-amine (0.10 g, 0.10 mmol) (prepared as described for Example 10) was converted into 5-(3-chloro-8-phenyl-1-((pyridin-2-ylmethyl)amino)isoquinolin-4-yl)nicotinonitrile using Suzuki cross coupling reaction as described for Example 1. Following reagents are utilized for the conversion: 3-(4,4,5,5-tetramethyl-1,3,2-dioxaborolan-2-yl)nicotinonitrile (0.040 g, 0.20 mmol), potassium carbonate (0.040 g, 0.30 mmol) and 1,1'-bis(diphenylphosphino)ferrocenepalladium(II)dichloride dichloromethane complex (0.02 g, 0.02 mmol). The resulting residue was purified by preparative HPLC (Condition B-70 described in general methods) to yield 5-(3-chloro-8-phenyl-1-((pyridin-2-ylmethyl)amino)isoquinolin-4-yl)nicotinonitrile (0.030 g, 30%). LCMS Method B-13: retention time 2.07 min, [M+1]= 448.20. HPLC Method B-2: retention time 9.20 min, Purity 98.03%. $^1$H NMR (400 MHz, DMSO-d$_6$) δ ppm: 4.41 (d, J=4.8 Hz, 2H), 5.51 (t, J=1.2 Hz, 1H), 6.99-7.01 (m, 2H), 7.23-7.28 (m, 2H), 7.41 (dd, J=8.8 Hz, J=1.2 Hz, 1H), 7.43-7.48 (m, 4H), 7.55 (dd, J=7.2 Hz, J=1.2 Hz, 1H), 7.75-7.82 (m, 2H), 8.33 (t, J=2.0 Hz, 1H), 8.97 (d, J=2.0 Hz, 1H), 9.17 (d, J=2.0 Hz, 1H).

466.20. HPLC Method B-5: retention time 6.28 min, Purity 97.48%. $^1$H NMR (400 MHz, DMSO-d$_6$) δ ppm: 4.54 (d, J=4.4 Hz, 2H), 6.61 (t, J=4.0 Hz, 1H), 7.19-7.32 (m, 4H), 7.50-7.54 (m, 5H), 7.63-7.73 (m, 3H), 8.21 (dd, J=0.8 Hz, J=3.2 Hz, 2H), 8.24 (t, J=2.0 Hz, 1H), 8.71 (d, J=2.4 Hz, 1H), 9.14 (d, J=2.0 Hz, 1H).

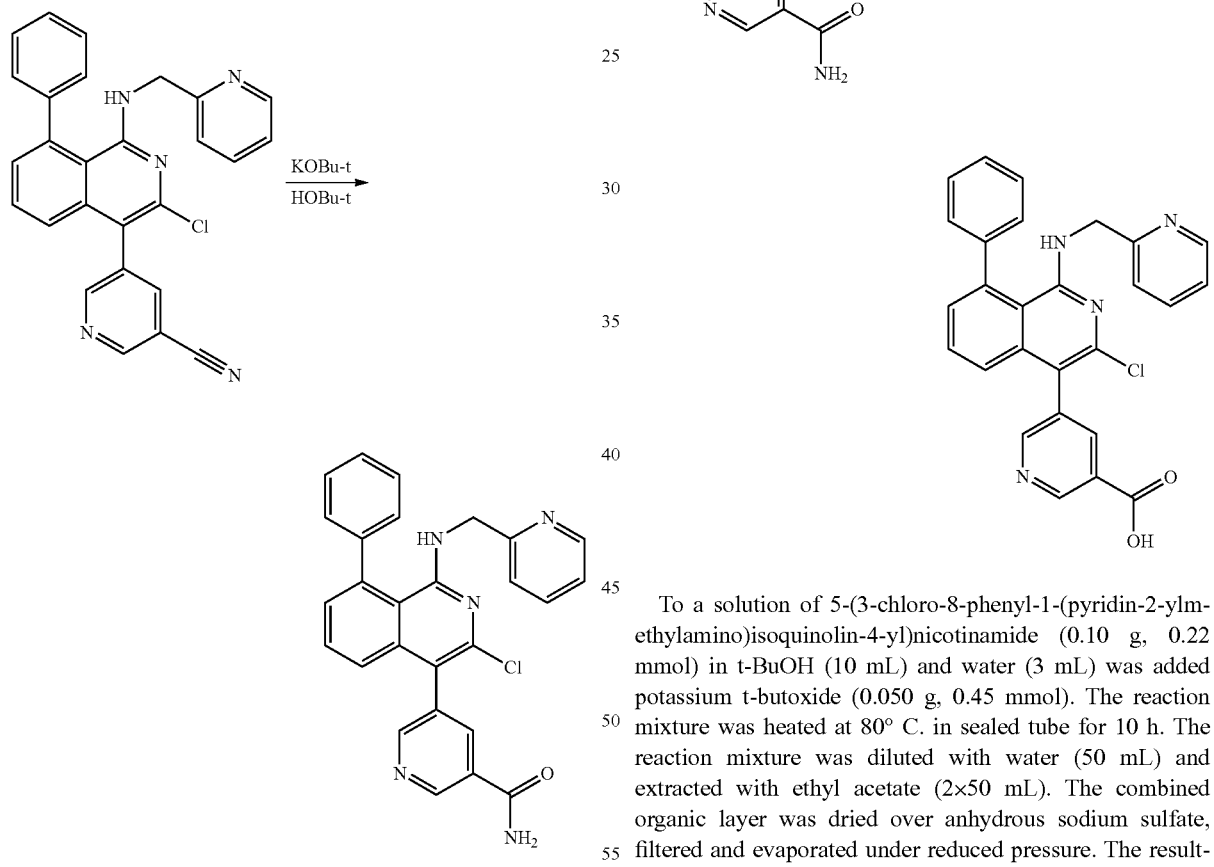

5-(3-Chloro-8-phenyl-1-((pyridin-2-ylmethyl)amino)isoquinolin-4-yl)nicotinonitrile (0.10 g, 0.22 mmol) was converted into 5-(3-chloro-8-phenyl-1-(pyridin-2-ylmethylamino)isoquinolin-4-yl)nicotinamide by following the procedure described for Example 9 using t-BuOH (10 mL) and potassium t-butoxide (0.05 g, 0.4 mmol) at 80° C. in a sealed tube for 10 h. The resulting residue was purified by preparative HPLC (Condition B-66 described in general methods) to yield 5-(3-chloro-8-phenyl-1-(pyridin-2-ylmethylamino)isoquinolin-4-yl)nicotinamide (0.010 g, 10%). LCMS Method B-17: retention time 2.29 min, [M+1]=

To a solution of 5-(3-chloro-8-phenyl-1-(pyridin-2-ylmethylamino)isoquinolin-4-yl)nicotinamide (0.10 g, 0.22 mmol) in t-BuOH (10 mL) and water (3 mL) was added potassium t-butoxide (0.050 g, 0.45 mmol). The reaction mixture was heated at 80° C. in sealed tube for 10 h. The reaction mixture was diluted with water (50 mL) and extracted with ethyl acetate (2×50 mL). The combined organic layer was dried over anhydrous sodium sulfate, filtered and evaporated under reduced pressure. The resulting residue was purified by preparative HPLC (Condition B-61 described in general methods) to yield 5-(3-chloro-8-phenyl-1-(pyridin-2-ylmethylamino)isoquinolin-4-yl)nicotinic acid (0.010 g, 16%). LCMS Method B-12 retention time 2.09 min, [M+1]=467.20. HPLC Method B-5: retention time 7.08 min, Purity 96.53%. $^1$H NMR (400 MHz, DMSO-d$_6$) δ ppm:4.54 (d, J=4.0 Hz, 2H), 6.58 (t, J=4.0 Hz, 1H), 7.19-7.24 (m, 4H), 7.50-7.53 (m, 5H), 7.63 (dd, J=7.2 Hz, J=8.4 Hz, 1H), 7.69 (dt, J=2.0 Hz, J=7.6 Hz, 1H), 8.15 (br s, 1H), 8.21 (d, J=4.4 Hz, 1H), 8.65 (br s, 1H), 9.11 (br s, 1H).

Example 13

N1-(3-(3-Chloro-8-phenyl-1-(pyridin-2-ylmethyl-amino)isoquinolin-4-yl)phenyl)malonamide

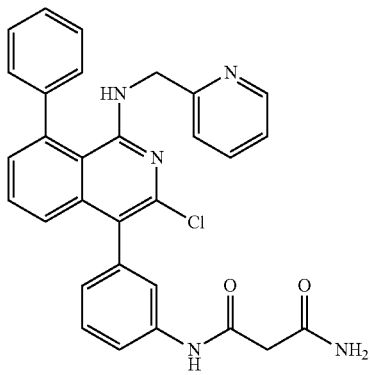

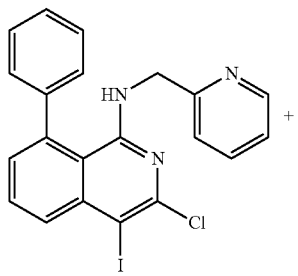

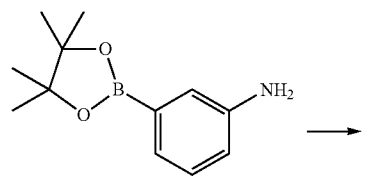

3-Chloro-4-iodo-8-phenyl-N-(pyridin-2-ylmethyl)isoquinolin-1-amine (0.500 g, 1.06 mmol), (prepared as described for Example 10) was converted into 4-(3-aminophenyl)-3-chloro-8-phenyl-N-(pyridin-2-ylmethyl)isoquinolin-1-amine using Suzuki cross coupling reaction as described for Example 1. Following reagents are utilized for the conversion: 3,3-(4,4,5,5-tetramethyl-1,3,2-dioxaborolan-2-yl)aniline (0.302 g, 1.38 mmol) potassium carbonate (0.439 g, 3.18 mmol) and 1,1'-bis(diphenylphosphino)ferrocene-palladium(II)dichloride dichloromethane complex (0.043 g, 0.053 mmol). The resulting residue was purified by silica gel column chromatography using CombiFlash (12 g REDISEP® column) with 50% ethyl acetate in hexane as an eluent to yield 4-(3-aminophenyl)-3-chloro-8-phenyl-N-(pyridin-2-ylmethyl)isoquinolin-1-amine (0.400 g, 86.0%). LCMS Method B-26: retention time 1.81 min, [M+1]=437.20. $^1$H NMR (400 MHz, DMSO-$d_6$) δ ppm: 4.51 (d, J=4.0 Hz, 2H), 5.22 (s, 2H), 6.34 (t, J=4.0 Hz, 1H), 6.7 (m, 2H), 6.96 (m, 2H), 7.20-7.27 (m, 3H), 7.40 (dd, J=8.4 Hz, J=1.2 Hz, 1H), 7.45-7.52 (m, 5H), 7.58 (m, 1H), 7.71 (dd, J=9.6 Hz, J=2.0 Hz, 1H), 8.21-8.23 (m, 1H).

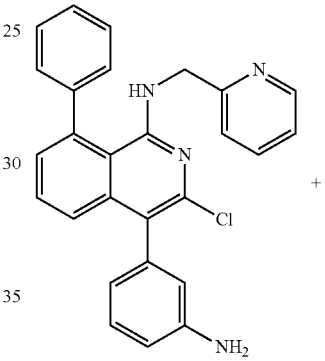

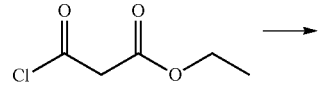

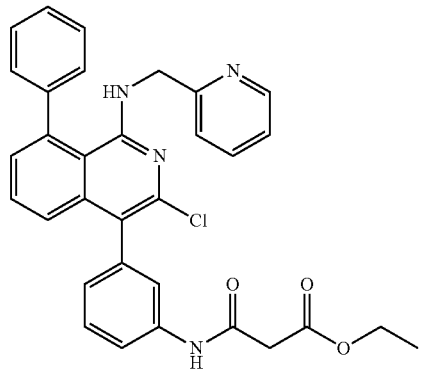

To a solution of 4-(3-aminophenyl)-3-chloro-8-phenyl-N-(pyridin-2-ylmethyl)isoquinolin-1-amine (0.100 g, 0.229 mmol) in CH$_2$Cl$_2$ (15 mL) was added pyridine (0.037 mL, 0.46 mmol) followed by ethyl malonyl chloride (0.052 g, 0.34 mmol) at room temperature. The reaction mixture was stirred for 2 h and was diluted with water (100 mL). The aqueous mixture was extracted into CH₂Cl₂ (2×50 mL). The combined organic layer was dried over anhydrous sodium sulfate, filtered and evaporated under reduced pressure to give a residue which was purified by preparative HPLC (Condition B-69 as described in general methods) to yield ethyl 3-(3-(3-chloro-8-phenyl-1-(pyridin-2-ylmethylamino) isoquinolin-4-yl)phenylamino)-3-oxopropanoate (0.060 g, 48%). LCMS Method B-17: retention time 2.45 min, [M+1]=551.20.

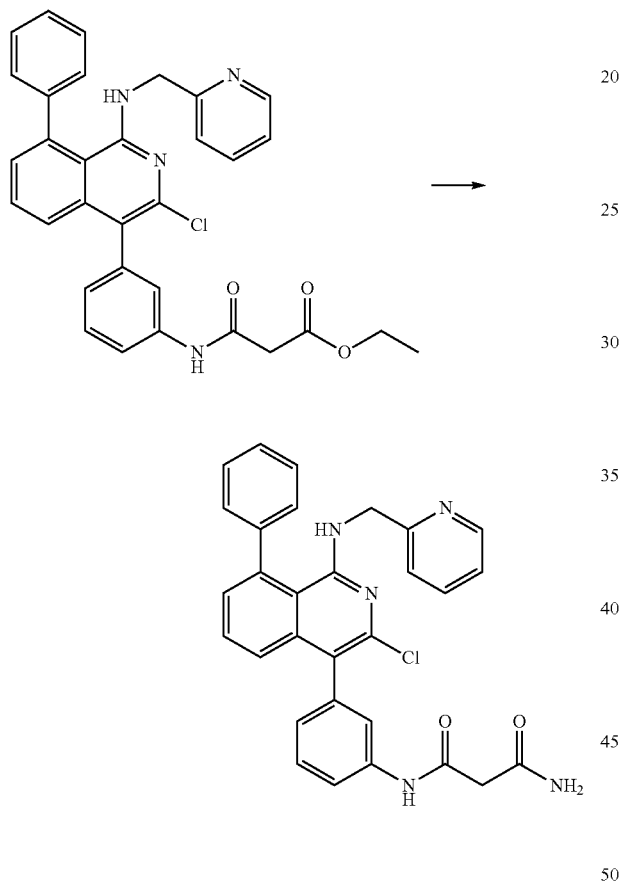

To a solution of ethyl 3-(3-(3-chloro-8-phenyl-1-(pyridin-2-ylmethylamino)isoquinolin-4-yl)phenylamino)-3-oxopropanoate (0.15 g, 0.37 mmol) in MeOH (15 mL) was purged with ammonia at −78° C. in a sealed tube for 10 min. The reaction mixture was stirred for 48 h at room temperature and concentrated to give crude residue. The crude residue was purified by preparative HPLC (Condition B-64 as described in general methods) to yield N1-(3-(3-chloro-8-phenyl-1-(pyridin-2-ylmethylamino)isoquinolin-4-yl)phenyl)malonamide (0.030 g, 20%). LCMS Method B-12: retention time 1.90 min, [M+1]=522.20. HPLC Method B-2: retention time 7.27 min, Purity 96.96%. ¹H NMR (400 MHz, DMSO-d₆) δ ppm: 2.13 (m, 3H), 4.64 (d, J=4.4 Hz, 2H), 6.08 (t, J=4.0 Hz, 1H), 7.19-7.27 (m, 3H), 7.46-7.51 (m, 5H), 7.66-7.71 (m, 3H), 7.90-7.92 (m, 1H), 8.27-8.28 (m, 2H), 8.72 (t, J=2.4 Hz, 1H), 8.77 (d, J=2.4 Hz, 1H), 9.01 (s, 1H), 10.21 (s, 1H).

Example 14

5-(1-(Benzylamino)-3-methyl-8-phenylisoquinolin-4-yl)pyridine-3-sulfonamide

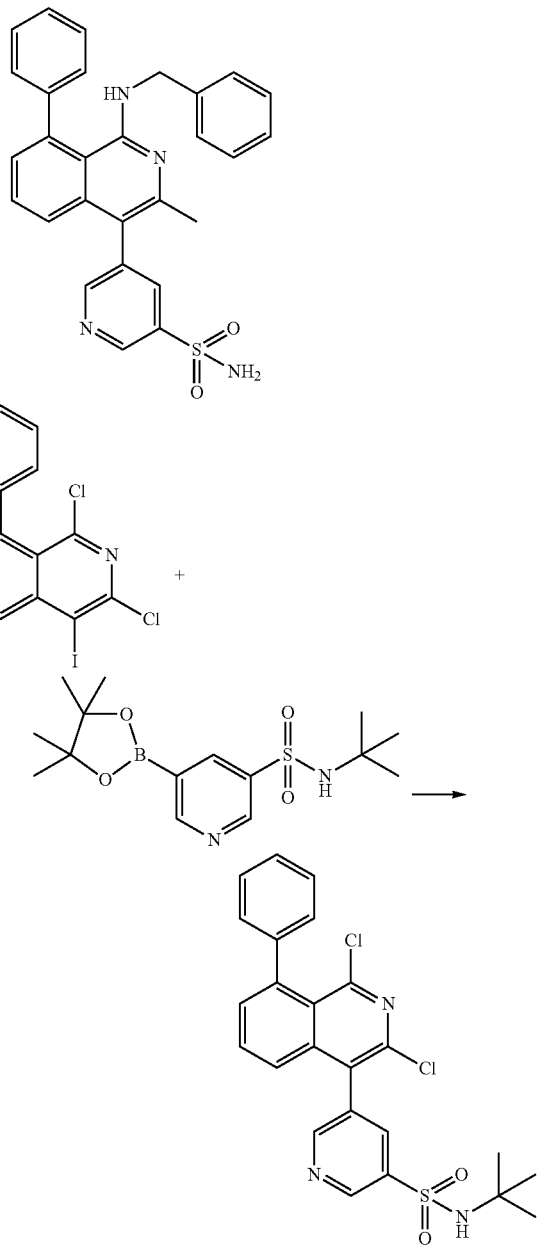

1,3-Chloro-4-iodo-8-phenylisoquinoline (0.20 g, 0.50 mmol) (prepared as described in Example 7) was converted into N-tert-butyl-5-(1,3-dichloro-8-phenylisoquinolin-4-yl) pyridine-3-sulfonamide using Suzuki cross coupling reaction as described for Example 1. Following reagents are utilized for the conversion: N-(tert-butyl)-5-(4,4,5,5-tetramethyl-1,3,2-dioxaborolan-2-yl)pyridine-3-sulfonamide (0.22 g, 0.64 mmol), potassium carbonate (0.18 g, 1.3 mmol) and 1,1'-bis(diphenylphosphino)ferrocene-palladium(II)dichloride dichloromethane complex (0.02 g, 0.02 mmol). The resulting residue was purified by silica gel column chromatography using CombiFlash (12 g REDISEP® column) with 50% ethyl acetate in hexane as an eluent to yield N-tert-butyl-5-(1,3-dichloro-8-phenylisoquinolin-4-yl)pyridine-3-sulfonamide (0.12 g, 55%). LCMS Method B-40: retention time 0.91 min, [M+1]=572.60. $^1$H NMR (400 MHz, DMSO-$d_6$) δ ppm: 1.16 (s, 9H), 7.40-7.42 (m, 3H), 7.49 (t, J=4.8 Hz, 3H), 7.69 (dd, J=0.8 Hz, J=7.2 Hz, 1H), 7.87-7.92 (m, 2H), 8.35 (t, J=2.0 Hz, 1H), 8.92 (d, J=1.6 Hz, 1H), 9.18 (d, J=2.0 Hz, 1H).

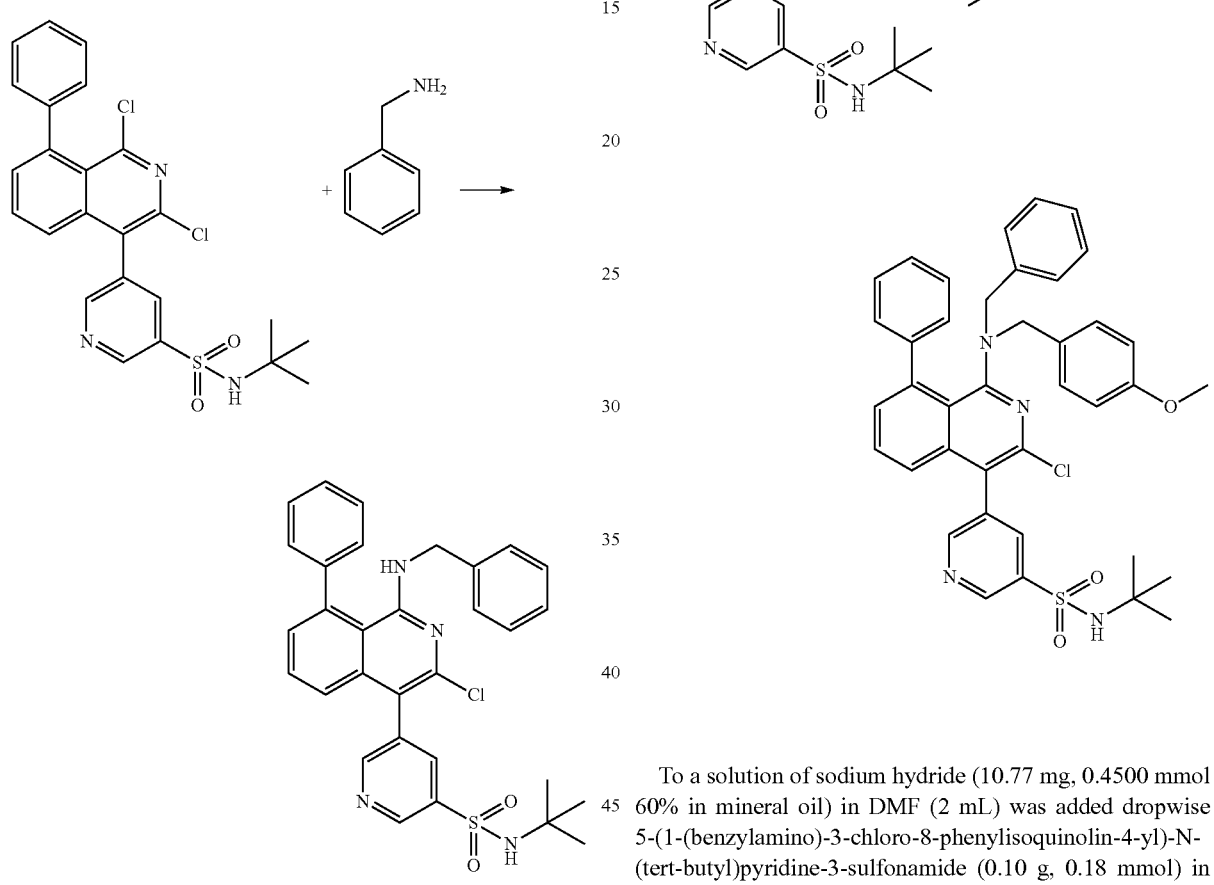

To a solution of N-(tert-butyl)-5-(1,3-dichloro-8-phenylisoquinolin-4-yl)pyridine-3-sulfonamide (0.100 g, 0.200 mmol) and benzyl amine (0.135 g, 1.26 mmol) in 1,4-dioxane (10 mL) was heated in a sealed tube at 100° C. for 12 h. The reaction mixture was allowed to cool to room temperature and diluted with saturated sodium bicarbonate solution (300 mL) and extracted with ethyl acetate (3×300 mL), the combined organic layer was washed with brine solution (100 mL), dried over sodium sulfate, filtered and concentrated under reduced pressure to give a residue which was purified by silica gel column chromatography using CombiFlash (12 g REDISEP® column) with 30% hexane in ethyl acetate as an eluent to yield 5-(1-(benzylamino)-3-chloro-8-phenylisoquinolin-4-yl)-N-tert-butylpyridine-3-sulfonamide (0.080 g, 70%). LCMS Method B-12: retention time 2.30 min, [M+1]=557.20.

To a solution of sodium hydride (10.77 mg, 0.4500 mmol 60% in mineral oil) in DMF (2 mL) was added dropwise 5-(1-(benzylamino)-3-chloro-8-phenylisoquinolin-4-yl)-N-(tert-butyl)pyridine-3-sulfonamide (0.10 g, 0.18 mmol) in DMF (5 mL) at 0° C., followed by 4-methoxybenzyl chloride (0.02 mL, 0.2 mmol). The reaction mixture was allowed to stir at room temperature for 30 min. The reaction mixture was quenched with saturated ammonium chloride solution (15 mL) at 0° C. and extracted with ethyl acetate (2×50 mL). The combined organic layer was dried over anhydrous sodium sulfate, filtered and evaporated under reduced pressure to give a residue which was purified by silica gel column chromatography using CombiFlash (12 g REDISEP® column) with 35% ethyl acetate in hexane as an eluent to yield 5-(1-(benzyl(4-methoxybenzyl)amino)-3-chloro-8-phenylisoquinolin-4-yl)-N-(tert-butyl)pyridine-3-sulfonamide (0.050 g, 40%). LCMS Method B-40: retention time 1.44 min, [M+1]=677.43. $^1$H NMR (400 MHz, DMSO-$d_6$) δ ppm:1.18 (s, 9H), 3.72 (s, 3H), 3.95-4.03 (m, 4H), 6.60-6.90 (m, 6H), 7.20-7.75 (m, 11H), 7.88 (br s, 1H), 8.27 (br s, 1H), 8.87 (br s, 1H), 9.11 (d, J=2.4 Hz, 1H).

(m, 4H), 6.51-6.81 (m, 6H), 7.16-7.24 (m, 6H), 7.42-7.73 (m, 6H), 8.20 (br s, 1H), 8.83 (d, J=1.6 Hz, 1H), 9.09 (d, J=2.4 Hz, 1H).

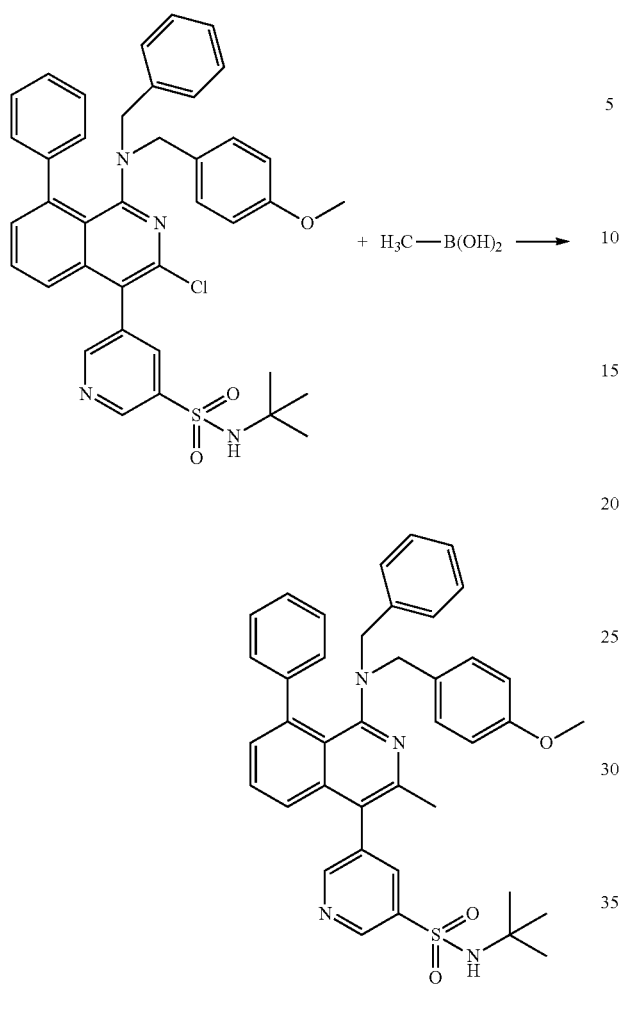

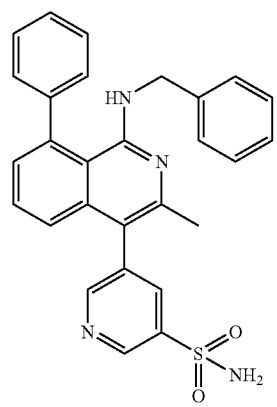

A solution of 5-(1-(benzyl(4-methoxybenzyl)amino)-3-chloro-8-phenylisoquinolin-4-yl)-N-(tert-butyl)pyridine-3-sulfonamide (0.15 g, 0.22 mmol), dihydroxymethylborane (0.04 g, 0.7 mmol) and potassium carbonate (0.09 g, 0.7 mmol) in 1,4-dioxane/water (10/3 mL) was purged with nitrogen for 30 min. To this solution was added 1,1'-bis(diphenylphosphino)ferrocene-palladium(II)dichloride dichloromethane complex (0.01 g, 0.01 mmol). The reaction mixture was heated at 100° C. in a sealed tube for 12 h. The reaction mixture was allowed to cool to room temperature and filtered through a pad of CELITE®. The filtrate was washed with water (50 mL) and extracted with ethyl acetate (100 mL). The organic layer was dried over anhydrous sodium sulfate, filtered and evaporated under reduced pressure to give a residue which was purified by silica gel column chromatography using CombiFlash (12 g REDISEP® column) with 30% ethyl acetate in hexane as an eluent to yield 5-(1-(benzyl(4-methoxybenzyl)amino)-3-methyl-8-phenylisoquinolin-4-yl)-N-(tert-butyl)pyridine-3-sulfonamide (0.10 g, 59%). LCMS Method B-18: retention time 2.68 min, [M+1]=657.20. $^1$H NMR (400 MHz, DMSO-d$_6$) δ ppm:1.19 (s, 9H), 2.26 (s, 3H), 3.74 (s, 3H), 3.85-4.03

5-(1-(Benzyl(4-methoxybenzyl)amino)-3-methyl-8-phenylisoquinolin-4-yl)-N-(tert-butyl)pyridine-3-sulfonamide (0.10 g, 0.15 mmol) was dissolved in TFA (10 mL) and stirred at 70° C. for 2 h. TFA was removed under reduced pressure and the reaction mixture was diluted with saturated sodium bicarbonate (100 mL). The aqueous mixture was extracted with ethyl acetate (3×30 mL). The combined organic extracts were dried over anhydrous sodium sulfate and evaporated under reduced pressure to give a residue which was purified by preparative HPLC (Condition B-68 as mentioned in general methods) to yield 5-(1-(benzylamino)-3-methyl-8-phenylisoquinolin-4-yl)pyridine-3-sulfonamide (0.02 g, 20%). LCMS Method B-18: retention time 2.37 min, [M+1]=481.20. HPLC Method B-5: retention time 7.05 min, Purity 99.83%. $^1$H NMR (400 MHz, DMSO-d$_6$) δ ppm: 2.19 (s, 3H), 4.43 (d, J=4.8 Hz, 2H), 5.13 (t, J=4.8 Hz, 1H), 7.01 (dd, J=1.2 Hz, J=7.2 Hz, 2H), 7.12 (dd, J=0.8 Hz, J=8.8 Hz, 1H), 7.21-7.27 (m, 4H), 7.41-7.56 (m, 5H), 7.51-7.67 (m, 3H), 8.12 (t, J=2 Hz, 1H), 8.75 (d, J=2 Hz, 1H), 9.06 (d, J=2.4 Hz, 1H).

Example 15

5-(1-(Benzylamino)-8-phenylisoquinolin-4-yl)pyridine-3-sulfonamide

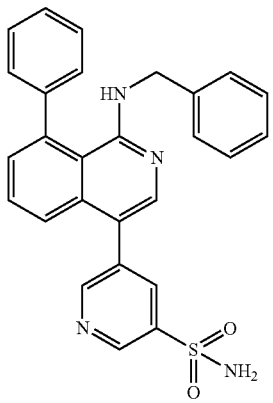

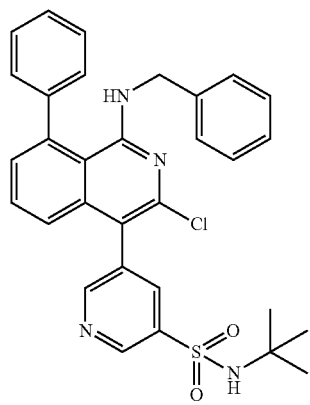

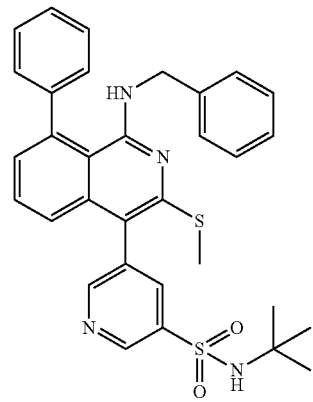

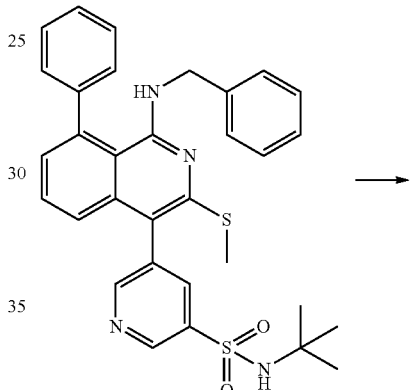

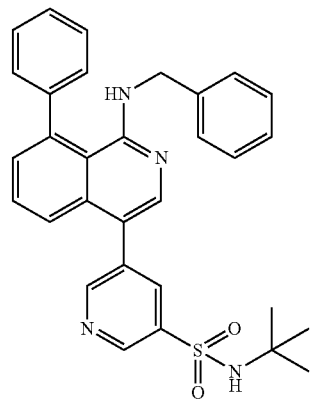

To a solution of 5-(1-(benzylamino)-3-chloro-8-phenylisoquinolin-4-yl)-N-(tert-butyl)pyridine-3-sulfonamide described in Example 14, (0.30 g, 0.54 mmol) in DMF (10 mL) was added sodium methyl mercaptide (0.08 g, 1 mmol) and the reaction mixture was heated at 100° C. for 12 h. The reaction mixture was allowed to cool to room temperature and diluted with cold water (50 mL). The aqueous solution was extracted with ethyl acetate (2×50 mL). The combined organic layer was washed with saturated brain solution, dried over anhydrous sodium sulfate, filtered and evaporated under reduced pressure to give a residue which was purified by silica gel column chromatography using CombiFlash (12 g REDISEP® column) with 40% ethyl acetate in hexane as an eluent to yield 5-(1-(benzylamino)-3-(methylthio)-8-phenylisoquinolin-4-yl)-N-(tert-butyl)pyridine-3-sulfonamide (0.20 g, 65%). LCMS Method B-40: retention time 1.39 min, [M+1]=569.42. $^1$H NMR (400 MHz, DMSO-$d_6$) δ ppm: 1.18 (s, 9H), 2.39 (s, 3H), 4.49 (d, J=4.8 Hz, 2H), 5.35 (t, J=5.2 Hz, 1H), 6.98-7.05 (m, 3H), 7.17-7.57 (m, 10H), 7.84 (s, 1H), 8.12 (dd, J=2.0, J=2.4 Hz, 1H), 8.72 (d, J=2.0 Hz, 1H), 9.05 (d, J=2.0 Hz, 1H).

To a solution of 5-(1-(benzylamino)-3-(methylthio)-8-phenylisoquinolin-4-yl)-N-(tert-butyl)pyridine-3-sulfonamide (0.20 g, 0.35 mmol) in ethanol (15 mL) was added Raney nickel (0.50 g) and ammonium hydroxide solution (30%, 5 mL). The reaction mixture was stirred at 70° C. under hydrogen pressure (5 kg/cm$^2$) in an autoclave for 10 h. The reaction mixture was filtered through a pad of CELITE® and the CELITE® washed with methanol (30 mL). The filtrate was evaporated under reduced pressure to give the 5-(1-(benzylamino)-8-phenylisoquinolin-4-yl)-N-tert-butylpyridine-3-sulfonamide (0.10 g, 54%) which was taken to the next step without further purification. LCMS Method B-40: retention 1.27 min, [M+1]=523.45.

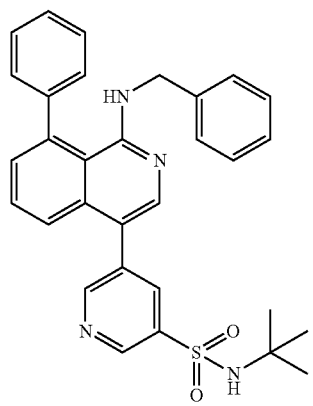

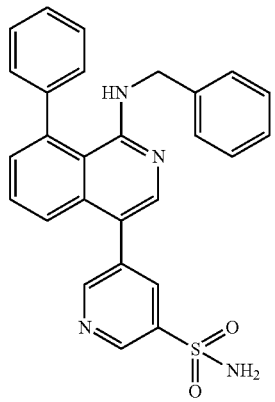 [SMILES: NS(=O)(=O)c1cncc(-c2cnc(NCc3ccccn3)c3c(-c4ccccc4)cccc23)c1]

5-(1-(Benzylamino)-8-phenylisoquinolin-4-yl)-N-(tert-butyl)pyridine-3-sulfonamide (0.10 g, 0.19 mmol) was converted to 5-(1-(benzylamino)-8-phenylisoquinolin-4-yl)pyridine-3-sulfonamide following the procedure described for Example 14 using TFA (10 mL) at 70° C. for 2 h. The resulting residue was purified by preparative HPLC (Method B-54 described in general methods) to yield 5-(1-(benzylamino)-8-phenylisoquinolin-4-yl)pyridine-3-sulfonamide (0.040 g, 50%). LCMS Method B-13: retention time 1.97 min, [M+1]=466.80. HPLC Method B-5: retention time 6.46 min, Purity 98.79%. $^1$H NMR (400 MHz, DMSO-$d_6$) δ ppm: 4.42 (d, J=5.2 Hz, 2H), 5.22 (t, J=5.2 Hz, 1H), 6.98 (dd, J=1.6 Hz, J=7.6 Hz, 2H), 7.21-7.27 (m, 3H), 7.36 (dd, J=1.6 Hz, J=7.2 Hz, 1H), 7.41-7.48 (m, 5H), 7.64-7.73 (m, 4H), 7.97 (s, 1H), 8.27 (t, J=2.4 Hz, 1H), 8.90 (d, J=2.0 Hz, 1H), 9.03 (d, J=2.0 Hz, 1H).

Example 16

5-(1-(Benzylamino)-3-cyano-8-phenylisoquinolin-4-yl)pyridine-3-sulfonamide

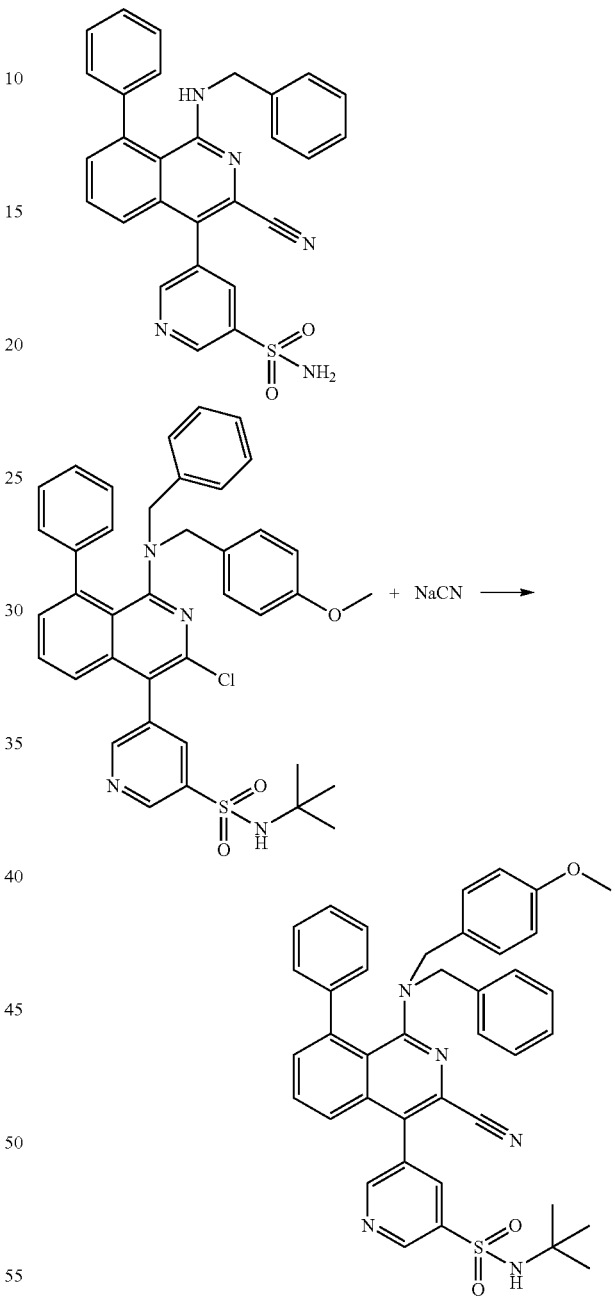

To a solution of 5-(1-(benzyl(4-methoxybenzyl)amino)-3-chloro-8-phenylisoquinolin-4-yl)-N-(tert-butyl)pyridine-3-sulfonamide (0.20 g, 0.29 mmol) (prepared as described for Example 14) in DMF (15 mL) was added sodium cyanide (0.07 g, 1 mmol). The reaction mixture was heated at 100° C. for 12 h and was allowed to cool to room temperature. The reaction mixture was diluted with cold water (100 mL) and extracted with ethyl acetate (2×50 mL). The combined organic layer was washed with brine solution (50 mL), and dried over anhydrous sodium sulfate, filtered and evaporated under reduced pressure to give a residue which was purified by silica gel column chromatography using CombiFlash (12 g REDISEP® column) with 30% ethyl acetate in hexane to yield 5-(1-(benzyl(4-methoxybenzyl)amino)-3-cyano-8-phenylisoquinolin-4-yl)-N-(tert-butyl)pyridine-3-sulfonamide (0.12 g, 60%). LCMS Method B-40: retention time 1.39 min, [M+1]=668.55. $^1$H NMR (400 MHz, DMSO-d$_6$): δ 1.18 (s, 9H), 3.71 (s, 3H), 3.90-4.08 (m, 4H), 5.76-6.76 (m, 6H), 7.19-7.21 (m, 3H), 7.43-7.51 (m, 6H), 7.71-7.92 (m, 3H), 8.45 (br s, 1H), 9.02 (d, J=1.6 Hz, 1H), 9.19 (br s, 1H).

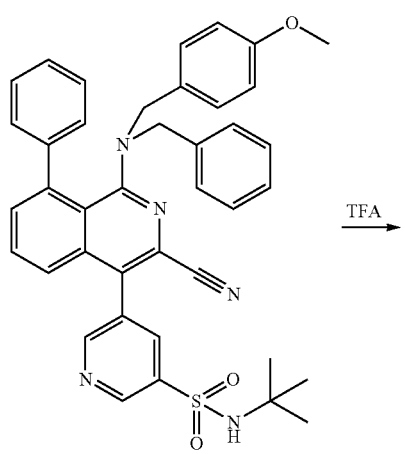

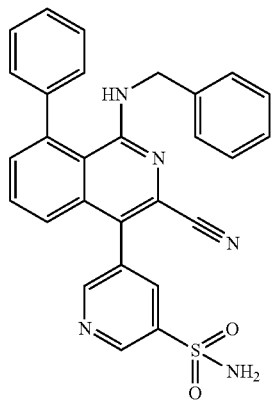

5-(1-(Benzyl(4-methoxybenzyl)amino)-3-cyano-8-phenylisoquinolin-4-yl)-N-(tert-butyl)pyridine-3-sulfonamide (0.10 g, 0.15 mmol) was converted into 5-(1-(benzylamino)-3-cyano-8-phenylisoquinolin-4-yl)pyridine-3-sulfonamide by following the procedure described in Example 14 using TFA (10 mL) at 70° C. for 2 h. The resulting residue was purified by preparative HPLC (Condition B-64 described in general methods) to yield 5-(1-(benzylamino)-3-cyano-8-phenylisoquinolin-4-yl)pyridine-3-sulfonamide (0.03 g, 40%). LCMS Method B-26: retention time 2.60 min, [M+1]=492.00. HPLC Method B-5: retention time 20.28 min, Purity 99.57%. $^1$H NMR (400 MHz, DMSO-d$_6$): δ 4.42 (d, J=4.80 Hz, 2H), 5.00 (t, J=5.20 Hz, 1H), 6.99-7.00 (m, 2H), 7.00-7.01 (m, 3H), 7.01-7.48 (m, 6H), 7.53-7.56 (m, 1H), 7.75-7.81 (m, 3H), 8.33 (s, 1H), 8.92 (s, 1H), 9.14 (s, 1H).

Example 17

1-(Benzylamino)-8-phenyl-4-(5-sulfamoylpyridin-3-yl)isoquinoline-3-carboxamide

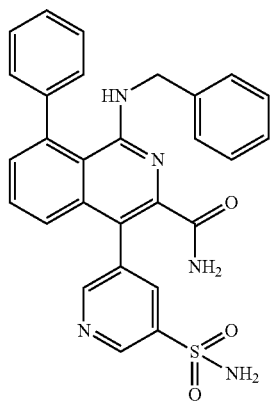 [SMILES: NC(=O)c1nc(NCc2ccccc2)c2c(-c3ccccc3)cccc2c1-c1cncc(S(N)(=O)=O)c1]

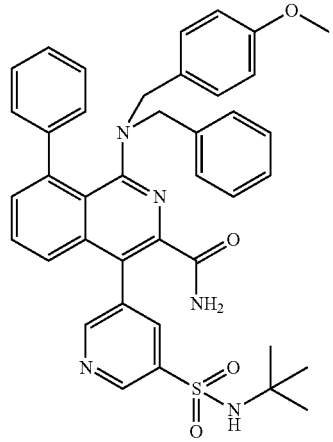

5-(1-(Benzyl(4-methoxybenzyl)amino)-3-cyano-8-phenylisoquinolin-4-yl)-N-(tert-butyl)pyridine-3-sulfonamide (0.10 g, 0.15 mmol) was converted to 1-(benzyl(4-methoxybenzyl)amino)-4-(5-(N-(tert-butyl)sulfamoyl)pyridin-3-yl)-8-phenylisoquinoline-3-carboxamide in t-BuOH (15 mL) using potassium tert-butoxide (0.04 g, 0.4 mmol) in a sealed tube at 85° C. for 12 h by following the procedure described in Example 12. The resulting residue 1-(benzyl(4-methoxybenzyl)amino)-4-(5-(N-(tert-butyl)sulfamoyl)pyridin-3-yl)-8-phenylisoquinoline-3-carboxamide (0.090 g, 70%) was taken to the next step without purification. LCMS Method B-40: retention time 0.90 min, [M+1]=686.62.

Example 18

5-(3-Chloro-8-phenyl-1-(1-phenylethylamino)isoquinolin-4-yl)pyridine-3-sulfonamide

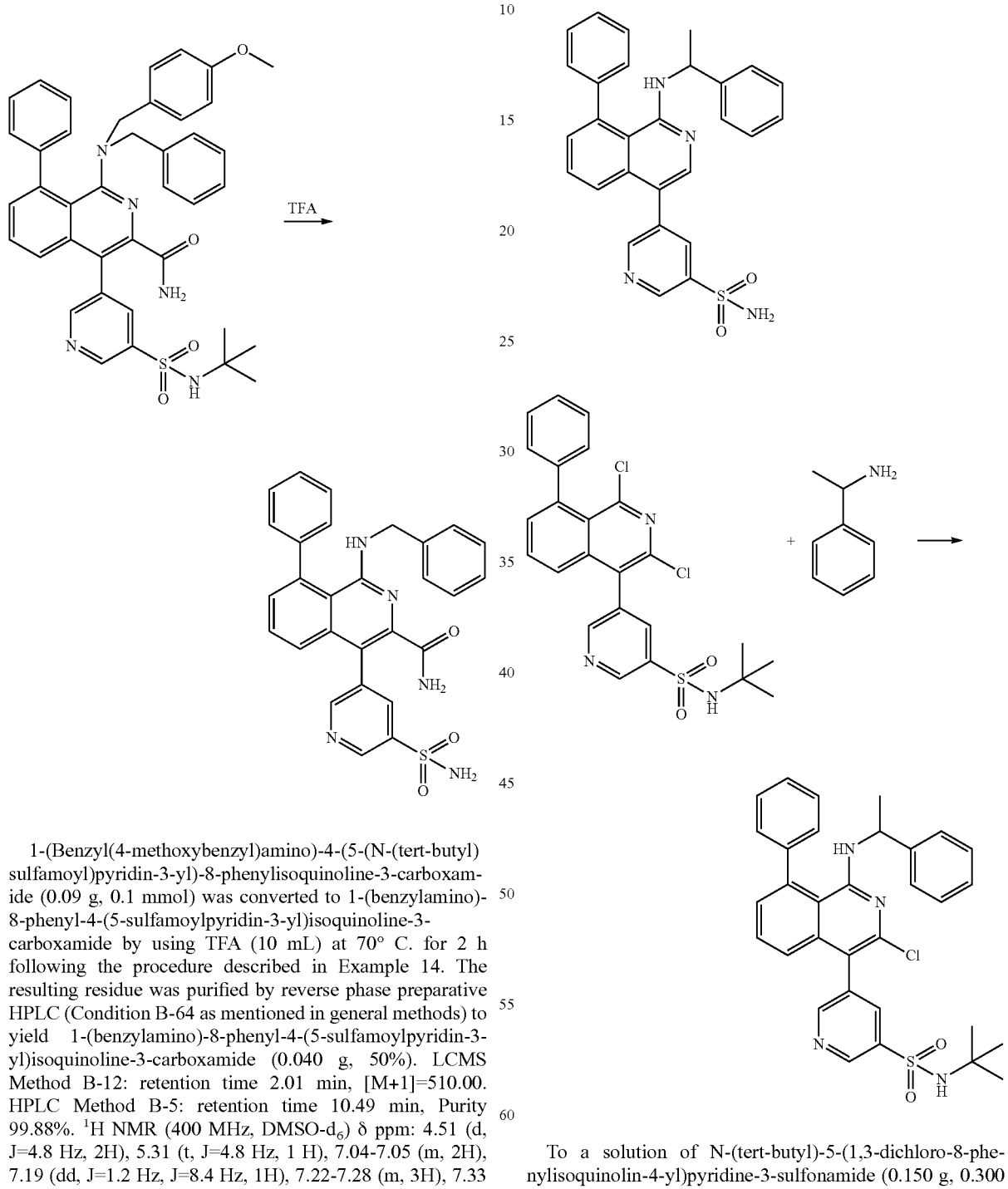

1-(Benzyl(4-methoxybenzyl)amino)-4-(5-(N-(tert-butyl)sulfamoyl)pyridin-3-yl)-8-phenylisoquinoline-3-carboxamide (0.09 g, 0.1 mmol) was converted to 1-(benzylamino)-8-phenyl-4-(5-sulfamoylpyridin-3-yl)isoquinoline-3-carboxamide by using TFA (10 mL) at 70° C. for 2 h following the procedure described in Example 14. The resulting residue was purified by reverse phase preparative HPLC (Condition B-64 as mentioned in general methods) to yield 1-(benzylamino)-8-phenyl-4-(5-sulfamoylpyridin-3-yl)isoquinoline-3-carboxamide (0.040 g, 50%). LCMS Method B-12: retention time 2.01 min, [M+1]=510.00. HPLC Method B-5: retention time 10.49 min, Purity 99.88%. $^1$H NMR (400 MHz, DMSO-$d_6$) δ ppm: 4.51 (d, J=4.8 Hz, 2H), 5.31 (t, J=4.8 Hz, 1 H), 7.04-7.05 (m, 2H), 7.19 (dd, J=1.2 Hz, J=8.4 Hz, 1H), 7.22-7.28 (m, 3H), 7.33 (s, 1H), 7.39 (dd, J=1.2 Hz, J=7.2 Hz, 1H), 7.44-7.50 (m, 6H), 7.67 (dd, J=7.2 Hz, J=8.4 Hz, 2H), 7.88 (br s, 1H), 7.98 (t, J=2.0 Hz, 1H), 8.61 (d, J=2.0 Hz, 1H), 8.98 (d, J=2.4 Hz, 1H).

To a solution of N-(tert-butyl)-5-(1,3-dichloro-8-phenylisoquinolin-4-yl)pyridine-3-sulfonamide (0.150 g, 0.300 mmol) (prepared in Example 14) and α-methylbenzylamine (0.135 g, 0.920 mmol) in 1,4-dioxane (10 mL) was heated in a sealed tube at 100° C. for 12 h. The reaction mixture was allowed to cool to room temperature and diluted with saturated sodium bicarbonate solution (300 mL) and extracted with ethyl acetate (3×300 mL), the combined organic layer was washed with brine solution (100 mL) and dried over sodium sulfate, filtered and concentrated under reduced pressure. The resulting residue was purified by silica gel column chromatography using CombiFlash (12 g REDISEP® column) with 30% hexane in ethyl acetate as an eluent to yield N-tert-butyl-5-(3-chloro-8-phenyl-1-(1-phenylethylamino)isoquinolin-4-yl)pyridine-3-sulfonamide (0.12 g, 63%). LCMS Method B-12: retention time 2.31 min, [M+H]=572.2.

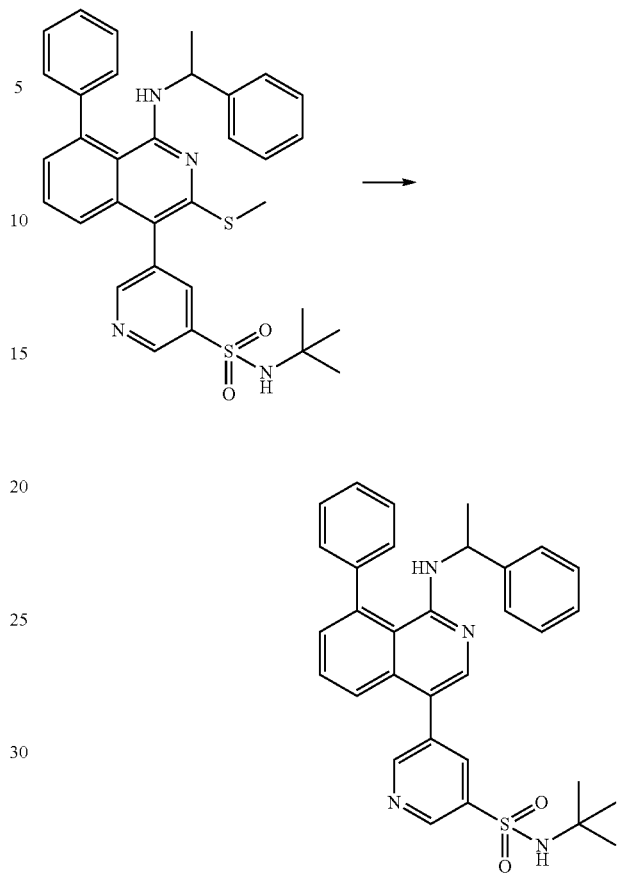

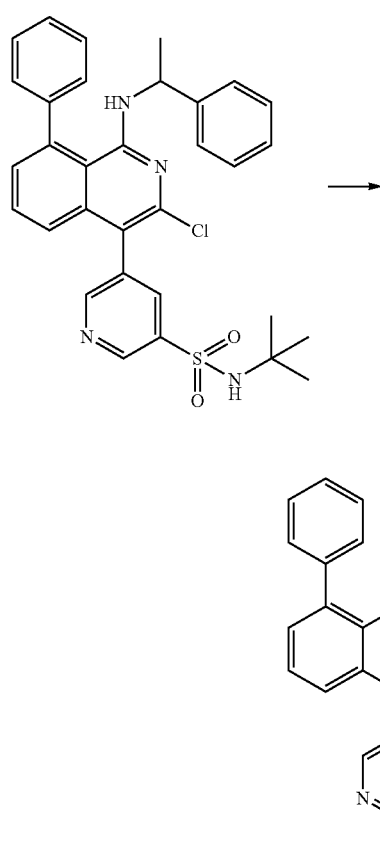

N-(tert-Butyl)-5-(3-(methylthio)-8-phenyl-1-((1-phenylethyl)amino)isoquinolin-4-yl)pyridine-3-sulfonamide (0.25 g, 0.43 mmol) was converted to N-(tert-butyl)-5-(8-phenyl-1-((1-phenylethyl)amino)isoquinolin-4-yl)pyridine-3-sulfonamide using Raney nickel (0.50 g) and ammonia solution (30%, 5 mL) in ethanol (70 mL), at 70° C. under hydrogen pressure (5 kg/cm$^2$) in autoclave for 12 h by following the procedure described in Example 15. N-(tert-Butyl)-5-(8-phenyl-1-((1-phenylethyl)amino)isoquinolin-4-yl)pyridine-3-sulfonamide (0.18 g, 66%) was taken to the next step without further purification. LCMS Method B-12: retention time 2.42 min, [M+1]=537.20.

N-(tert-Butyl)-5-(3-chloro-8-phenyl-1-((1-phenylethyl)amino)isoquinolin-4-yl)pyridine-3-sulfonamide (0.38 g, 0.66 mmol) was converted to N-(tert-butyl)-5-(3-(methylthio)-8-phenyl-1-((1-phenylethyl)amino)isoquinolin-4-yl)pyridine-3-sulfonamide using sodium methyl mercaptide (0.09 g, 1 mmol) in DMF at 100° C. for 12 h by following the procedure in Example 15. The crude product was purified by silica gel column chromatography using CombiFlash (12 g REDISEP® column) with 40% ethyl acetate in hexane as an eluent to yield N-(tert-butyl)-5-(3-(methylthio)-8-phenyl-1-((1-phenylethyl)amino)isoquinolin-4-yl)pyridine-3-sulfonamide (0.25 g, 64%). LCMS Method B-40: retention time 1.41 min, [M+1]=583.46.

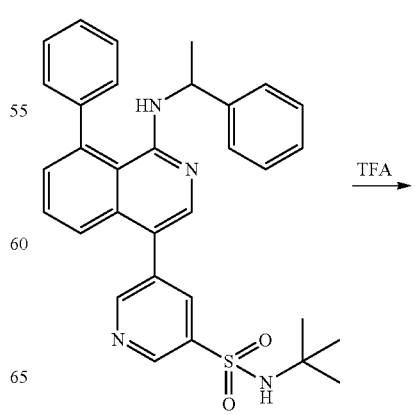

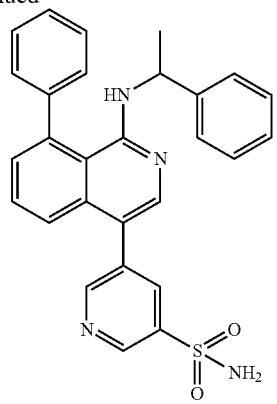

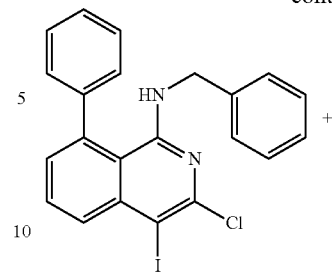

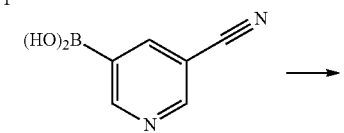

N-(tert-Butyl)-5-(8-phenyl-1-((1-phenylethyl)amino)isoquinolin-4-yl)pyridine-3-sulfonamide (0.12 g, 0.22 mmol) was converted to 5-(8-phenyl-1-((1-phenylethyl)amino)isoquinolin-4-yl)pyridine-3-sulfonamide using TFA (10 mL) at 70° C. for 2 h following the procedure described for Example 14. The resulting residue was purified by preparative HPLC (Condition B-66 described in general methods) and the racemate was separated into the enantiomers by SFC (Method B-52 described in methods). LCMS Method B-12: retention time 2.11 min, [M+1]=481.00. HPLC Method B-6: retention time 8.70 min, Purity 96.70%.

5-(8-Phenyl-1-((1-phenylethyl)amino)isoquinolin-4-yl)pyridine-3-sulfonamide (0.03 g, 28%) (Isomer-I): LCMS Method B-12: Retention time 2.11 min, [M+1]=481.20. Chiral HPLC Method B-81: Retention time 2.46 min, Purity 100%.

5-(8-Phenyl-1-((1-phenylethyl)amino)isoquinolin-4-yl)pyridine-3-sulfonamide (0.03 g, 28%). (Isomer-II): LCMS Method B-12: Retention time 2.12 min, [M+1]=481.20. Chiral HPLC Method B-81: Retention time 4.06 min, Purity 99.45%.

$^1$H NMR (400 MHz, DMSO-d$_6$) δ ppm:1.04 (d, J=6.8 Hz, 3H), 5.13 (t, J=6.8 Hz, 1H), 5.25 (d, J=6.8 Hz, 1H), 6.98-7.02 (m, 2H), 7.15-7.25 (m, 3H), 7.37 (dd, J=1.6 Hz, J=7.2 Hz, 1H), 7.57-7.64 (m, 8H), 7.69-7.73 (m, 1H), 7.87 (s, 1H). 8.23 (t, J=2.0 Hz, 1H), 8.87 (d, J=2.0 Hz, 1H), 9.01 (d, J=2.0 Hz, 1H).

Example 19

4-(5-(2H-Tetrazol-5-yl)pyridin-3-yl)-N-benzyl-8-phenylisoquinolin-1-amine

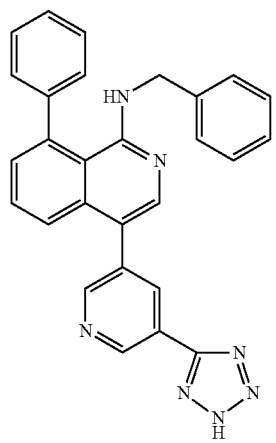

N-Benzyl-3-chloro-4-iodo-8-phenylisoquinolin-1-amine was prepared using the general procedures described for Example 10, (1.01 g, 2.12 mmol) was converted into 5-(1-(benzylamino)-3-chloro-8-phenylisoquinolin-4-yl)nicotinonitrile using Suzuki cross coupling reaction described for Example 1. Following reagents are utilized for the conversion: 5-cyanopyridin-3-ylboronic acid (0.33 g, 2.5 mmol), potassium carbonate (0.58 g, 4.2 mmol) and 1,1'-bis(diphenylphosphino)ferrocene-palladium(II)dichloride dichloromethane complex (0.15 g, 0.21 mmol). The resulting residue was purified by silica gel column chromatography using CombiFlash (12 g REDISEP® column) with 50% ethyl acetate in hexane as an eluent to yield 5-(1-(benzylamino)-3-chloro-8-phenylisoquinolin-4-yl)nicotinonitrile (0.52 g, 55%). LCMS Method B-40: retention time 1.38 min, [M+1]=447.40. $^1$H NMR (400 MHz, DMSO-d$_6$) δ ppm: 4.40 (d, J=4.4 Hz, 2H), 5.37 (t, J=5.0 Hz, 1H), 7.00-7.02 (m, 2H), 7.21-7.29 (m, 5H), 7.31-7.47 (m, 4H), 7.67-7.71 (m, 2H), 8.35 (s, 1H), 8.92 (m, 1H), 9.19 (d, J=2.0 Hz, 1H).

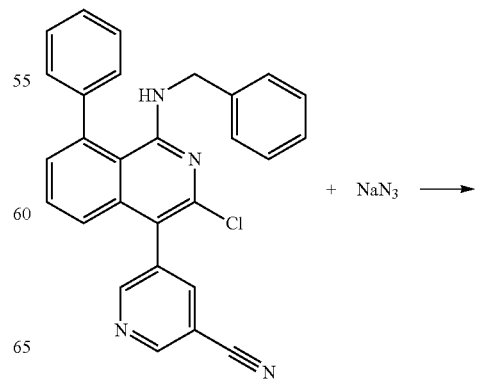

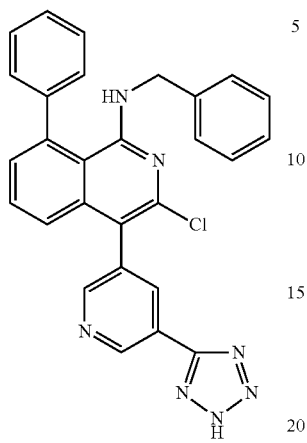

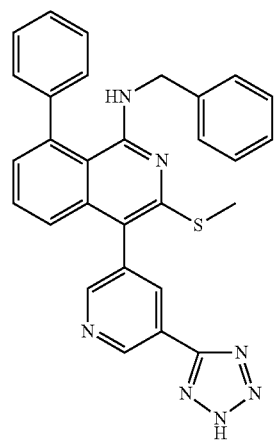

To a solution of 5-(1-(benzylamino)-3-chloro-8-phenylisoquinolin-4-yl)nicotinonitrile (0.41 g, 0.89 mmol) in DMF (3 mL) was added sodium azide (0.116 g, 1.79 mmol). The reaction mixture was heated at 100° C. for 12 h. The reaction mixture was concentrated under reduced pressure and diluted with water (50 mL) and extracted with ethyl acetate (2×50 mL). The combined organic layer was dried over anhydrous sodium sulfate, filtered and evaporated under reduced pressure to give the crude product. The resulting residue was purified by preparative HPLC (Method B-62 described in general methods) to yield 4-(5-(2H-tetrazol-5-yl)pyridin-3-yl)-N-benzyl-3-chloro-8-phenylisoquinolin-1-amine (0.31 g, 71%). LCMS Method B-12 retention time 2.74 min, [M+1]=490.20. $^1$H NMR (400 MHz, DMSO-d$_6$): δ ppm:4.39 (d, J=4.8 Hz, 2H), 5.40 (t, J=4.8 Hz, 1H), 6.95-7.08 (m, 2H), 7.21-7.32 (m, 6H), 7.41-7.47 (m, 5H), 7.64 (dd, J=7.6 Hz, J=8.4 Hz, 1H), 8.33 (t, J=2.0 Hz, 1H), 8.67 (d, J=1.6 Hz, 1H), 9.30 (d, J=1.6 Hz, 1H).

4-(5-(2H-Tetrazol-5-yl)pyridin-3-yl)-N-benzyl-3-chloro-8-phenylisoquinolin-1-amine was converted to 4-(5-(2H-tetrazol-5-yl)pyridin-3-yl)-N-benzyl-3-(methylthio)-8-phenylisoquinolin-1-amine using sodium methyl mercaptide (0.061 g, 1.2 mmol) in DMF at 100° C. for 12 h by following the procedure described for Example 15. The resulting residue was purified by silica gel column chromatography using CombiFlash (12 g REDISEP® column) with 50% ethyl acetate in hexane as an eluent to yield 4-(5-(2H-tetrazol-5-yl)pyridin-3-yl)-N-benzyl-3-(methylthio)-8-phenylisoquinolin-1-amine (0.18 g, 65%). LCMS Method B-12: retention time 2.09 min, [M+1]=502.20. $^1$H NMR (400 MHz, DMSO-d$_6$) δ ppm: 2.39 (s, 3H), 4.49 (d, J=4.8 Hz, 2H), 5.35 (t, J=5.2 Hz, 1H), 7.04-7.29 (m, 8H), 7.43-7.75 (m, 6H), 8.29 (t, J=2.0, 1 H), 8.62 (d, J=2.0 Hz, 1H), 9.29 (d, J=2.0 Hz, 1H).

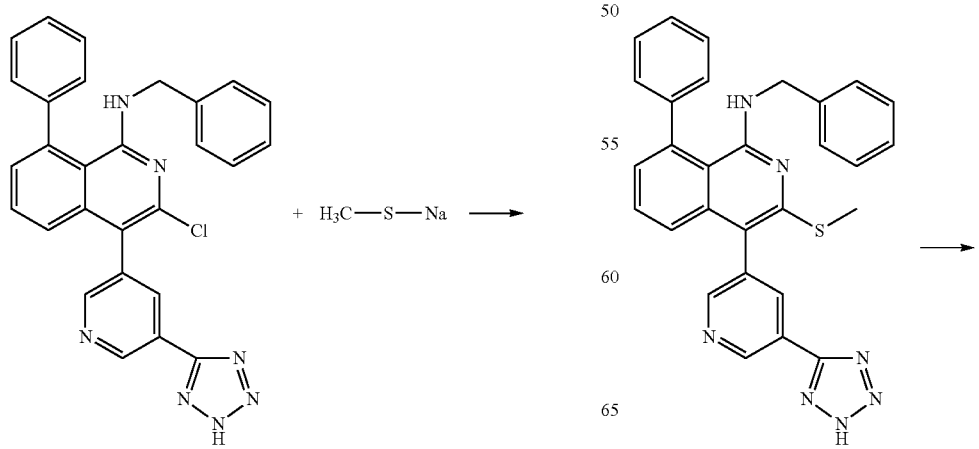

-continued

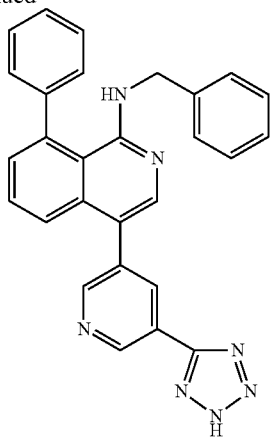

To a solution of 4-(5-(2H-tetrazol-5-yl)pyridin-3-yl)-N-benzyl-3-(methylthio)-8-phenylisoquinolin-1-amine (0.11 g, 0.19 mmol) in ethanol (15 mL) was added Raney nickel (0.50 g) and ammonium hydroxide solution (30%, 5 mL). The reaction mixture was stirred at 70° C. under hydrogen pressure (5 kg/cm$^2$) in an autoclave for 10 h by following the procedure described for Example 15. The residue was purified by preparative HPLC (Method B-61 described in general methods) to yield 4-(5-(2H-tetrazol-5-yl)pyridin-3-yl)-N-benzyl-8-phenylisoquinolin-1-amine (0.10 g, 54%). LCMS Method B-12: retention 1.83 min, [M+1]=555.8. HPLC Method B-2: retention time 6.91 min, Purity 98.90%. $^1$H NMR (400 MHz, DMSO-d$_6$): δ ppm: 4.44 (J=5.2 Hz, 2H), 5.22 (t, J=4.8 Hz, 1H), 7.00 (dd, J=1.6 Hz, J=7.6 Hz, 2H), 7.21-7.27 (m, 3H), 7.35 (dd, J=1.2 Hz, J=6.8 Hz, 1H), 7.41-7.49 (m, 5H), 7.68-7.76 (m, 3H), 8.01 (s, 1H), 8.46 (m, 1H), 8.84 (br s 1H), 9.27 (br s, 1H).

TABLE 1

| Example No. | Structure | Name | $^1$H NMR | LC/MS Rt (min) Method M + H |
|---|---|---|---|---|
| 20 | 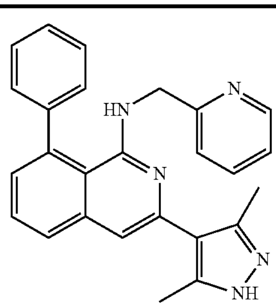 | 3-(3,5-dimethyl-1H-pyrazol-4-yl)-8-phenyl-N-(pyridin-2-ylmethyl)isoquinolin-1-amine | $^1$H NMR (400 MHz, DMSO-d$_6$) δ ppm: 2.37 (s, 6 H), 4.53 (d, J = 4.4 Hz, 2 H), 5.83 (t, J = 4.4 Hz, 1 H), 7.09 (s, 1 H), 7.12-7.20 (m, 3 H), 7.47 (s, 5 H), 7.59 (dd, J = 8.4 Hz, J = 7.2 Hz, 1 H), 7.65 (dd, J = 7.6 Hz, J = 2.0 Hz, 1 H), 7.77 (dd, J = 8.4 Hz, J = 1.2 Hz, 1 H), 8.27 (dd, J = 4.0 Hz, J = 0.8 Hz, 1 H), 12.22 (s, 1 H). | 2.03 B-13 406.2 |
| 21 | 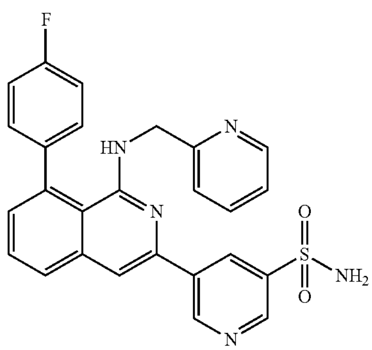 [SMILES: NS(=O)(=O)c1cncc(-c2cc3cccc(-c4ccc(F)cc4)c3c(NCc3ccccn3)n2)c1] | 5-(8-(4-fluorophenyl)-1-(pyridin-2-ylmethylamino)isoquinolin-3-yl)pyridine-3-sulfonamide | $^1$H NMR (400 MHz, DMSO-d$_6$) δ ppm: : 4.68 (d, J = 4 Hz, 2 H), 6.29 (t, J = 4 Hz, 1 H), 7.33-7.36 (m, 5 H), 7.51-7.55 (m, 2 H), 7.69-7.74 (m, 4 H), 7.91 (s, 1 H), 7.95 (dd, J = 4.4 Hz, J = 1.2 Hz, 1 H), 8.27 (d, J = 4.4 Hz, 1 H), 8.89 (t, J = 2 Hz, 1 H), 8.98 (d, J = 2.4 Hz, 1 H), 9.57 (d, J = 2 Hz, 1 H). | 1.93 B-11 486.2 |
| 22 | 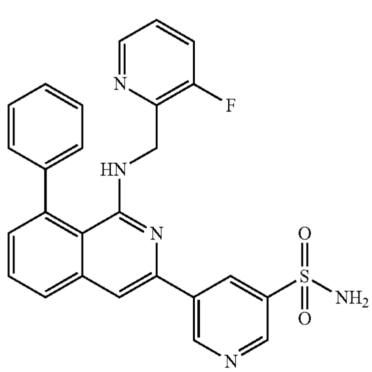 [SMILES: NS(=O)(=O)c1cncc(-c2cc3cccc(-c4ccccc4)c3c(NCc3ncccc3F)n2)c1] | 5-(1-((3-fluoropyridin-2-yl)methylamino)-8-phenylisoquinolin-3-yl)pyridine-3-sulfonamide | $^1$H NMR (400 MHz, DMSO-d$_6$) δ ppm: 4.72 (d, J = 2.4 Hz, 2 H), 6.34 (t, J = 4 Hz, 1 H), 7.30-7.38 (m, 2 H), 7.46-7.56 (m, 6 H), 7.65-7.74 (m, 3 H), 7.94-7.96 (m, 3 H), 8.09 (d, J = 4.8 Hz, 1 H), 9.00 (d, J = 2 Hz, 1 H), 9.59 (d, J = 2.0 Hz, 1 H). | 2.03 B-12 486.3 |

TABLE 1-continued

| Example No. | Structure | Name | ¹H NMR | LC/MS Rt (min) Method M + H |
|---|---|---|---|---|
| 23 | 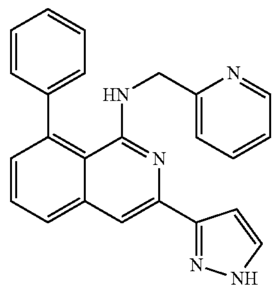 [SMILES: c1ccc(-c2cccc3cc(-c4cc[nH]n4)nc(NCc4ccccn4)c23)cc1] | 8-phenyl-3-(1H-pyrazol-3-yl)-N-(pyridin-2-ylmethyl)isoquinolin-1-amine | ¹H NMR (400 MHz, DMSO-d$_6$) δ ppm: 4.67 (d, J = 4.5 Hz, 2 H), 6.00 (t, J = 4.52 Hz, 1 H), 6.67 (s, 1 H), 7.20-7.25 (m, 3 H), 7.45-7.83 (m, 11 H), 8.28 (d, J = 4.02 Hz, 1 H). | 2.03 B-12 378.3 |
| 24 | 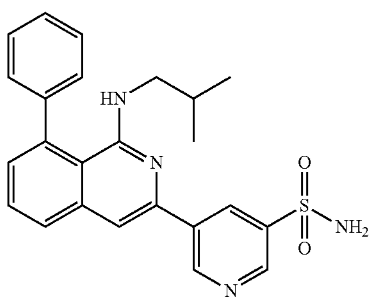 [SMILES: CC(C)CNc1nc(-c2cncc(S(N)(=O)=O)c2)cc2cccc(-c3ccccc3)c12] | 5-(1-(isobutylamino)-8-phenylisoquinolin-3-yl)pyridine-3-sulfonamide | ¹H NMR (400 MHz, DMSO-d$_6$) δ ppm: 0.67 (d, J = 6.8 Hz, 6 H), 1.51 (m, 1 H), 3.17 (dd, J = 6.0 Hz, J = 4.8 Hz, 2 H), 4.96 (t, J = 4.8 Hz, 1 H), 7.27 (dd, J = 6.8 Hz, J = 1.2 Hz, 1 H), 7.50-7.61 (m, 5 H), 7.70 (m, 3 H), 7.88 (s, 1 H), 7.91 (dd, J = 8.0 Hz, J = 0.8 Hz, 1 H), 8.87 (d, J = 2.0 Hz, 1 H), 8.97 (d, J = 2.0 Hz, 1 H), 9.54 (d, J = 2.0 Hz, 1 H). | 2.15 B-13 433.2 |
| 25 | 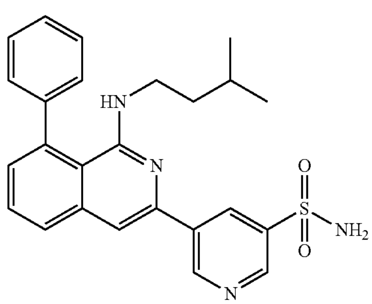 [SMILES: CC(C)CCNc1nc(-c2cncc(S(N)(=O)=O)c2)cc2cccc(-c3ccccc3)c12] | 5-(1-(isopentylamino)-8-phenylisoquinolin-3-yl)pyridine-3-sulfonamide | ¹H NMR (400 MHz, CD$_3$OD) δ ppm: 0.83 (d, J = 6.4 Hz, 6 H), 1.17 (m, 1 H), 1.29 (m, 2 H), 3.41 (m, 2 H), 4.96 (t, J = 4.8 Hz, 1 H) 7.28 (dd, J = 6.8 Hz, J = 1.2 Hz, 1 H), 7.46-7.48 (m, 4 H), 7.59 (m, 3 H), 7.65 (dd, J = 8.0 Hz, J = 7.2 Hz, 1 H), 7.70 (s, 1 H), 7.88 (dd, J = 8.4 Hz, J = 1.2 Hz, 1 H), 9.00 (dd, J = 4.0 Hz, J = 2.0 Hz, 2 H), 9.51 (d, J = 2.0 Hz, 1 H). | 2.15 B-13 447.2 |
| 26 | 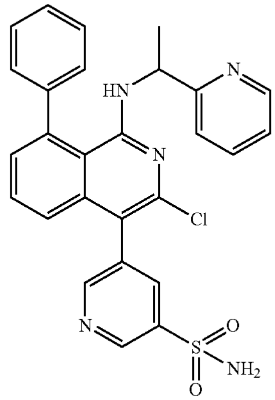 [SMILES: CC(Nc1nc(Cl)c(-c2cncc(S(N)(=O)=O)c2)c2cccc(-c3ccccc3)c12)c1ccccn1] | 5-(3-chloro-8-phenyl-1-(1-(pyridin-2-yl)ethylamino)isoquinolin-4-yl)pyridine-3-sulfonamide | ¹H NMR (400 MHz, DMSO-d$_6$) δ ppm: 1.20 (dd, J = 5.6 Hz, J = 6.4 Hz, 3 H), 5.15-5.20 (m, 1 H), 6.39 (dd, J = 6.8 Hz, J = 7.2 Hz, 1 H), 7.15-7.22 (m, 2 H), 7.29 (d, J = 7.6 Hz, 1 H), 7.33 (d, J = 7.6 Hz, 1 H), 7.49-7.72 (m, 6 H), 8.15 (t, J = 1.6 Hz, 1 H), 8.19 (t, J = 2.0 Hz, 1 H), 8.25-8.27 (m, 2 H), 8.78 (d, J = 2.0 Hz, 1 H), 8.82 (d, J = 2 Hz, 1 H), 9.07 (d, J = 2.4, 1 H). | 2.00 B-12 561.2 |

TABLE 1-continued

| Example No. | Structure | Name | ¹H NMR | LC/MS Rt (min) Method M + H |
|---|---|---|---|---|
| 27 | 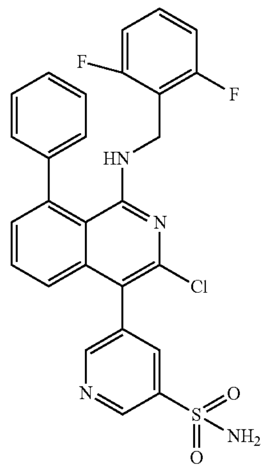 [SMILES: NS(=O)(=O)c1cncc(-c2c(Cl)nc(NCc3c(F)cccc3F)c3c(-c4ccccc4)cccc23)c1] | 5-(3-chloro-1-(2,6-difluorobenzylamino)-8-phenylisoquinolin-4-yl)pyridine-3-sulfonamide | ¹H NMR (400 MHz, DMSO-d$_6$) δ ppm: 4.44 (d, J = 4.8 Hz, 2 H), 5.16 (t, J = 4.8 Hz, 1 H), 7.02-7.06 (m, 2 H), 7.17 (dd, J = 1.2 Hz, J = 8.4 Hz, 1 H), 7.31-7.41 (m, 7 H), 7.65 (dd, J = 7.6 Hz, J = 8.4 Hz, 1 H), 7.80 (br s, 2 H), 8.18 (t, J = 2.0 Hz, 1 H), 8.80 (d, J = 2.0 Hz, 1 H), 9.08 (d, J = 2.0 Hz, 1 H). | 2.24 B-12 538.2 |
| 28 | 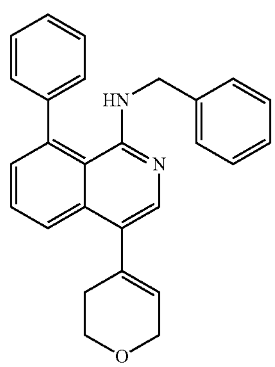 [SMILES: C1=C(c2cnc(NCc3ccccc3)c3c(-c4ccccc4)cccc23)CCOC1] | N-benzyl-4-(3,6-dihydro-2H-pyran-4-yl)-8-phenylisoquinolin-1-amine | ¹H NMR (400 MHz, DMSO-d$_6$) δ ppm: 2.39 (dd, J = 2.0 Hz, J = 4.4 Hz, 2 H), 3.91 (t, J = 5.6 Hz, 1 H), 4.28 (dd, J = 2.4 Hz, J = 5.2 H), 4.35 (d, J = 4.8 Hz, 2 H), 4.97 (t, J = 4.8 Hz, 1 H), 5.83 (t, J = 1.2 Hz, 1 H), 6.94 (dd, J = 1.6 Hz, J = 7.6 Hz, 1 H), 7.19-7.26 (m, 5 H), 7.37-7.43 (m, 6 H), 7.67 (dd, J = 7.2 Hz, J = 8.4 Hz, 1 H), 7.77 (s, 1 H), 7.82 (dd, J = 1.2 Hz, J = 8.4 Hz, 1 H). | 2.18 B-13 393.2 |
| 29 | 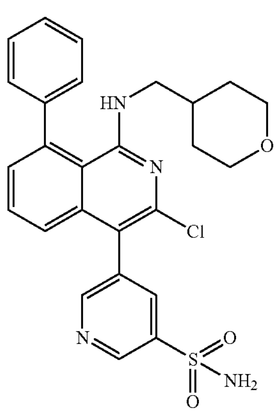 [SMILES: NS(=O)(=O)c1cncc(-c2c(Cl)nc(NCC3CCOCC3)c3c(-c4ccccc4)cccc23)c1] | 5-(3-chloro-8-phenyl-1-((tetrahydro-2H-pyran-4-yl)methylamino)isoquinolin-4-yl)pyridine-3-sulfonamide | ¹H NMR (400 MHz, DMSO-d$_6$): δ ppm: 1.02-1.05 (m, 1 H), 1.30-1.43 (m, 4 H), 1.68-1.70 (m, 1 H), 2.99-3.08 (m, 3 H), 3.37-3.43 (m, 1 H), 3.61 (dd, J = 3.2 Hz, J = 13.6 Hz, 1 H), 5.50 (d, J = 2.8 Hz, 1 H), 7.14 (dd, J = 1.2 Hz, J = 8.4 Hz, 1 H), 7.28 (dd, J = 1.2 Hz, J = 7.2 Hz, 1 H), 7.46 (br s, 2 H), 7.56-7.66 (m, 6 H), 8.16 (dd, J = 2.0 Hz, J = 4.8 Hz, 1 H), 8.79 (t, J = 2.8 Hz, 1 H), 9.07 (d, J = 2.0 Hz, 1 H). | 2.17 B-21 509.0 |

| Example No. | Structure | Name | ¹H NMR | LC/MS Rt (min) Method M + H |
|---|---|---|---|---|
| 30 | 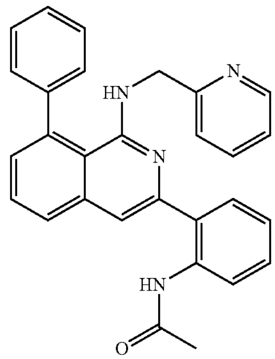 [SMILES: CC(=O)Nc1ccccc1-c1cc2cccc(-c3ccccc3)c2c(NCc2ccccn2)n1] | N-(2-(8-phenyl-1-(pyridin-2-ylmethylamino)isoquinolin-3-yl)phenyl)acetamide | ¹H NMR (400 MHz, DMSO-d₆) δ ppm: 2.07 (s, 3 H), 4.62 (d, J = 4.0 Hz, 2 H), 6.42 (t, J = 3.6 Hz, 1 H) 7.18-7.29 (m, 4 H), 7.29-7.40 (m, 1 H), 7.49-7.52 (m, 6 H), 7.67-7.73 (m, 3 H), 7.91-7.93 (m, 1 H), 8.23-8.32 (m, 2 H), 11.20 (s, 1 H) | 2.20 B-12 445.2 |
| 31 | 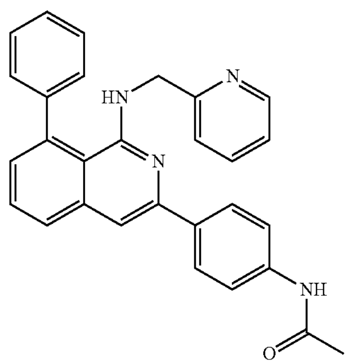 [SMILES: CC(=O)Nc1ccc(-c2cc3cccc(-c4ccccc4)c3c(NCc3ccccn3)n2)cc1] | N-(4-(8-phenyl-1-(pyridin-2-ylmethylamino)isoquinolin-3-yl)phenyl)acetamide | ¹H NMR (400 MHz, DMSO-d₆) δ ppm: 2.08 (s, 3 H), 4.63 (d, J = 4.4 Hz, 2 H), 5.98 (t, J = 4.4 Hz, 1 H) 7.19-7.24 (m, 3 H), 7.46-7.52 (m, 5 H), 7.61-7.70 (m, 5 H), 7.83-7.86 (m, 1 H), 8.08-8.28 (m, 2 H), 8.29-8.30 (m, 1 H), 10.01 (s, 1 H) | 2.06 B-12 445.3 |
| 32 | 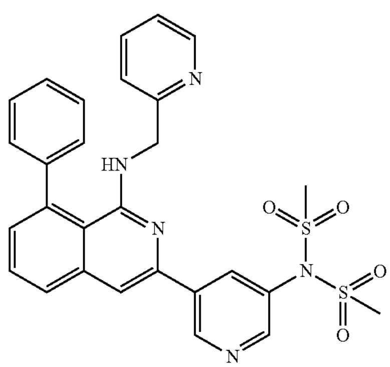 [SMILES: CS(=O)(=O)N(c1cncc(-c2cc3cccc(-c4ccccc4)c3c(NCc3ccccn3)n2)c1)S(C)(=O)=O] | N-(methylsulfonyl)-N-(5-(8-phenyl-1-(pyridin-2-ylmethylamino)isoquinolin-3-yl)pyridin-3-yl)methanesulfonamide | ¹H NMR (400 MHz, DMSO-d₆) δ ppm: 3.67 (s, 6 H), 4.63 (d, J = 4.4 Hz, 2 H), 6.12 (t, J = 4.8 Hz, 1 H), 7.18-7.30 (m, 2 H), 7.31-7.32 (m, 1 H), 7.50-7.55 (m, 5 H), 7.66-7.74 (m, 2 H), 7.89-7.91 (m, 1 H), 7.94 (s, 1 H), 8.23-8.32 (m, 1 H), 8.54 (t, J = 2.4 Hz, 1 H), 8.74 (d, J = 2 Hz, 1 H), 9.45 (d, J = 2 Hz, 1 H) | 2.06 B-11 560.2 |
| 33 | 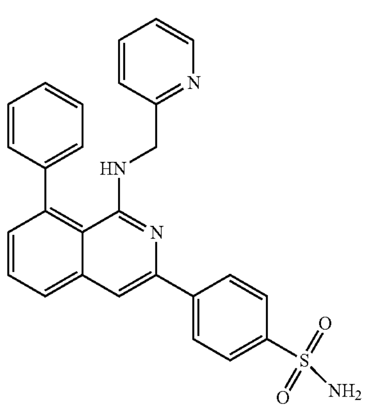 [SMILES: NS(=O)(=O)c1ccc(-c2cc3cccc(-c4ccccc4)c3c(NCc3ccccn3)n2)cc1] | 4-(8-phenyl-1-(pyridin-2-ylmethylamino)isoquinolin-3-yl)benzenesulfonamide | ¹H NMR (400 MHz, DMSO-d₆) δ ppm: 4.64 (d, J = 4.4 Hz, 2 H), 6.08 (t, J = 4.4 Hz, 1 H), 7.19-7.29 (m, 3 H), 7.38 (br s, 2 H), 7.48-7.53 (m, 5 H), 7.66-7.71 (m, 2 H), 7.83 (s, 1 H), 7.89-7.92 (m, 3 H), 8.29-8.34 (m, 3 H). | 2.06 B-11 467.2 |

| Example No. | Structure | Name | $^1$H NMR | LC/MS Rt (min) Method M + H |
|---|---|---|---|---|
| 34 | 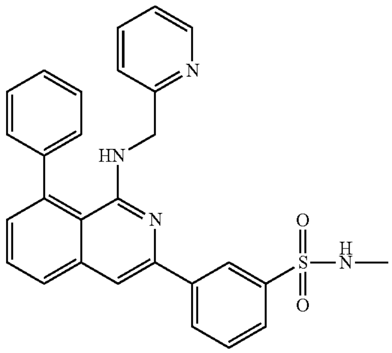 [SMILES: CNS(=O)(=O)c1cccc(-c2cc3cccc(-c4ccccc4)c3c(NCc3ccccn3)n2)c1] | N-methyl-3-(8-phenyl-1-(pyridin-2-ylmethylamino)isoquinolin-3-yl)benzenesulfonamide | $^1$H NMR (400 MHz, DMSO-d$_6$) δ ppm: 2.47-2.52 (m, 3 H), 4.64 (d, J = 4.4 Hz, 2 H), 6.07 (t, J = 4.4 Hz, 1 H), 7.19-7.24 (m, 2 H), 7.28 (dd, J = 1.2 Hz, J = 6.8 Hz, 1 H), 7.48-7.53 (m, 7 H), 7.66-7.73 (m, 3 H), 7.77 (dd, J = 1.2 Hz, J = 1.6 Hz, 1 H), 7.80 (br s, 1 H), 7.94 (dd, J = 1.2 Hz, J = 8.0 Hz, 1 H), 8.29 (dd, J = 1.2 Hz, J = 1.6 Hz, J = 4.8 Hz, 1 H), 8.55 (dd, J = 1.6 Hz, J = 1.2 Hz, 1 H). | 2.22 B-11 481.2 |
| 35 | 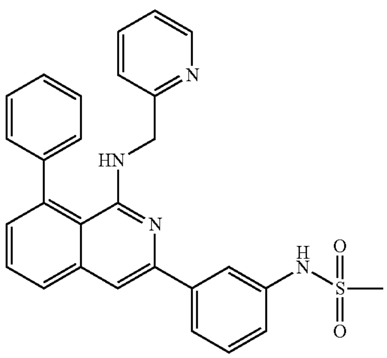 [SMILES: CS(=O)(=O)Nc1cccc(-c2cc3cccc(-c4ccccc4)c3c(NCc3ccccn3)n2)c1] | N-(3-(8-phenyl-1-(pyridin-2-ylmethylamino)isoquinolin-3-yl)phenyl)methanesulfonamide | $^1$H NMR (400 MHz, DMSO-d$_6$) δ ppm: 3.31 (s, 3 H), 4.64 (d, J = 4.4 Hz, 2 H), 6.07 (t, J = 4.4 Hz, 1 H), 7.19-7.24 (m, 4 H), 7.41-7.50 (m, 6 H), 7.64-7.70 (m, 3 H), 7.87-7.90 (m, 2 H), 8.11-8.28 (m, 1 H), 8.28-8.29 (m, 1 H), 9.84 (br s, 1 H) | 2.10 B-12 481.3 |
| 36 | 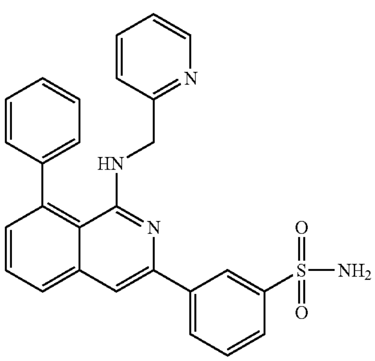 [SMILES: NS(=O)(=O)c1cccc(-c2cc3cccc(-c4ccccc4)c3c(NCc3ccccn3)n2)c1] | 3-(8-phenyl-1-(pyridin-2-ylmethylamino)isoquinolin-3-yl)benzenesulfonamide | $^1$H NMR (400 MHz, DMSO-d$_6$) δ ppm: 4.66 (d, J = 4.0 Hz, 2 H), 6.10 (dd, J = 4.4 Hz, J = 4.0 Hz, 1 H), 7.19-7.24 (m, 2 H), 7.27 (dd, J = 6.8 Hz, J = 0.8 Hz, 1 H), 7.44 (s, 2 H), 7.47-7.52 (m, 5 H), 7.66-7.71 (m, 3 H), 7.77 (s, 1 H), 7.84 (d, J = 8.0 Hz, 1 H), 7.91 (dd, J = 8.0 Hz, J = 0.8 Hz, 1 H), 8.29 (d, J = 4.4 Hz, 1 H), 8.39 (d, J = 7.6 Hz, 1 H), 8.65 (t, J = 1.2 Hz, 1 H). | 2.09 B-13 467.2 |
| 37 | 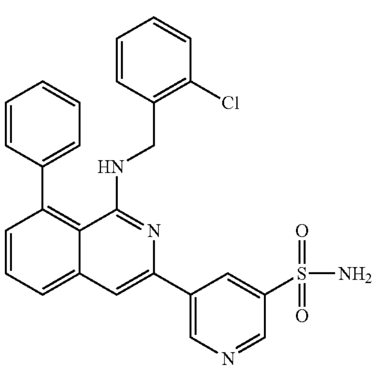 [SMILES: NS(=O)(=O)c1cncc(-c2cc3cccc(-c4ccccc4)c3c(NCc3ccccc3Cl)n2)c1] | 5-(1-(2-chlorobenzylamino)-8-phenylisoquinolin-3-yl)pyridine-3-sulfonamide | $^1$H NMR (400 MHz, DMSO-d$_6$) δ ppm: 4.59 (d, J = 5.6 Hz, 2 H), 5.24 (t, J = 5.2 Hz, 1 H), 7.21-7.31 (m, 4 H), 7.37-7.47 (m, 6 H), 7.68-7.73 (m, 3 H), 7.92-7.95 (m, 2 H), 8.88 (t, J = 2 Hz, 1 H), 8.97 (d, J = 2 Hz, 1 H), 9.54 (d, J = 2 Hz, 1 H). | 2.21 B-11 499.1 |

| Example No. | Structure | Name | $^1$H NMR | LC/MS Rt (min) Method M + H |
|---|---|---|---|---|
| 38 | 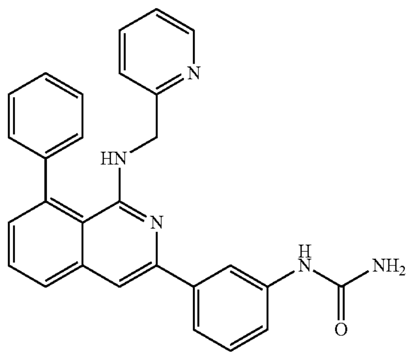 [SMILES: NC(=O)Nc1cccc(-c2cc3cccc(-c4ccccc4)c3c(NCc3ccccn3)n2)c1] | 1-(3-(8-phenyl-1-(pyridin-2-ylmethylamino)isoquinolin-3-yl)phenyl)urea | $^1$H NMR (400 MHz, DMSO-d$_6$) δ ppm: 4.64 (d, J = 4.0 Hz, 2 H), 5.91 (s, 2 H), 5.99 (t, J = 4.0 Hz, 1 H), 7.20-7.29 (m, 3 H), 7.31-7.32 (m, 1 H), 7.46-7.52 (m, 6 H), 7.58 (s, 1 H), 7.62-7.70 (m, 3 H), 7.87-7.89 (m, 1 H), 8.14-8.15 (m, 1 H), 8.27-8.29 (m, 1 H), 8.72 (s, 1 H) | 1.97 B-11 466.2 |
| 39 | 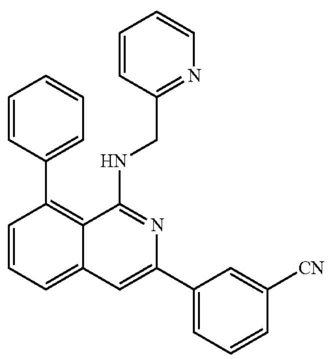 [SMILES: N#Cc1cccc(-c2cc3cccc(-c4ccccc4)c3c(NCc3ccccn3)n2)c1] | 3-(8-phenyl-1-(pyridin-2-ylmethylamino)isoquinolin-3-yl)benzonitrile | $^1$H NMR (400 MHz, DMSO-d$_6$) δ ppm: 4.63 (d, J = 4.4 Hz, 2 H), 6.10 (t, J = 4.2 Hz, 1 H), 7.19-7.30 (m, 3 H), 7.48-7.54 (m, 5 H), 7.66-7.68 (m, 3 H), 7.70-7.88 (m, 3 H), 8.24-8.29 (m, 1 H), 8.48-8.54 (m, 2 H). | 2.26 B-12 413.2 |
| 40 | 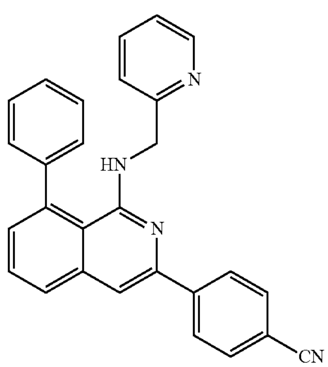 [SMILES: N#Cc1ccc(-c2cc3cccc(-c4ccccc4)c3c(NCc3ccccn3)n2)cc1] | 4-(8-phenyl-1-(pyridin-2-ylmethylamino)isoquinolin-3-yl)benzonitrile | $^1$H NMR (400 MHz, DMSO-d$_6$) δ ppm: 4.64 (d, J = 4.4 Hz, 2 H), 6.16 (t, J = 4.3 Hz, 1 H), 7.19-7.30 (m, 3 H), 7.48-7.54 (m, 5 H), 7.69-7.69 (m, 4 H), 7.72-7.89 (m, 2 H), 8.25-8.29 (m, 1 H), 8.49-8.57 (m, 2 H). | 2.36 B-12 413.2 |
| 41 | 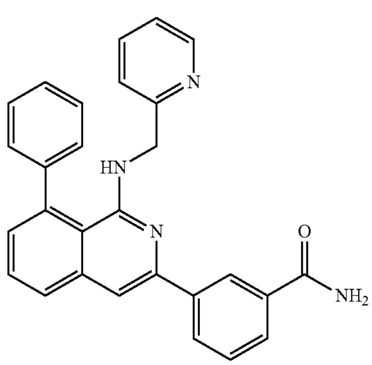 [SMILES: NC(=O)c1cccc(-c2cc3cccc(-c4ccccc4)c3c(NCc3ccccn3)n2)c1] | 3-(8-phenyl-1-(pyridin-2-ylmethylamino)isoquinolin-3-yl)benzamide | $^1$H NMR (400 MHz, DMSO-d$_6$) δ ppm: 4.66 (d, J = 4.0 Hz, 2 H), 6.06 (t, J = 4.4 Hz, 1 H), 7.19-7.26 (m, 3 H), 7.27-7.68 (m, 7 H), 7.68-7.69 (m, 2 H), 7.70 (s, 1 H), 7.87-7.93 (m, 2 H), 8.05 (m, 1 H), 8.25-8.35 (m, 2 H), 8.65 (s, 1 H). | 2.03 B-12 431.2 |

TABLE 1-continued

| Example No. | Structure | Name | ¹H NMR | LC/MS Rt (min) Method M + H |
|---|---|---|---|---|
| 42 | 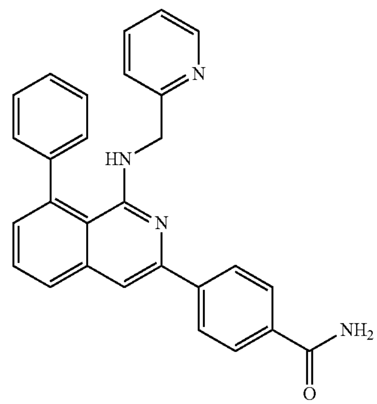 [SMILES: NC(=O)c1ccc(-c2cc3cccc(-c4ccccc4)c3c(NCc3ccccn3)n2)cc1] | 4-(8-phenyl-1-(pyridin-2-ylmethylamino)isoquinolin-3-yl)benzamide | ¹H NMR (400 MHz, DMSO-d$_6$) δ ppm: 4.62 (d, J = 4.4 Hz, 2 H), 6.16 (t, J = 4.4 Hz, 1 H), 7.19-7.28 (m, 3 H), 7.27-7.69 (m, 7 H), 7.68-7.72 (m, 3 H), 7.87-7.93 (m, 2 H), 8.05 (m, 1 H), 8.25-8.35 (m, 2 H), 8.65 (s, 1 H). | 2.06 B-12 431.2 |
| 43 | 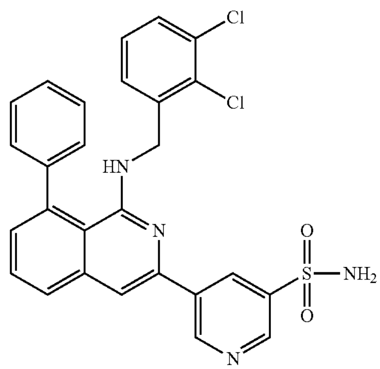 [SMILES: NS(=O)(=O)c1cncc(-c2cc3cccc(-c4ccccc4)c3c(NCc3cccc(Cl)c3Cl)n2)c1] | 5-(1-(2,3-dichlorobenzylamino)-8-phenylisoquinolin-3-yl)pyridine-3-sulfonamide | ¹H NMR (400 MHz, DMSO-d$_6$) δ ppm: 4.62 (d, J = 5.6 Hz, 2 H), 5.26 (t, J = 5.6 Hz, 1 H), 7.25-7.28 (m, 2 H), 7.31-7.33 (m, 1 H), 7.40-7.48 (m, 5 H), 7.52-7.53 (m, 1 H), 7.54-7.74 (m, 3 H), 7.93-7.96 (m, 2 H), 8.88 (t, J = 2 Hz, 1 H), 8.99 (d, J = 2 Hz, 1 H), 9.54 (d, J = 2 Hz, 1 H). | 2.29 B-12 536.3 |
| 44 | 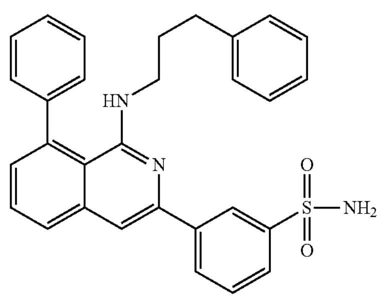 [SMILES: NS(=O)(=O)c1cccc(-c2cc3cccc(-c4ccccc4)c3c(NCCCc3ccccc3)n2)c1] | 3-(8-phenyl-1-(3-phenylpropylamino)isoquinolin-3-yl)benzenesulfonamide | ¹H NMR (400 MHz, MeOH-d$_4$) δ ppm: 1.63 (m, 2 H), 2.42 (t, J = 8.0 Hz, 2 H), 3.42 (t, J = 6.4 Hz, 2 H), 7.10 (d, J = 7.2 Hz, 2 H), 7.15-7.25 (m, 5 H), 7.32 (dd, J = 2.0, J = 7.2 Hz, 1 H), 7.52 (dd, J = 1.6, J = 7.6 Hz, 2 H), 7.59-7.68 (m, 6 H), 7.73 (s, 1 H), 7.90 (dd, J = 1.2, J = 8.4 Hz, 1 H), 9.01 (m, 2 H), 9.50 (d, J = 1.6 Hz, 1 H). | 2.0 B-9 495.4 |
| 45 | 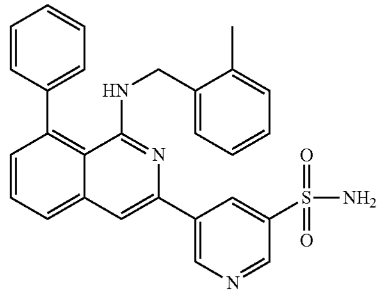 [SMILES: Cc1ccccc1CNc1nc(-c2cncc(S(N)(=O)=O)c2)cc2cccc(-c3ccccc3)c12] | 5-(1-(2-methylbenzylamino)-8-phenylisoquinolin-3-yl)pyridine-3-sulfonamide | ¹H NMR (400 MHz, DMSO-d$_6$) δ ppm: 2.13 (s, 3 H), 4.51 (d, J = 4.0 Hz, 2 H), 5.00 (t, J = 4.8 Hz, 1 H), 6.95 (d, J = 4.8 Hz, 1 H), 7.05-7.15 (m, 3 H), 7.28-7.44 (m, 6 H), 7.69-7.79 (m, 3 H), 7.93-7.95 (m, 2 H), 8.88 (t, J = 2 Hz, 1 H), 8.97 (d, J = 2 Hz, 1 H), 9.54 (d, J = 2 Hz, 1 H). | 1.95 B-12 481.5 |

TABLE 1-continued

| Example No. | Name | ¹H NMR | LC/MS Rt (min) Method M + H |
|---|---|---|---|
| 46 | N-(5-(3-chloro-8-phenyl-1-(pyridin-2-ylmethylamino)isoquinolin-4-yl)pyridin-3-yl)acetamide | ¹H NMR (400 MHz, DMSO-d₆) δ ppm: 2.12 (s, 3 H), 4.54 (d, J = 4.0 Hz, 2 H), 6.57 (t, J = 4.0 Hz, 1 H), 7.21-7.31 (m, 4 H), 7.50-7.54 (m, 5 H), 7.62-7.73 (m, 2 H), 8.08 (t, J = 2.0 Hz 1 H) 8.21- 8.22 (m, 2 H), 8.82 (s, 1 H), 10.30 (s, 1 H) | 1.94 B-12 480.3 |
| 47 | N-(5-(3-chloro-8-phenyl-1-(pyridin-2-ylmethylamino)isoquinolin-4-yl)pyridin-3-yl)methanesulfonamide | ¹H NMR (400 MHz, CD₃OD) δ ppm: 3.11 (s, 3 H), 4.57 (d, J = 4.4 Hz, 2 H), 6.03 (t, J = 4.4 Hz. 1 H), 7.22-7.32 (m, 4 H), 7.44-7.48 (m, 4 H), 7.59 (dd, J = 8.4 Hz, J = 7.2 Hz, 1 H), 7.70-7.75 (m, 4 H), 8.30 (br s, 1 H), 8.32 (d, J = 4.8 Hz, 1 H), 8.55 (br s, 1 H). | 1.98 B-12 516.3 |
| 48 | 1-(5-(3-chloro-8-phenyl-1-(pyridin-2-ylmethylamino)isoquinolin-4-yl)pyridin-3-yl)urea | ¹H NMR (400 MHz, DMSO-d₆) δ ppm: 4.53 (d, J = 4.4 Hz, 2 H), 6.18 (s, 2 H), 6.54 (t, J = 4.0 Hz, 1 H), 7.20-7.30 (m, 4 H), 7.49-7.51 (m, 5 H), 7.52-7.72 (m, 2 H), 7.79 (s, 1 H) 8.12 (s, 1 H), 8.20-8.25 (m, 1 H), 8.65 (s, 1 H), 9.23 (s, 1 H) | 1.84 B-12 481.1 |
| 49 | 3-(2-aminophenyl)-8-phenyl-N-(pyridin-2-ylmethyl)isoquinolin-1-amine | ¹H NMR (400 MHz, DMSO-d₆) δ ppm: 4.51 (d, J = 4.4 Hz, 2 H), 6.05-6.10 (m, 3 H), 6.61-6.65 (m, 1 H), 6.73 (dd, J = 1.2 Hz, J = 8.0 Hz 1 H), 7.04-7.07 (m, 1 H), 7.17 (d, J = 8.0 Hz, 1 H), 7.20-7.23 (m, 2 H), 7.38 (s, 1 H), 7.50-7.52 (m, 6 H), 7.62-7.70 (m, 2 H), 7.84 (dd, J = 1.2 Hz, J = 8.4 Hz, 1 H), 8.27-8.29 (m, 1 H). | 1.68 B-9 403.2 |

TABLE 1-continued

| Example No. | Structure | Name | ¹H NMR | LC/MS Rt (min) Method M + H |
|---|---|---|---|---|
| 50 | 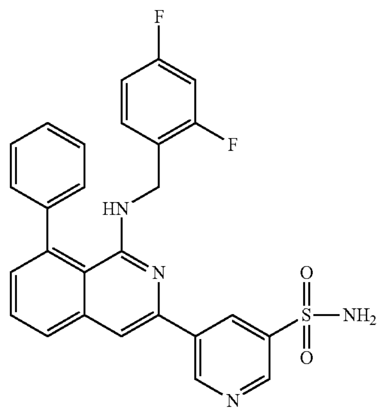 [SMILES: NS(=O)(=O)c1cncc(-c2cc3cccc(-c4ccccc4)c3c(NCc3ccc(F)cc3F)n2)c1] | 5-(1-(2,4-difluorobenzylamino)-8-phenylisoquinolin-3-yl)pyridine-3-sulfonamide | ¹H NMR (400 MHz, DMSO-$d_6$) δ ppm: 4.52 (d, J = 4.8 Hz, 2 H), 5.11 (t, J = 4.8 Hz, 1 H), 6.92-7.00 (m, 1 H), 7.16-7.25 (m, 2 H), 7.32 (dd, J = 1.2, J = 7.2 Hz, 1 H), 7.41-7.46 (m, 5 H), 7.62 (br s, 2 H), 7.72 (dd, J = 7.2, J = 8.0 Hz, 2 H), 7.93-7.95 (m, 2 H), 8.88 (t, J = 2.4 Hz, 1 H), 8.97 (d, J = 2.0 Hz, 1 H), 9.51 (d, J = 2.0 Hz, 1 H). | 1.95 B-9 503.1 |
| 51 | 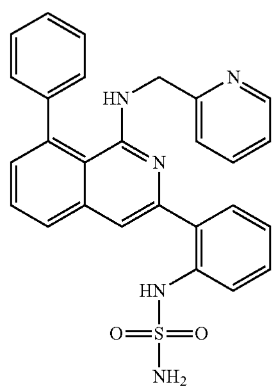 [SMILES: NS(=O)(=O)Nc1ccccc1-c1cc2cccc(-c3ccccc3)c2c(NCc2ccccn2)n1] | 3-(2-aminophenyl)-8-phenyl-N-(pyridin-2-ylmethyl)isoquinolin-1-sulfonyl urea | ¹H NMR (400 MHz, DMSO-$d_6$) δ ppm: 4.65 (d, J = 3.6 Hz, 2 H), 6.66 (t, J = 3.6 Hz, 1 H), 7.12-7.16 (m, 1 H), 7.17-7.28 (m, 5 H), 7.37-7.56 (m, 6 H), 7.64 (dd, J = 1.2, J = 8.4 Hz, 1 H), 7.68-7.74 (m, 3 H), 7.92 (dd, J = 1.2, J = 8.0 Hz, 1 H), 7.97 (dd, J = 1.2, J = 7.6 Hz, 1 H), 8.16 (d, J = 4.4 Hz, 1 H), 12.70 (s, 1 H). | 1.66 B-9 482.6 |
| 52 | 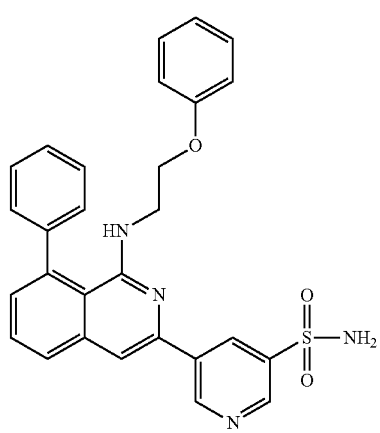 [SMILES: NS(=O)(=O)c1cncc(-c2cc3cccc(-c4ccccc4)c3c(NCCOc3ccccc3)n2)c1] | 5-(1-(2-phenoxyethylamino)-8-phenylisoquinolin-3-yl)pyridine-3-sulfonamide | ¹H NMR (400 MHz, DMSO-$d_6$) δ ppm: 3.76 (t, J = 5.2 Hz, 2 H), 3.90 (t, J = 4.8 Hz, 2 H), 5.21 (t, J = 4.8 Hz, 1 H), 6.81-6.83 (m, 2 H), 6.95 (t, J = 7.6 Hz, 1 H) 7.27-7.46 (m, 8 H), 7.69-7.73 (m, 3 H), 7.91-7.94 (m, 2 H), 8.88 (t, J = 2 Hz, 1 H), 8.97 (d, J = 2 Hz, 1 H), 9.54 (d, J = 2 Hz, 1 H). | 2.18 B-13 497.2 |

TABLE 1-continued

| Example No. | Structure | Name | ¹H NMR | LC/MS Rt (min) Method M + H |
|---|---|---|---|---|
| 53 | 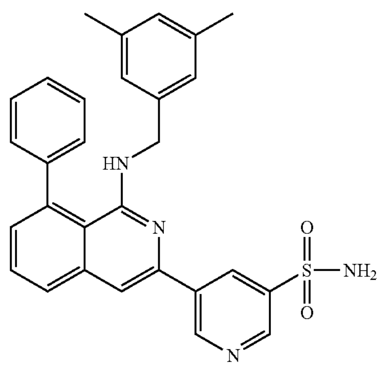 [SMILES: Cc1cc(C)cc(CNc2nc(-c3cncc(S(N)(=O)=O)c3)cc3cccc(-c4ccccc4)c23)c1] | 5-(1-(3,5-dimethylbenzylamino)-8-phenylisoquinolin-3-yl)pyridine-3-sulfonamide | ¹H NMR (400 MHz, DMSO-d$_6$) δ ppm: 2.08 (s, 6 H), 4.45 (d, J = 4.0 Hz, 2 H), 5.20 (t, J = 4.8 Hz, 1 H), 6.63 (s, 2 H), 6.84 (s, 1 H), 7.29 (d, J = 1.2 Hz, 1 H), 7.30-750 (m, 5 H), 7.68-7.73 (m, 3 H), 7.93-7.95 (m, 2 H), 8.88 (t, J = 2 Hz, 1 H), 8.97 (d, J = 2 Hz, 1 H), 9.54 (d, J = 2 Hz, 1 H). | 2.20 B-13 495.2 |
| 54 | 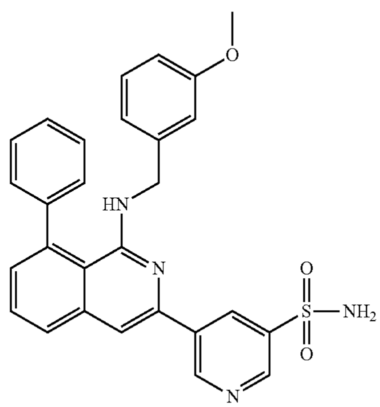 [SMILES: COc1cccc(CNc2nc(-c3cncc(S(N)(=O)=O)c3)cc3cccc(-c4ccccc4)c23)c1] | 5-(1-(3-methoxybenzylamino)-8-phenylisoquinolin-3-yl)pyridine-3-sulfonamide | ¹H NMR (400 MHz, DMSO-d$_6$) δ ppm: 3.72 (s, 3 H), 4.48 (d, J = 4.8 Hz, 2 H), 5.23 (t, J = 4.8 Hz, 1 H), 6.62-6.76 (m, 2 H), 6.78 (dd, J = 2.4 Hz, J = 6.4 Hz 1 H), 7.17 (t, J = 8.0 Hz, 1 H), 7.29-7.31 (m, 1 H), 7.40-7.47 (m, 5 H), 7.67-7.73 (m, 3 H), 7.92-7.95 (m, 2 H), 8.88 (t, J = 2 Hz, 1 H), 8.97 (d, J = 2 Hz, 1 H), 9.54 (d, J = 2 Hz, 1 H). | 2.07 B-13 497.2 |
| 55 | 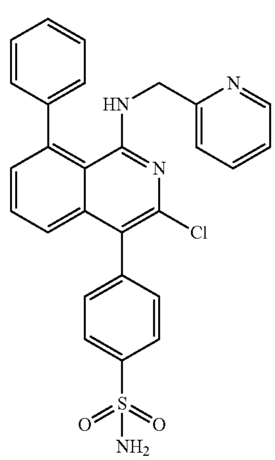 [SMILES: NS(=O)(=O)c1ccc(-c2c(Cl)nc(NCc3ccccn3)c3c(-c4ccccc4)cccc23)cc1] | 4-(3-chloro-8-phenyl-1-(pyridin-2-ylmethylamino)isoquinolin-4-yl)benzenesulfonamide | ¹H NMR (400 MHz, DMSO-d$_6$) δ ppm: 4.54 (d, J = 3.6, 2 H), 6.55 (dd, J = 4.4 Hz, J = 4.0 Hz, 1 H), 7.17 (dd, J = 8.4 Hz, J = 1.2 Hz, 1 H), 7.23 (dd, J = 7.2 Hz, J = 5.6 Hz, 1 H), 7.27-7.30 (m, 2 H), 7.48-7.65 (m, 11 H), 7.98-8.01 (m, 2 H), 8.22 (d, J = 4.4 Hz, 1 H). | 2.04 B-13 501.2 |

TABLE 1-continued

| Example No. | Structure | Name | ¹H NMR | LC/MS Rt (min) Method M + H |
|---|---|---|---|---|
| 56 | 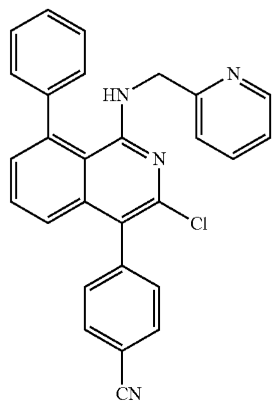 [SMILES: N#Cc1ccc(-c2c(Cl)nc(NCc3ccccn3)c3c(-c4ccccc4)cccc23)cc1] | 4-(3-chloro-8-phenyl-1-(pyridin-2-ylmethylamino)isoquinolin-4-yl)benzonitrile | ¹H NMR (400 MHz, DMSO-d$_6$) δ ppm: 4.54 (d, J = 4.0 Hz, 2 H), 6.58 (t, J = 4.0 Hz, 1 H), 7.17 (dd, J = 8.4 Hz, J = 1.2 Hz, 1 H), 7.23 (dd, J = 7.2 Hz, J = 5.6 Hz, 1 H), 7.27-7.31 (m, 2 H), 7.47-7.64 (m, 8 H), 7.71 (dt, J = 7.6 Hz, J = 1.6 Hz, 1 H), 8.02-8.04 (m, 2 H), 8.21 (dd, J = 4.4 Hz, J = 0.8 Hz, 1 H). | 2.21 B-13 447.1 |
| 57 | 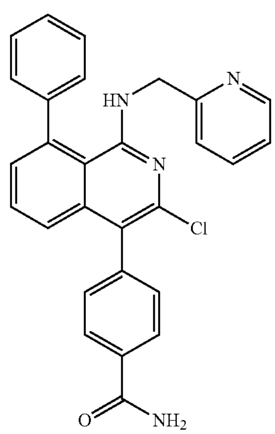 [SMILES: NC(=O)c1ccc(-c2c(Cl)nc(NCc3ccccn3)c3c(-c4ccccc4)cccc23)cc1] | 4-(3-chloro-8-phenyl-1-(pyridin-2-ylmethylamino)isoquinolin-4-yl)benzamide | ¹H NMR (400 MHz, DMSO-d$_6$) δ ppm: 4.53 (d, J = 4.0 Hz, 2 H), 6.51 (t, J = 4.0 Hz, 1 H), 7.20-7.29 (m, 4 H), 7.44-7.54 (m, 8 H), 7.61 (dd, J = 8.4 Hz, J = 3.2 Hz, 1 H), 7.70 (dt, J = 7.6 Hz, J = 1.4 Hz, 1 H), 8.03 (dd, J = 6.4 Hz, J = 1.6 Hz, 2 H), 8.08 (br s, 1 H), 8.21-8.23 (m, 1 H). | 2.02 B-13 464.2 |
| 58 | 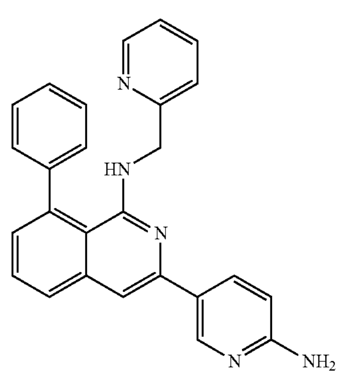 [SMILES: Nc1ccc(-c2cc3cccc(-c4ccccc4)c3c(NCc3ccccn3)n2)cn1] | 3-(6-aminopyridin-3-yl)-8-phenyl-N-(pyridin-2-ylmethyl)isoquinolin-1-amine | ¹H NMR (400 MHz, DMSO-d$_6$) δ ppm: 4.59 (d, J = 4.4 Hz, 2 H), 5.93 (t, J = 4.4 Hz, 1 H), 6.12 (s, 2 H), 6.50 (dd, J = 0.4, J = 9.2 Hz, 1 H), 7.14 (dd, J = 1.2, J = 7.2, 1 H), 7.18-7.22 (m, 2 H), 7.46-7.51 (m, 6 H), 7.59 (dd, J = 6.8, J = 8.0 Hz, 1 H), 7.67 (dt, J = 1.6, J = 7.6 Hz, 1 H), 7.77 (dd, J = 1.2, J = 8.0 Hz, 1 H), 8.11 (dd, J = 2.4, J = 8.8 Hz, 1 H), 8.28 (m, 1 H), 8.72 (d, J = 2.0 Hz, 1 H). | 1.76 B-12 404.2 |

TABLE 1-continued

| Example No. | Name | ¹H NMR | LC/MS Rt (min) Method M + H |
|---|---|---|---|
| 59 | 5-(1-(4-(dimethylamino)benzylamino)-8-phenylisoquinolin-3-yl)pyridine-3-sulfonamide | ¹H NMR (400 MHz, DMSO-d₆) δ ppm: 2.52 (s, 6 H), 4.38 (d, J = 5.2 Hz, 2 H), 5.14 (t, J = 5.2 Hz, 1 H), 6.59 (dd, J = 2.8, J = 11.6 Hz, 2 H), 6.88 (d, J = 8.8 Hz, 2 H), 7.29 (dd, J = 1.2, J = 6.8 Hz, 1 H), 7.42-7.51 (m, 5 H), 7.68-7.72 (m, 3 H), 7.91 (d, J = 1.6 Hz, 1 H), 7.93 (d, J = 1.2 Hz, 1 H), 8.92 (t, J = 2.0 Hz, 1 H), 8.98 (d, J = 2.0 Hz, 1 H), 9.55 (d, J = 1.6 Hz, 1 H). | 1.99 B-47 510.2 |
| 60 | N-(3-(3-chloro-8-phenyl-1-(pyridin-2-ylmethylamino)isoquinolin-4-yl)phenyl)acetamide | ¹H NMR (400 MHz, DMSO-d₆) δ ppm: 2.07 (s, 3 H), 4.52 (d, J = 4.4 Hz, 2 H), 6.45 (t, J = 4.4 Hz, 1 H), 7.00-7.01 (m, 1 H), 7.20-7.28 (m, 4 H), 7.44-7.71 (m, 10 H), 8.21-8.23 (m, 1 H), 10.01 (s, 1 H) | 2.39 B-17 479.2 |
| 61 | 3-(3-chloro-8-phenyl-1-(pyridin-2-ylmethylamino)isoquinolin-4-yl)benzonitrile | ¹H NMR (400 MHz, DMSO-d₆) δ ppm: 4.55 (d, J = 4.0 Hz, 2 H), 6.50 (t, J = 4.4 Hz, 1 H), 7.18 (d, J = 1.2 Hz, 1 H), 7.24-7.33 (m, 3 H), 7.47-7.54 (m, 4 H), 7.61-7.65 (m, 1 H), 7.71-7.80 (m, 4 H), 7.95 (s, 1 H), 7.96-7.98 (m, 1 H), 8.26 (d, J = 4.4 Hz, 1 H) | 2.24 B-13 447.0 |

TABLE 1-continued

| Example No. | Structure | Name | ¹H NMR | LC/MS Rt (min) Method M + H |
|---|---|---|---|---|
| 62 | 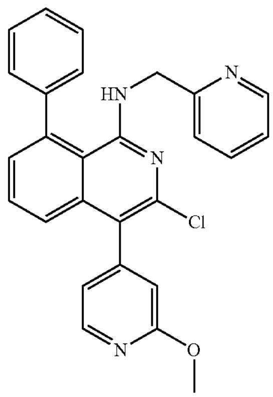 [SMILES: COc1cc(-c2c(Cl)nc(NCc3ccccn3)c3c(-c4ccccc4)cccc23)ccn1] | 3-chloro-4-(2-methoxypyridin-4-yl)-8-phenyl-N-(pyridin-2-ylmethyl)isoquinolin-1-amine | ¹H NMR (400 MHz, DMSO-d₆) δ ppm: 3.95 (s, 3 H), 4.52 (d, J = 4.0 Hz, 2 H), 6.51 (t, J = 4.0 Hz, 1 H), 6.99 (m, 1 H), 7.20-7.29 (m, 4 H), 7.47-7.53 (m, 5 H), 7.61-7.73 (m, 3 H), 8.15 (dd, J = 2.4 Hz, J = 2.4 Hz, 1 H), 8.20-8.22 (m, 1 H) | 2.65 B-17 453.2 |
| 63 | 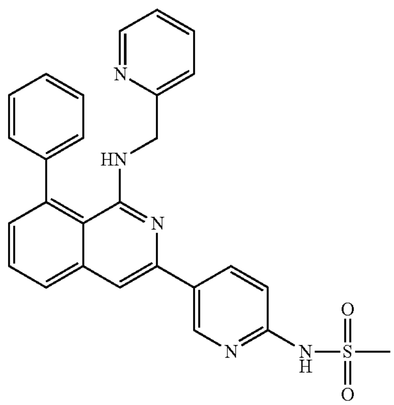 [SMILES: CS(=O)(=O)Nc1ccc(-c2cc3cccc(-c4ccccc4)c3c(NCc3ccccn3)n2)cn1] | N-(5-(8-phenyl-1-(pyridin-2-ylmethylamino)isoquinolin-3-yl)pyridin-2-yl)methanesulfonamide | ¹H NMR (400 MHz, MeOH-d₄) δ ppm: 3.23 (s, 3 H), 4.63 (s, 2 H), 7.21-7.29 (m, 4 H), 7.46-7.51 (m, 6 H), 7.57 (s, 1 H), 7.62-7.71 (m, 4 H), 7.85 (d, J = 6.8 Hz, 1 H), 8.40 (d, J = 6.4 Hz, 2 H). | 1.94 B-47 482.2 |
| 64 | 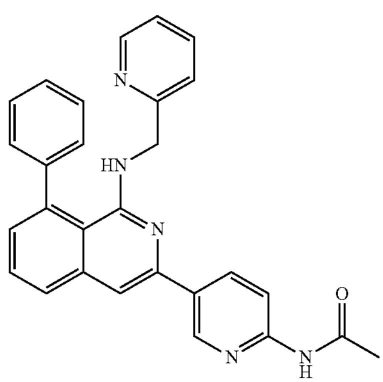 [SMILES: CC(=O)Nc1ccc(-c2cc3cccc(-c4ccccc4)c3c(NCc3ccccn3)n2)cn1] | N-(5-(8-phenyl-1-(pyridin-2-ylmethylamino)isoquinolin-3-yl)pyridin-2-yl)acetamide | ¹H NMR (400 MHz, DMSO-d₆) δ ppm: 2.13 (s, 3 H), 4.62 (d, J = 4.4 Hz, 2 H), 6.04 (t, J = 4.4 Hz, 2 H), 7.17-7.30 (m, 3 H), 7.49-7.53 (m, 4 H), 7.64-7.70 (m, 2 H), 7.73 (s, 1 H), 7.85 (dd, J = 1.2, J = 8.0 Hz, 1 H), 8.17 (d, J = 8.8 Hz, 1 H), 8.29 (d, J = 4.8 Hz, 1 H), 8.46 (dd, J = 2.4, J = 8.4 Hz, 1 H), 9.04 (d, J = 2.4 Hz, 1 H), 10.59 (s, 1 H). | 1.86 B-47 446.2 |
| 65 | 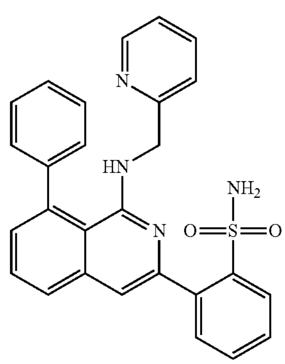 [SMILES: NS(=O)(=O)c1ccccc1-c1cc2cccc(-c3ccccc3)c2c(NCc2ccccn2)n1] | 2-(8-phenyl-1-(pyridin-2-ylmethylamino)isoquinolin-3-yl)benzenesulfonamide | ¹H NMR (400 MHz, DMSO-d₆) δ ppm: 4.47 (d, J = 4.4 Hz, 2 H), 6.19 (t, J = 4.4 Hz, 1 H), 7.11 (d, J = 7.6 Hz, 1 H), 7.21 (dt, J = 1.2, J = 6.0 Hz, 1 H), 7.26 (s, 1 H), 7.29 (dd, J = 1.2, J = 7.2 Hz, 1 H), 7.44-7.50 (m, 7 H), 7.59-7.72 (m, 5 H), 7.84 (dd, J = 1.2, J = 8.4 Hz, 1 H), 8.03 (dd, J = 1.2, J = 8.0 Hz, 1 H), 8.23 (m, 1 H). | 1.97 B-47 467.2 |

TABLE 1-continued

| Example No. | Structure | Name | ¹H NMR | LC/MS Rt (min) Method M + H |
|---|---|---|---|---|
| 66 | 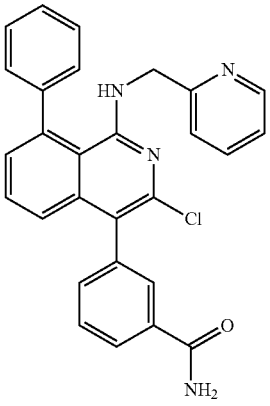 [SMILES: NC(=O)c1cccc(-c2c(Cl)nc(NCc3ccccn3)c3c(-c4ccccc4)cccc23)c1] | 3-(3-chloro-8-phenyl-1-(pyridin-2-ylmethylamino)isoquinolin-4-yl)benzamide | ¹H NMR (400 MHz, DMSO-d$_6$) δ ppm: 4.53 (d, J = 4.0 Hz, 2 H), 6.50 (t, J = 4.0 Hz, 1 H), 7.19-7.29 (m, 4 H), 7.41-7.59 (m, 7 H), 7.61-7.88 (m, 3 H), 7.98 (s, 1 H), 7.99-8.02 (m, 2 H), 8.21-8.23 (m, 1 H) | 2.29 B-17 465.2 |
| 67 | 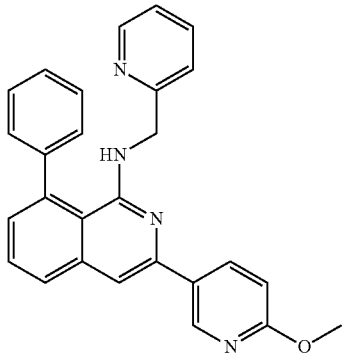 [SMILES: COc1ccc(-c2cc3cccc(-c4ccccc4)c3c(NCc3ccccn3)n2)cn1] | 3-(6-methoxypyridin-3-yl)-8-phenyl-N-(pyridin-2-ylmethyl)isoquinolin-1-amine | ¹H NMR (400 MHz, DMSO-d$_6$) δ ppm: 3.92 (s, 3 H), 4.62 (d, J = 4.4 Hz, 2 H), 6.08 (t, J = 4.4 Hz, 1 H), 6.91 (d, J = 8.4 Hz, 1 H), 7.18-7.24 (m, 3 H), 7.46-7.52 (m, 5 H), 7.63-7.69 (m, 3 H), 7.83-7.85 (m, 1 H), 8.20-8.26 (m, 1 H), 8.42 (d, J = 8.4 Hz, 1 H), 8.99 (s, 1 H) | 2.60 B-17 419.2 |
| 68 | 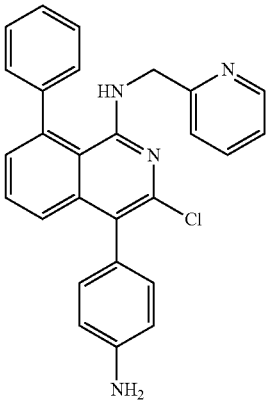 [SMILES: Nc1ccc(-c2c(Cl)nc(NCc3ccccn3)c3c(-c4ccccc4)cccc23)cc1] | 4-(4-aminophenyl)-3-chloro-8-phenyl-N-(pyridin-2-ylmethyl)isoquinolin-1-amine | ¹H NMR (400 MHz, DMSO-d$_6$) δ ppm: 4.51 (d, J = 4.0 Hz, 2 H), 5.22 (s, 2 H), 6.34 (t, J = 4.0 Hz, 1 H), 6.71 (dd, J = 8.8 Hz, J = 2.4 Hz, 2 H), 6.96 (dd, J = 8.4 Hz, J = 1.6 Hz, 2 H), 7.20-7.27 (m, 3 H), 7.40 (dd, J = 8.4 Hz, J = 1.2 Hz, 1 H), 7.45-7.52 (m, 5 H), 7.58 (dd, J = 8.4 Hz, J = 7.2 Hz, 1 H), 7.69 (dd, J = 9.6 Hz, J = 2.0 Hz, 1 H), 8.21-8.23 (m, 1 H). | 1.79 B-26 437.2 |

TABLE 1-continued

| Example No. | Structure | Name | ¹H NMR | LC/MS Rt (min) Method M + H |
|---|---|---|---|---|
| 69 | 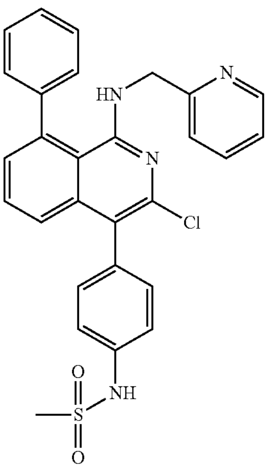 [SMILES: CS(=O)(=O)Nc1ccc(-c2c(Cl)nc(NCc3ccccn3)c3c(-c4ccccc4)cccc23)cc1] | N-(4-(3-chloro-8-phenyl-1-(pyridin-2-ylmethylamino)isoquinolin-4-yl)phenyl)methanesulfonamide | ¹H NMR (400 MHz, DMSO-d₆) δ ppm: 3.12 (s, 3 H), 4.52 (d, J = 4.0 Hz, 2 H), 6.45 (t, J = 4.4 Hz, 1 H), 7.16-7.38 (m, 8 H), 7.47-7.62 (m, 6 H), 7.70 (dt, J = 7.6 Hz, J = 2.0 Hz, 1 H), 8.22 (d, J = 4.0 Hz, 1 H), 9.94 (s, 1 H). | 2.06 B-26 515.0 |
| 70 | 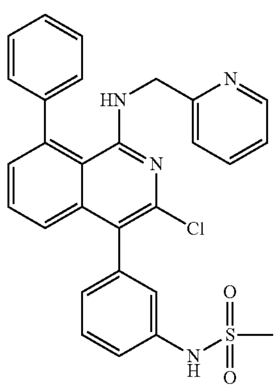 [SMILES: CS(=O)(=O)Nc1cccc(-c2c(Cl)nc(NCc3ccccn3)c3c(-c4ccccc4)cccc23)c1] | N-(3-(3-chloro-8-phenyl-1-(pyridin-2-ylmethylamino)isoquinolin-4-yl)phenyl)methanesulfonamide | ¹H NMR (400 MHz, DMSO-d₆) δ ppm: 3.06 (s, 3 H), 4.56 (d, J = 4.0 Hz, 2 H), 6.37 (t, J = 4.0 Hz, 1 H), 7.01-7.17 (m, 2 H), 7.26-7.49 (m, 5 H), 7.50-7.53 (m, 6 H), 7.61-7.65 (m, 1 H), 7.82-7.84 (m, 1 H), 8.32 (d, J = 4.4 Hz, 1 H), 9.96 (s, 1 H) | 1.92 B-26 467.2 |
| 71 | 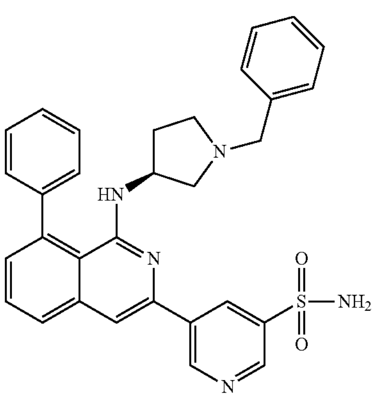 [SMILES: NS(=O)(=O)c1cncc(-c2cc3cccc(-c4ccccc4)c3c(N[C@H]3CCN(Cc4ccccc4)C3)n2)c1] | (S)-5-(1-(1-benzylpyrrolidin-3-ylamino)-8-phenylisoquinolin-3-yl)pyridine-3-sulfonamide | ¹H NMR (400 MHz, DMSO-d₆) δ ppm: 1.03 (m, 1 H), 1.21 (m, 2 H), 2.23 (m, 1 H), 2.32 (m, 2 H), 3.45 (t, J = 1.8 Hz, 2 H), 4.45 (m, 1 H), 5.01 (m, 1 H), 7.24-7.26 (m, 2 H), 7.31-7.33 (m, 3 H), 7.33-7.48 (m, 5 H), 7.57-7.80 (m, 3 H), 7.86-7.89 (m, 2 H), 8.82 (d, J = 2.0 Hz, 1 H), 8.96 (d, J = 2.0 Hz, 1 H). 9.08 (d, J = 2.0 Hz, 1 H), 9.51 (s, 1 H) | 2.93 B-12 536.2 |

TABLE 1-continued

| Example No. | Structure | Name | ¹H NMR | LC/MS Rt (min) Method M + H |
|---|---|---|---|---|
| 72 | 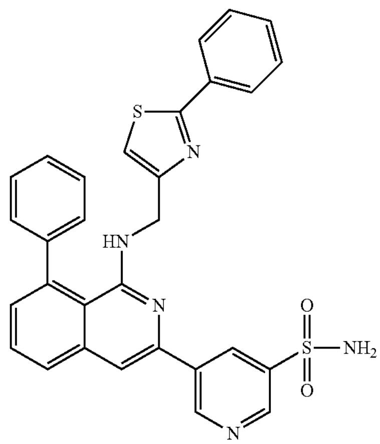 [SMILES: NS(=O)(=O)c1cncc(-c2cc3cccc(-c4ccccc4)c3c(NCc3csc(-c4ccccc4)n3)n2)c1] | 5-(8-phenyl-1-((2-phenylthiazol-4-yl)methylamino)isoquinolin-3-yl)pyridine-3-sulfonamide | ¹H NMR (400 MHz, DMSO-d$_6$) δ ppm: 4.68 (d, J = 4.8 Hz, 2 H), 5.35 (t, J = 4.8 Hz, 1 H), 6.35 (br s, 1 H), 7, 7.17-7.19 (m, 1 H), 7.25-7.31 (m, 4 H), 7.33-7.36 (m, 2 H), 7.64-7.69 (m, 1 H) 7.72 (m, 3 H), 7.90-7.95 (m, 4 H), 8.82 (d, J = 2.0 Hz, 1 H), 8.92 (d, J = 2.0 Hz, 1 H). 9.08 (d, J = 2.0 Hz, 1 H), 9.45 (s, 1 H) | 2.90 B-12 550.2 |
| 73 | 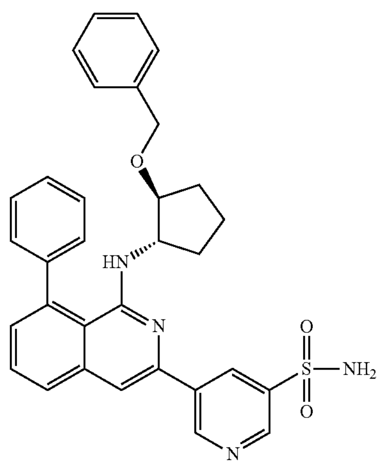 [SMILES: NS(=O)(=O)c1cncc(-c2cc3cccc(-c4ccccc4)c3c(N[C@H]3CCC[C@@H]3OCc3ccccc3)n2)c1] | 5-(1-(((1S,2S)-2-(benzyloxy)cyclopentylamino)-8-phenylisoquinolin-3-yl)pyridine-3-sulfonamide | ¹H NMR (400 MHz, DMSO-d$_6$) δ ppm: 0.95 (m, 1 H), 1.13 (m, 1 H), 1.40-1.62 (m, 3 H), 3.42 (t, J = 1.8 Hz, 1 H), 4.44-4.45 (m, 4 H), 4.82 (d, J = 6.4 Hz, 1 H), 7.15-7.29 (m, 6 H), 7.49-7.62 (m, 6 H), 7.71-7.75 (m, 3 H), 7.85 (s, 1 H), 7.93 (d, J = 1.2 Hz, 1 H), 8.86 (d, J = 2.0 Hz, 1 H). 9.0 (d, J = 2.0 Hz, 1 H), 9.56 (s, 1 H) | 3.07 B-12 551.2 |
| 74 | 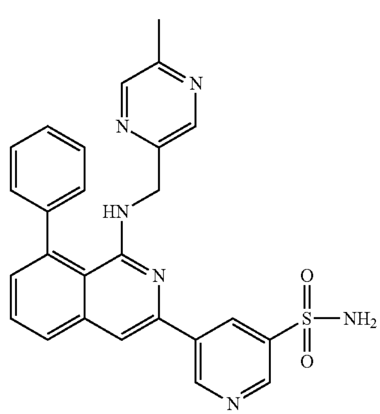 [SMILES: Cc1cnc(CNc2nc(-c3cncc(S(N)(=O)=O)c3)cc3cccc(-c4ccccc4)c23)cn1] | 5-(1-((5-methylpyrazin-2-yl)methylamino)-8-phenylisoquinolin-3-yl)pyridine-3-sulfonamide | ¹H NMR (400 MHz, DMSO-d$_6$) δ ppm: 2.45 (s, 3 H), 4.66 (d, J = 4.4 Hz, 2 H), 5.88 (t, J = 4.8 Hz, 1 H) 7.31 (d, J = 2.0 Hz, 1 H), 7.33-7.52 (m, 5 H), 7.68-7.74 (m, 3 H), 7.93-7.96 (m, 2 H), 8.28 (s, 1 H), 8.40 (s, 1 H), 8.86 (d, J = 2.0 Hz, 1 H). 9.02 (d, J = 2.0 Hz, 1 H), 9.57 (s, 1 H) | 2.18 B-12 483.2 |

TABLE 1-continued

| Example No. | Name | ¹H NMR | LC/MS Rt (min) Method M + H |
|---|---|---|---|
| 75 | 5-(1-(benzylamino)-3-chloro-8-phenylisoquinolin-4-yl)pyridine-3-sulfonamide | ¹H NMR (400 MHz, DMSO-$d_6$) δ ppm: 4.40 (d, J = 4.0 Hz, 2 H), 5.43 (t, J = 4.8 Hz, 1 H), 6.90 (br s, 2 H), 7.02 (dd, J = 7.6 Hz, J = 7.2 Hz, 1 H), 7.17-7.19 (m, 1 H), 7.23-7.31 (m, 4 H), 7.33-7.36 (m, 1 H), 7.42-7.47 (m, 5 H), 7.64-7.66 (m, 1 H) 8.21 (d, J = 4 Hz, 1 H), 8.81 (d, J = 2 Hz, 1 H), 9.08 (d, J = 2 Hz, 1 H). | 2.12 B-15 501.2 |
| 76 | 4-(8-phenyl-1-(pyridin-2-ylmethylamino)isoquinolin-4-yl)benzenesulfonamide | ¹H NMR (400 MHz, DMSO-$d_6$) δ ppm: 4.54 (d, J = 4.0 Hz, 2 H), 6.58 (t, J = 4.0 Hz, 1 H), 7.17 (dd, J = 8.4 Hz, J = 1.2 Hz, 1 H), 7.23 (dd, J = 7.2 Hz, J = 5.6 Hz, 1 H), 7.27-7.31 (m, 2 H), 7.47-7.64 (m, 10 H), 7.71 (dt, J = 7.6 Hz, J = 1.6 Hz, 1 H), 8.02-8.04 (m, 3 H), 8.21 (dd, J = 4.4 Hz, J = 0.8 Hz, 1 H). | 1.03 B-41 467.3 |
| 77 | 4-(6-aminopyridin-3-yl)-3-chloro-8-phenyl-N-(pyridin-2-ylmethyl)isoquinolin-1-amine | ¹H NMR (400 MHz, DMSO-$d_6$) δ ppm: 4.51 (d, J = 3.6 Hz, 2 H), 6.08 (s, 2 H), 6.43 (t, J = 4.0 Hz, 1 H), 6.61 (d, J = 8.4 Hz, 1 H), 7.20-7.27 (m, 3 H), 7.35 (dd, J = 2.4 Hz, J = 8.4 Hz, 1 H), 7.38 (dd, J = 1.2 Hz, J = 8.4 Hz, 1 H), 7.48-7.52 (m, 5 H), 7.62 (dd, J = 7.2 Hz, J = 8.4 Hz, 1 H), 7.70 (dt, J = 1.6 Hz, J = 7.6 Hz, 1 H), 7.84-7.85 (d, J = 2.4 Hz, 1 H), 8.22 (d, J = 4.4 Hz, 1 H) | 2.01 B-15 438.2 |

TABLE 1-continued

| Example No. | Structure | Name | ¹H NMR | LC/MS Rt (min) Method M + H |
|---|---|---|---|---|
| 78 | 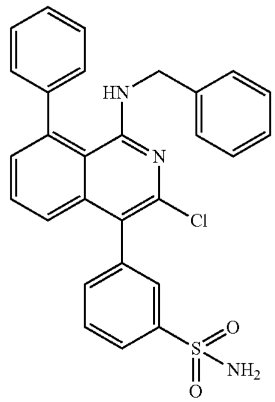 [SMILES: NS(=O)(=O)c1cccc(-c2c(Cl)nc(NCc3ccccc3)c3c(-c4ccccc4)cccc23)c1] | 3-(1-(benzylamino)-3-chloro-8-phenylisoquinolin-4-yl)benzenesulfonamide | ¹H NMR (400 MHz, DMSO-d$_6$) δ ppm: 4.54 (d, J = 4.0 Hz, 1 H), 6.55 (dd, J = 4.4 Hz, J = 4.0 Hz, 1 H), 7.18 (dd, J = 8.4 Hz, J = 0.8 Hz, 1 H), 7.22-7.25 (m, 1 H), 7.28-7.31 (m, 2 H), 7.49-7.55 (m, 7 H), 7.58-7.65 (m, 5 H), 7.71 (dd, J = 7.6 Hz, J = 1.6 Hz, 1 H), 7.99-8.01 (m, 2 H), 8.22 (d, J = 4.0 Hz, 1 H) | 2.46 B-17 500.2 |
| 79 | 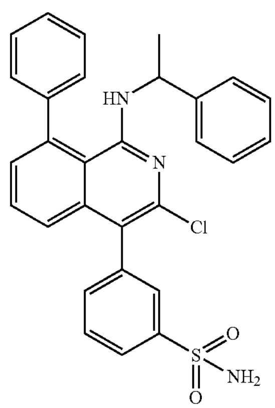 [SMILES: CC(Nc1nc(Cl)c(-c2cccc(S(N)(=O)=O)c2)c2cccc(-c3ccccc3)c12)c1ccccc1] | 3-(3-chloro-8-phenyl-1-(1-phenylethylamino)isoquinolin-4-yl)benzenesulfonamide | ¹H NMR (400 MHz, DMSO-d$_6$) δ ppm: 1.06 (m, 3 H), 5.03 (t, J = 4.0 Hz 1 H), 5.35 (d, J = 6.4 Hz, 1 H), 7.03 (m, 2 H), 7.14-7.33 (m, 3 H), 7.28-7.31 (m, 2 H), 7.42-7.46 (m, 2 H), 7.54-7.70 (m, 7 H), 7.71 (m, 2 H), 7.90-7.93 (m, 1 H) | 2.44 B-18 512.0 |
| 80 | 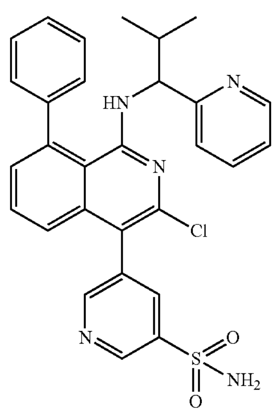 [SMILES: CC(C)C(Nc1nc(Cl)c(-c2cncc(S(N)(=O)=O)c2)c2cccc(-c3ccccc3)c12)c1ccccn1] | 5-(3-chloro-1-(2-methyl-1-(pyridin-2-yl)propylamino)-8-phenylisoquinolin-4-yl)pyridine-3-sulfonamide | ¹H NMR (400 MHz, DMSO-d$_6$) δ ppm: 0.50 (m, 3 H), 0.61 (m, 3 H), 1.95 (m, 1 H), 5.09 (t, J = 5.6 Hz, 1 H), 6.22 (t, J = 6.8 Hz, 1 H), 7.12-7.29 (m, 2 H), 7.32 (d, J = 4.2 Hz, 1 H), 7.57-7.70 (m, 9 H), 8.11 (d, J = 2.0 Hz, 1 H), 8.16 (d, J = 2.0 Hz, 1 H), 8.37 (t, J = 2 Hz, 1 H), 8.80 (dd, J = 2 Hz, J = 2 Hz, 1 H), 9.06 (s, 1 H). | 2.10 B-15 544.2 |

TABLE 1-continued

| Example No. | Structure | Name | ¹H NMR | LC/MS Rt (min) Method M + H |
|---|---|---|---|---|
| 81 | 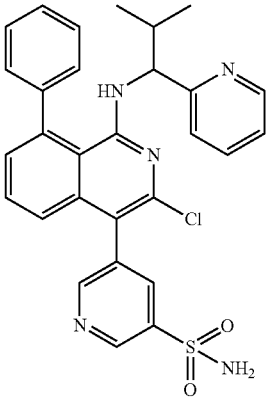 [SMILES: CC(C)C(Nc1nc(Cl)c(-c2cncc(S(N)(=O)=O)c2)c2cccc(-c3ccccc3)c12)c1ccccn1] | 5-(3-chloro-1-(2-methyl-1-(pyridin-2-yl)propylamino)-8-phenylisoquinolin-4-yl)pyridine-3-sulfonamide | ¹H NMR (400 MHz, DMSO-d₆) δ ppm: 0.50 (m, 3 H), 0.61 (m, 3 H), 1.95 (m, 1 H), 5.09 (t, J = 5.6 Hz, 1 H), 6.22 (t, J = 6.8 Hz, 1 H), 7.12-7.29 (m, 2 H), 7.32 (d, J = 4.2 Hz, 1 H), 7.57-7.70 (m, 9 H), 8.11 (d, J = 2.0 Hz, 1 H), 8.16 (d, J = 2.0 Hz, 1 H), 8.37 (t, J = 2 Hz, 1 H), 8.80 (dd, J = 2 Hz, J = 2 Hz, 1 H), 9.06 (s, 1 H). | 2.16 B-15 544.0 |
| 82 | 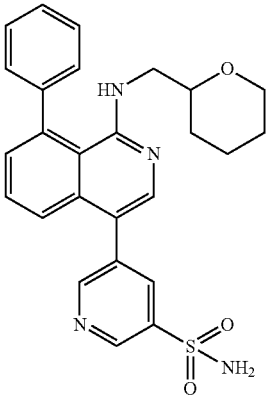 [SMILES: NS(=O)(=O)c1cncc(-c2cnc(NCC3CCCCO3)c3c(-c4ccccc4)cccc23)c1] | 5-(8-phenyl-1-((tetrahydro-2H-pyran-2-yl)methylamino)isoquinolin-4-yl)pyridine-3-sulfonamide | ¹H NMR (400 MHz, DMSO-d₆) δ ppm: 1.03-1.05 (m, 1 H), 1.32-1.40 (m, 4 H), 1.67-1.70 (m, 1 H), 3.01-3.08 (m, 3 H), 3.41-3.45 (m, 1 H), 3.62-3.65 (m, 1 H), 5.27 (t, J = 2.0 Hz, 1 H), 7.30-7.32 (m, 1 H), 7.44 (s, 2 H), 7.56-7.70 (m, 7 H), 7.92 (s, 1 H), 8.25 (t, J = 2.4 Hz, 1 H), 8.89 (d, J = 2 Hz, 1 H), 9.02 (d, J = 2 Hz, 1 H) | 1.92 B-15 475.2 |
| 83 | 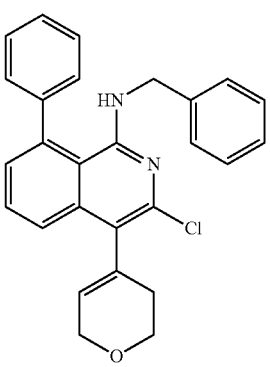 [SMILES: Clc1nc(NCc2ccccc2)c2c(-c3ccccc3)cccc2c1C1=CCOCC1] | N-benzyl-3-chloro-4-(3,6-dihydro-2H-pyran-4-yl)-8-phenylisoquinolin-1-amine | ¹H NMR (400 MHz, DMSO-d₆) δ ppm: 2.17-2.39 (m, 2 H), 3.87-3.99 (m, 2 H), 4.24 (m, 4 H), 5.18 (t, J = 4.8 Hz, 1 H), 5.79 (br s, 1 H), 6.96 (dd, J = 4.0 Hz, J = 4.8 Hz, 2 H), 7.21-7.21 (m, 4 H), 7.37-7.45 (m, 5 H), 7.68-7.72 (m, 2 H) | 2.62 B-21 427.2 |

TABLE 1-continued

| Example No. | Structure | Name | ¹H NMR | LC/MS Rt (min) Method M + H |
|---|---|---|---|---|
| 84 | 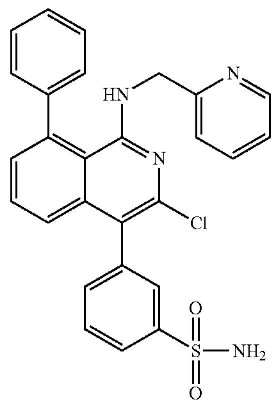 [SMILES: NS(=O)(=O)c1cccc(-c2c(Cl)nc(NCc3ccccn3)c3c(-c4ccccc4)cccc23)c1] | 3-(3-chloro-8-phenyl-1-(pyridin-2-ylmethylamino)isoquinolin-4-yl)benzenesulfonamide | ¹H NMR (400 MHz, DMSO-$d_6$) δ ppm: 4.54 (d, J = 3.6, 2 H), 6.55 (t, J = 4.4 Hz, J = 4.0 Hz, 1 H), 7.17 (m, 1 H), 7.26 (m, 1 H), 7.27-7.30 (m, 2 H), 7.48-7.65 (m, 11 H), 7.98-8.01 (m, 2 H), 8.22 (d, J = 4.4 Hz, 1 H). | 2.02 B-13 501.2 |
| 85 | 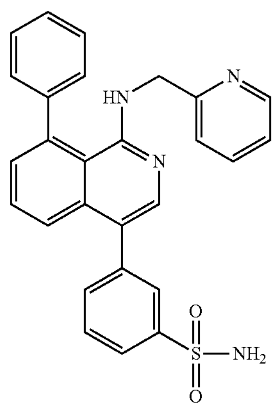 [SMILES: NS(=O)(=O)c1cccc(-c2cnc(NCc3ccccn3)c3c(-c4ccccc4)cccc23)c1] | 3-(8-phenyl-1-(pyridin-2-ylmethylamino)isoquinolin-4-yl)benzenesulfonamide | ¹H NMR (400 MHz, DMSO-$d_6$) δ ppm: 4.54 (d, J = 3.6, 2 H), 6.55 (t, J = 4.4 Hz, J = 4.0 Hz, 1 H), 7.14 (m, 1 H), 7.22 (m, 2 H), 7.28-7.32 (m, 2 H), 7.49-7.63 (m, 11 H), 7.99-8.03 (m, 2 H), 8.24 (d, J = 4.4 Hz, 1 H). | 1.01 B-41 467.3 |

It is noted that the proceeding examples, while illustrative of the present invention, are not in sequential order and some example numbers may be missing.

Utility

In general, compounds of the present invention, such as particular compounds disclosed in the preceding examples, have been shown to inhibit the $K_v1$ subfamily of voltage-gated $K^+$ channels (for example, by displaying % inhibition values≥29%, preferably ≥30%, more preferably ≥40%, even more preferably ≥50%, at 0.3 micromolar concentration in an assay such as those set forth below). By displaying activity as inhibitors of the $K_v1$ subfamily of voltage-gated $K^+$ channels, compounds of the present invention are expected to be useful in the treatment of human diseases associated with the $K_v1$ subfamily of voltage-gated $K^+$ channels.

Assays to determine the degree of activity of a compound as an $I_{Kur}$ inhibitor are well known in the art and are described in references such as *J. Gen. Physiol.*, 101(4): 513-543 (April 1993), and *Br. J. Pharmacol.*, 115(2):267-274 (May 1995).

Assays to determine the degree of activity of a compound as an inhibitor of other members of the $K_v1$ subfamily are also well known in the art. For example, inhibition of $K_v1.1$, $K_v1.2$ and $K_v1.3$ can be measured using procedures described by Grissmer, S. et al., *Mol. Pharmacol.*, 45(6): 1227-1234 (June 1994); inhibition of $K_v1.4$ can be measured using procedures described by Petersen, K. R. et al., *Pflugers Arch.*, 437(3):381-392 (February 1999); inhibition of $K_v1.6$ can be measured using procedures described by Bowlby, M. R. et al., *J. Neurophysiol.* 73(6):2221-2229 (June 1995); and inhibition of $K_v1.7$ can be measured using procedures described by Kalman, K. et al., *J. Biol. Chem.*, 273(10): 5851-5857 (Mar. 6, 1998).

Examples 1-85, as shown in Table 2, were assayed for block of $I_{Kur}$ current in patch clamped mammalian L-929 cells which were injected with human $K_v$ 1.5 mRNA and stably expressed $I_{Kur}$ protein (as described in the references described below). Inhibition data at 0.3 mM concentration for the Examples are shown in Table 2.

Synders, D. J. et al., "A rapidly activating and slowly inactivating potassium channel cloned from human heart: functional analysis after stable mammalian cell culture expression", *J. Gen. Physiol.*, 101:513-543 (1993).

Zhou, Z. et al., "Block of HERG potassium channels by the antihistamine astemizole and its metabolites desmethylastemizole and norastemizole", *J. Cardiovasc. Electrophysiol.*, 10(6):836-843 (1999).

TABLE 2

| Example | KV1_5% Inh L929 @0.3 µM |
|---|---|
| 1 | 95.10 |
| 2 | 66.17 |
| 3 | 71.91 |

TABLE 2-continued

| Example | KV1_5% Inh L929 @0.3 μM |
|---|---|
| 4 | 88.70 |
| 5 | 75.60 |
| 6 | 92.22 |
| 7 | 34.80 |
| 8 | 61.44 |
| 9 | 81.32 |
| 9 | 50.45 |
| 10 | 98.98 |
| 11 | 98.91 |
| 12 | 52.33 |
| 13 | 97.68 |
| 14 | 93.24 |
| 15 | 96.25 |
| 16 | 88.63 |
| 17 | 93.45 |
| 18 | 97.21 |
| 18 isomer 1 | |
| 18 isomer 2 | 95.35 |
| 19 | 89.96 |
| 20 | 64.51 |
| 21 | 50.62 |
| 22 | 94.00 |
| 23 | 80.21 |
| 24 | 41.45 |
| 25 | 53.21 |
| 26 | 98.80 |
| 27 | 93.60 |
| 28 | 76.09 |
| 29 | 88.39 |
| 30 | 51.28 |
| 31 | 15.20 |
| 32 | 70.65 |
| 33 | 73.42 |
| 34 | 93.53 |
| 35 | 36.18 |
| 36 | 94.56 |
| 37 | 34.16 |
| 38 | 90.75 |
| 39 | 66.82 |
| 40 | 92.32 |
| 41 | 54.06 |
| 42 | 60.31 |
| 43 | 16.31 |
| 44 | 18.60 |
| 45 | 78.50 |
| 46 | 98.37 |
| 47 | 98.13 |
| 48 | 98.63 |
| 49 | 52.22 |
| 50 | 54.13 |
| 51 | 86.31 |
| 52 | 55.80 |
| 53 | 40.11 |
| 54 | 82.36 |
| 55 | 97.61 |
| 56 | 89.68 |
| 57 | 98.61 |
| 58 | 22.83 |
| 60 | 96.20 |
| 61 | 95.06 |
| 62 | 95.61 |
| 63 | 53.21 |
| 64 | 57.49 |
| 65 | 50.46 |
| 66 | 99.33 |
| 67 | 96.86 |
| 68 | 98.33 |
| 69 | 98.44 |
| 70 | 95.69 |
| 71 | 67.73 |
| 72 | 16.09 |
| 73 | 56.30 |
| 74 | 79.48 |
| 75 | 97.35 |
| 76 | 97.15 |
| 77 | 99.05 |
| 78 | 91.00 |
| 79 | 67.47 |
| 80 | 92.54 |
| 81 | 96.22 |
| 81 isomer 1 | 94.54 |
| 81 isomer 2 | |
| 82 isomer 1 | 86.94 |
| 82 isomer 2 | 86.43 |
| 82 | 84.97 |
| 83 | 19.28 |
| 84 | 98.43 |
| 85 | 99.03 |

Compounds within the scope of the present invention inhibit the $K_v1$ subfamily of voltage-gated $K^+$ channels, and as such are believed to be useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents, including maintaining normal sinus rhythm; angina pectoris including relief of Prinzmetal's symptoms, vasospastic symptoms and variant symptoms; gastrointestinal disorders including reflux esophagitis, functional dyspepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell proliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated $K^+$ channels compounds of the present invention are believed to be useful to treat a variety of further disorders including resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are suspected antiarrhythmic agents which are useful in the prevention and treatment (including partial alleviation or cure) of arrhythmias. As inhibitors of $K_v1.5$, compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio can also be greater than 4:1, even greater than 10:1. In addition, the ratio may be such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker can provide useful treatment for disorders such as: reflux esophagitis, functional dyspepsia, constipation, asthma, and diabetes. Additionally, $K_v1.5$ is known to be expressed in the anterior pituitary. Thus, administration of an $I_{Kur}$ blocker can stimulate growth hormone secretion. $I_{Kur}$ inhibitors can additionally be useful in cell proliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula (I), (Ia), or compounds exemplified in the examples, Other therapeutic agents such as those described below may be employed with the inventive compounds in the present methods. In the methods of the present invention, such other therapeutic agent(s) may be administered prior to, simultaneously with or following the administration of the compound(s) of the present invention.

Dosage and Formulation

The present invention also provides pharmaceutical compositions comprising at least one of the compounds of the formula (I), (Ia), or one of the examples, or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula (I), (Ia), or one of the examples, may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula (I), or one of the examples, are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula (I), (Ia), or one of the examples, may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (AVICEL®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, naproxen, CELEBREX®, VIOXX® and NSAIDs; anti-platelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; antithrombotic/thrombolytic agents such as tissue plasminogen activator (tPA), recombinant tPA, tenecteplase (TNK), lanoteplase (nPA), factor VIIa inhibitors, factor Xa inhibitors (such as apixaban), XIa inhibitors, thrombin inhibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., QUESTRAN®); antiproliferative agents such as cyclosporin A, TAXOL®, FK 506, and adriamycin; antitumor agents such as TAXOL®, adriamycin, epothilones, cisplatin and carboplatin; anti-diabetic agents such as biguanides (e.g., metformin), glucosidase inhibitors (e.g., acarbose), insulins, meglitinides (e.g., repaglinide), sulfonylureas (e.g., glimepiride, glyburide and glipizide), biguanide/glyburide combinations (i.e., GLUCOVANCE®), thiozolidinediones (e.g., troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g., cilostazol), and PDE V inhibitors (e.g., sildenafil); protein tyrosine kinase inhibitors; steroidal anti-inflammatory agents such as prednisone, and dexamethasone; and other anti-inflammatory agents such as ENBREL®. The combinations can be co-formulated or in the form of kits packaged to provide appropriate dosages for co-administration.

The above other therapeutic agents, when employed in combination with the compounds of the present invention, may be used, for example, in those amounts indicated in the *Physicians' Desk Reference* (PDR) or as otherwise determined by one of ordinary skill in the art.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon particular embodiments, it will be obvious to those of ordinary skill in the art that variations in the particular compounds and methods may be used and that it is intended that the invention may be practiced otherwise than as specifically described herein. Accordingly, this invention includes all modifications encompassed within the spirit and scope of the invention as defined by the claims that follow.

What is claimed is:
1. A compound of formula (I)

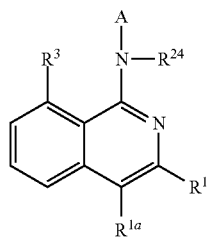

or salt thereof, wherein:
A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

one of R$^1$ or R$^{1a}$ is C$_{1-10}$ alkyl substituted with 1-2 —OH, haloC$_{1-10}$ alkyl, C$_{2-12}$ alkenyl or C$_{3-10}$ cycloalkyl, wherein the cycloalkyl may be substituted with 0-2 R$^{13}$; or

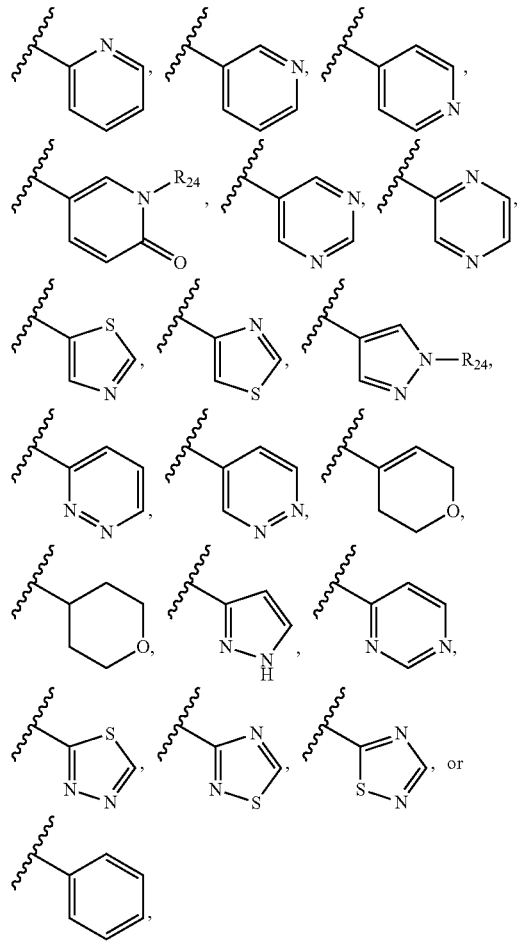

any of which may be substituted with 0-2 R$^{13}$;
the other of R$^1$ or R$^{1a}$ is hydrogen, C$_{1-3}$alkyl, —C(O)—NH$_2$, —S—CH$_3$, cyano, or halo;
R$^2$ is phenyl, cyclopentyl, pyridinyl, pyrazinyl, pyrimidinyl, piperidinyl, pyridinone, pyrrolidinyl, tetrahydropyranyl, or thiazolyl, any of which are substituted with 0-2 R$^{2a}$;
R$^{2a}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$-alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NCOR$^{14}$, wherein the alkyl, cycloalkyl, alkenyl, alkoxy, aryl, heteroaryl and heterocyclyl may be substituted with 0-2 R$^{14a}$, and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyranyl, or tetrahydropyran any of which may be substituted with 0-1 $R^{3a}$;

$R^{3a}$ is halo, CN, NH$_2$, —O—C$_{1-3}$alkyl, or morpholinyl;

$R^{13}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$ aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$, —NCOR$^{14}$, or OR$^{14}$, wherein the alkyl, cycloalkyl, alkenyl, alkoxy, aryl, heteroaryl and heterocyclyl may be substituted with 0-2 R$^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, C$_{1-10}$ alkyl, C$_{3-10}$ cycloalkyl, C$_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 R$^{14a}$ and the heteroaryl and heterocyclyl consist of carbon atoms and 1, 2, 3, or 4 heteroatoms independently selected from the group consisting of N, S, or O; or alternatively, two R$^{14}$'s are taken together with the atoms to which they are attached to form a cyclic ring, wherein the cyclic ring may be substituted with 0-1 R$^{14a}$ and optionally contain 1, 2, 3, or 4 heteroatoms independently selected from the group consisting of N, S, or O;

$R^{14a}$, at each occurrence, is independently selected from F, Cl, Br, I, C$_{1-10}$ alkyl, haloC$_{1-10}$alkyl, C$_{6-10}$aryl, C$_{3-10}$cycloalkyl, a 4- to 12-membered heteroaryl, a 4- to 12-membered heterocyclyl, F, Cl, Br, I, —CN, —NO$_2$, —CO$_2$R$^{26}$, —CO$_2$NR$^{24}$R$^{24}$, —OCF$_3$, —OR$^{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, —SO$_2$NR$^{24}$R$^{24}$, or C$_{6-10}$arylC$_{1-10}$alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, C$_{1-10}$alkyl, C$_{3-6}$cycloalkyl, or phenyl;

$R^{25}$, at each occurrence, is independently selected from hydrogen, C$_{1-10}$alkyl, C$_{3-6}$cycloalkyl, or phenyl;

$R^{26}$, at each occurrence, is independently selected from hydrogen, C$_{1-10}$alkyl, C$_{3-6}$cycloalkyl, or phenyl;

m is 0 to 4;

n is 0 to 4; and n–1 is 2 to 4.

2. The compound of claim 1, or salt thereof, wherein:
one of R$^1$ or R$^{1a}$ is C$_{1-10}$ alkyl substituted with 1-2 —OH, haloC$_{1-10}$ alkyl, or C$_{3-10}$ cycloalkyl, wherein the cycloalkyl may be substituted with 0-2 R$^{13}$; or

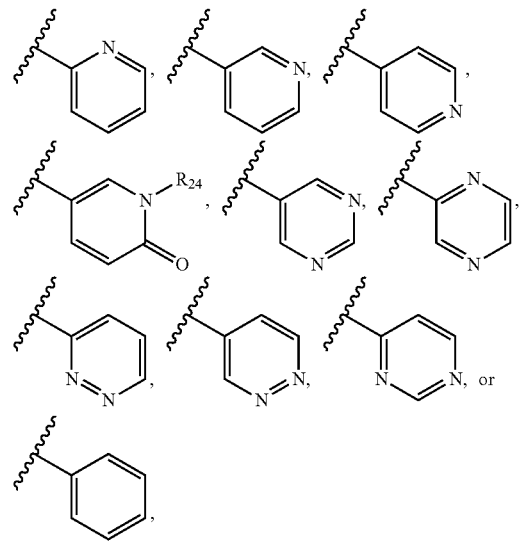

any of which may be substituted with 0-2 R$^{13}$.

3. The compound of claim 2, or salt thereof, wherein:
$R^{13}$, at each occurrence, is independently H, —OH, F, Cl, Br, I, C$_{1-6}$ alkyl, C$_{1-6}$ alkoxy, haloC$_{1-6}$ alkyl, C$_{3-6}$ cycloalkyl, phenyl, tetrazolyl, —CN, —NO$_2$, —(CH$_2$)$_m$—SO$_2$R$^{14}$, —NR$^{14}$SO$_2$R$^{14}$, —CONR$^{14}$R$^{14}$, —(CH$_2$)$_m$—SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —NR$^{14}$CO$_2$R$^{14}$, —CO$_2$R$^{14}$, or —NR$^{14}$R$^{14}$, wherein the alkyl, cycloalkyl, phenyl, and tetrazolyl may be substituted with 0-2 R$^{14a}$;

$R^{14}$, at each occurrence, is independently selected from hydrogen, C$_{1-6}$ alkyl, C$_{3-6}$ cycloalkyl, or phenyl, wherein the alkyl, cycloalkyl, and phenyl, may be substituted with 0-3 R$^{14a}$; or alternatively, two R$^{14b}$'s are taken together with the atoms to which they are attached to form a cyclic ring, wherein the cyclic ring is morpholinyl, piperidinyl, or piperazinyl, and may be substituted with 0-1 C$_{1-6}$alkyl; and $R^{14a}$, at each occurrence, is independently selected from F, Cl, Br, I, C$_{1-6}$ alkyl, haloC$_{1-6}$alkyl, phenyl, or C$_{3-6}$cycloalkyl.

4. The compound of claim 3, or salt thereof, wherein:
A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

$R^2$ is phenyl, pyridinyl, pyrazinyl, pyrimidinyl, piperidinyl, or pyridinone, any of which are substituted with 0-2 R$^{2a}$; and $R^{2a}$, at each occurrence, is independently H, —OH, F, C$_{1-6}$ alkyl, C$_{1-6}$ alkoxy, or 6-SO$_2$NR$^{14}$R$^{14}$.

5. The compound of claim 4, wherein the compound is of formula (Ia) or salt thereof,

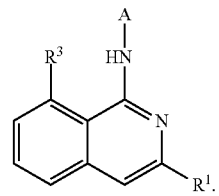

(Ia)

6. The compound of claim 5, or salt thereof wherein:
R¹ is $C_{1-10}$ alkyl substituted with 1-2 —OH, halo$C_{1-10}$ alkyl, or $C_{3-10}$ cycloalkyl, wherein the cycloalkyl may be substituted with 0-1 $R^{13}$; or
R¹ is

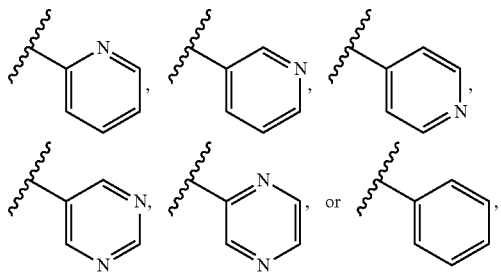

any of which may be substituted with 0-2 $R^{13}$.

7. The compound of claim 6, wherein:
$R^{13}$, at each occurrence, is independently H, $C_{1-6}$ alkyl or, tetrazolyl, —CN, —NR¹⁴SO₂R¹⁴, —CONR¹⁴R¹⁴, —SO₂NR¹⁴R¹⁴, —NR¹⁴CO₂NR¹⁴R¹⁴, —NR¹⁴CO₂NR¹⁴ᵇR¹⁴ᵇ, —NR¹⁴COR¹⁴, —CO₂R¹⁴, or —NR¹⁴R¹⁴, wherein the alkyl, and tetrazolyl may be substituted with 0-2 $R^{14a}$;
$R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or
two $R^{14b}$'s are taken together with the atoms to which they are attached to form a cyclic ring, wherein the cyclic ring is morpholinyl, and may be substituted with 0-1 $C_{1-6}$alkyl; and
$R^{14a}$, at each occurrence, is independently selected from F, Cl, Br, I, $C_{1-6}$ alkyl, halo$C_{1-6}$alkyl, phenyl, or $C_{3-6}$cycloalkyl.

8. The compound of claim 7, or salt thereof, wherein:
A is —(CH₂)—R²;
R² is phenyl,

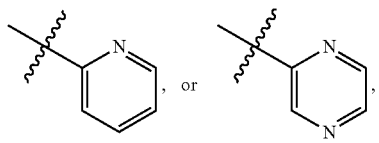 [SMILES: *c1ccccn1 ; *c1cnccn1]

any of which are substituted with 0-1 $R^{2a}$; and
$R^{2a}$, at each occurrence, is independently H, —OH, F, $C_{1-6}$ alkyl, $C_{1-6}$ alkoxy, $C_{1-6}$ haloalkoxy, or SO₂NR¹⁴R¹⁴.

9. The compound of claim 3, or salt thereof, wherein:
$R^{24}$, at each occurrence, is independently selected from hydrogen, $C_{1-6}$alkyl, $C_{3-6}$cycloalkyl, or phenyl;
$R^{25}$, at each occurrence, is independently selected from hydrogen, $C_{1-6}$alkyl, $C_{3-6}$cycloalkyl, or phenyl; and
$R_{26}$, at each occurrence, is independently selected from hydrogen, $C_{1-6}$alkyl, $C_{3-6}$cycloalkyl, or phenyl.

10. A compound, enantiomer, diastereomer, or salt thereof, selected from:
5-(8-Phenyl-1-(pyridin-2-ylmethylamino)isoquinolin-3-yl)pyridine-3-sulfonamide;
3-(5-Aminopyridin-3-yl)-8-phenyl-N-(pyridin-2-ylmethyl)isoquinolin-1-amine;
N-(5-(8-Phenyl-1-(pyridin-2-ylmethylamino)isoquinolin-3-yl)pyridin-3-yl)acetamide;
1-(5-(8-Phenyl-1-(pyridin-2-ylmethylamino)isoquinolin-3-yl)pyridin-3-yl)urea;
3-(5-Aminopyridin-3-yl)-8-phenyl-N-(pyridin-2-ylmethyl)isoquinolin-1-sulfonyl urea;
N-(3-(8-Phenyl-1-(pyridin-2-ylmethylamino)isoquinolin-3-yl)phenyl)morpholine-4-carboxamide;
2-(3-(8-Phenyl-1-(pyridin-2-ylmethylamino)isoquinolin-3-yl)phenylsulfonyl)acetamide;
5-(4-Methyl-8-phenyl-1-(pyridin-2-ylmethylamino)isoquinolin-3-yl)pyridine-3-sulfonamide;
5-(8-Phenyl-1-((pyridin-2-ylmethyl)amino)isoquinolin-3-yl)nicotinamide;
5-(3-Chloro-8-phenyl-1-(pyridin-2-ylmethylamino)isoquinolin-4-yl)pyridine-3-sulfonamide;
5-(8-Phenyl-1-(pyridin-2-ylmethylamino)isoquinolin-4-yl)pyridine-3-sulfonamide;
5-(3-Chloro-8-phenyl-1-(pyridin-2-ylmethylamino)isoquinolin-4-yl)nicotinic acid;
N1-(3-(3-Chloro-8-phenyl-1-(pyridin-2-ylmethylamino)isoquinolin-4-yl)phenyl)malonamide;
5-(1-(Benzylamino)-3-methyl-8-phenylisoquinolin-4-yl)pyridine-3-sulfonamide;
5-(1-(Benzylamino)-8-phenylisoquinolin-4-yl)pyridine-3-sulfonamide;
5-(1-(Benzylamino)-3-cyano-8-phenylisoquinolin-4-yl)pyridine-3-sulfonamide;
1-(Benzylamino)-8-phenyl-4-(5-sulfamoylpyridin-3-yl)isoquinoline-3-carboxamide;
5-(3-Chloro-8-phenyl-1-(1-phenylethylamino)isoquinolin-4-yl)pyridine-3-sulfonamide;
4-(5-(2H-Tetrazol-5-yl)pyridin-3-yl)-N-benzyl-8-phenylisoquinolin-1-amine;
3-(3,5-dimethyl-1H-pyrazol-4-yl)-8-phenyl-N-(pyridin-2-ylmethyl)isoquinolin-1-amine;
5-(8-(4-fluorophenyl)-1-(pyridin-2-ylmethylamino)isoquinolin-3-yl)pyridine-3-sulfonamide;
5-(1-((3-fluoropyridin-2-yl)methylamino)-8-phenylisoquinolin-3-yl)pyridine-3-sulfonamide;
8-phenyl-3-(1H-pyrazol-3-yl)-N-(pyridin-2-ylmethyl)isoquinolin-1-amine;
5-(1-(isobutylamino)-8-phenylisoquinolin-3-yl)pyridine-3-sulfonamide;
5-(1-(isopentylamino)-8-phenylisoquinolin-3-yl)pyridine-3-sulfonamide;
5-(3-chloro-8-phenyl-1-(1-(pyridin-2-yl)ethylamino) isoquinolin-4-yl)pyridine-3-sulfonamide;
5-(3-chloro-1-(2,6-difluorobenzylamino)-8-phenylisoquinolin-4-yl)pyridine-3-sulfonamide;
N-benzyl-4-(3,6-dihydro-2H-pyran-4-yl)-8-phenylisoquinolin-1-amine;
5-(3-chloro-8-phenyl-1-((tetrahydro-2H-pyran-4-yl)methylamino)isoquinolin-4-yl)pyridine-3-sulfon amide;
N-(2-(8-phenyl-1-(pyridin-2-ylmethylamino)isoquinolin-3-yl)phenyl)acetamide;
N-(4-(8-phenyl-1-(pyridin-2-ylmethylamino)isoquinolin-3-yl)phenyl)acetamide;
N-(methylsulfonyl)-N-(5-(8-phenyl-1-(pyridin-2-ylmethylamino)isoquinolin-3-yl)pyridin-3-yl)methanesulfonamide;
4-(8-phenyl-1-(pyridin-2-ylmethylamino)isoquinolin-3-yl)benzenesulfonamide;
N-methyl-3-(8-phenyl-1-(pyridin-2-ylmethylamino)isoquinolin-3-yl)benzenesulfonamide;

N-(3-(8-phenyl-1-(pyridin-2-ylmethylamino)isoquinolin-3-yl)phenyl)methanesulfonamide;
3-(8-phenyl-1-(pyridin-2-ylmethylamino)isoquinolin-3-yl)benzenesulfonamide;
5-(1-(2-chlorobenzylamino)-8-phenylisoquinolin-3-yl) pyridine-3-sulfonamide;
1-(3-(8-phenyl-1-(pyridin-2-ylmethylamino)isoquinolin-3-yl)phenyl)urea;
3-(8-phenyl-1-(pyridin-2-ylmethylamino)isoquinolin-3-yl)benzonitrile;
4-(8-phenyl-1-(pyridin-2-ylmethylamino)isoquinolin-3-yl)benzonitrile;
3-(8-phenyl-1-(pyridin-2-ylmethylamino)isoquinolin-3-yl)benzamide;
4-(8-phenyl-1-(pyridin-2-ylmethylamino)isoquinolin-3-yl)benzamide;
5-(1-(2,3-dichlorobenzylamino)-8-phenylisoquinolin-3-yl)pyridine-3-sulfonamide;
3-(8-phenyl-1-(3-phenylpropylamino)isoquinolin-3-yl) benzenesulfonamide;
5-(1-(2-methylbenzylamino)-8-phenylisoquinolin-3-yl) pyridine-3-sulfonamide;
N-(5-(3-chloro-8-phenyl-1-(pyridin-2-ylmethylamino) isoquinolin-4-yl)pyridin-3-yl)acetamide;
N-(5-(3-chloro-8-phenyl-1-(pyridin-2-ylmethylamino) isoquinolin-4-yl)pyridin-3-yl)methanesulfonamide;
1-(5-(3-chloro-8-phenyl-1-(pyridin-2-ylmethylamino) isoquinolin-4-yl)pyridin-3-yl)urea;
3-(2-aminophenyl)-8-phenyl-N-(pyridin-2-ylmethyl)isoquinolin-1-amine;
5-(1-(2,4-difluorobenzylamino)-8-phenylisoquinolin-3-yl)pyridine-3-sulfonamide;
3-(2-aminophenyl)-8-phenyl-N-(pyridin-2-ylmethyl)isoquinolin-1-sulfonyl urea;
5-(1-(2-phenoxyethylamino)-8-phenylisoquinolin-3-yl) pyridine-3-sulfonamide;
5-(1-(3,5-dimethylbenzylamino)-8-phenylisoquinolin-3-yl)pyridine-3-sulfonamide;
5-(1-(3-methoxybenzylamino)-8-phenylisoquinolin-3-yl) pyridine-3-sulfonamide;
4-(3-chloro-8-phenyl-1-(pyridin-2-ylmethylamino)isoquinolin-4-yl)benzenesulfonamide;
4-(3-chloro-8-phenyl-1-(pyridin-2-ylmethylamino)isoquinolin-4-yl)benzonitrile;
4-(3-chloro-8-phenyl-1-(pyridin-2-ylmethylamino)isoquinolin-4-yl)benzamide;
3-(6-aminopyridin-3-yl)-8-phenyl-N-(pyridin-2-ylmethyl)isoquinolin-1-amine;
5-(1-(4-(dimethylamino) benzylamino)-8-phenylisoquinolin-3-yl)pyridine-3-sulfonamide;
N-(3-(3-chloro-8-phenyl-1-(pyridin-2-ylmethylamino) isoquinolin-4-yl)phenyl) acetamide;
3-(3-chloro-8-phenyl-1-(pyridin-2-ylmethylamino)isoquinolin-4-yl)benzonitrile;
3-chloro-4-(2-methoxypyridin-4-yl)-8-phenyl-N-(pyridin-2-ylmethyl)isoquinolin-1-amine;
N-(5-(8-phenyl-1-(pyridin-2-ylmethylamino)isoquinolin-3-yl)pyridin-2-yl) methanesulfonamide;
N-(5-(8-phenyl-1-(pyridin-2-ylmethylamino)isoquinolin-3-yl)pyridin-2-yl)acetamide;
2-(8-phenyl-1-(pyridin-2-ylmethylamino)isoquinolin-3-yl)benzenesulfonamide;
3-(3-chloro-8-phenyl-1-(pyridin-2-ylmethylamino)isoquinolin-4-yl)benzamide;
3-(6-methoxypyridin-3-yl)-8-phenyl-N-(pyridin-2-ylmethyl) isoquinolin-1-amine;
4-(4-aminophenyl)-3-chloro-8-phenyl-N-(pyridin-2-ylmethyl) isoquinolin-1-amine;
N-(4-(3-chloro-8-phenyl-1-(pyridin-2-ylmethylamino) isoquinolin-4-yl)phenyl) methanesulfonamide;
N-(3-(3-chloro-8-phenyl-1-(pyridin-2-ylmethylamino) isoquinolin-4-yl)phenyl) methanesulfonamide;
(S)-5-(1-(1-benzylpyrrolidin-3-ylamino)-8-phenylisoquinolin-3-yl)pyridine-3-sulfonamide;
5-(8-phenyl-1-(2-phenylthiazol-4-yl)methylamino)isoquinolin-3-yl)pyridine-3-sulfonamide;
5-(1-((1S,2S)-2-(benzyloxy) cyclopentylamino)-8-phenylisoquinolin-3-yl)pyridine-3-sulfonamide;
5-(1-((5-methylpyrazin-2-yl)methylamino)-8-phenylisoquinolin-3-yl)pyridine-3-sulfonamide;
5-(1-(benzylamino)-3-chloro-8-phenylisoquinolin-4-yl) pyridine-3-sulfonamide;
4-(8-phenyl-1-(pyridin-2-ylmethylamino)isoquinolin-4-yl)benzenesulfonamide;
4-(6-aminopyridin-3-yl)-3-chloro-8-phenyl-N-(pyridin-2-ylmethyl)isoquinolin-1-amine;
3-(1-(benzylamino)-3-chloro-8-phenylisoquinolin-4-yl) benzenesulfonamide;
3-(3-chloro-8-phenyl-1-(1-phenylethylamino)isoquinolin-4-yl)benzenesulfonamide;
5-(3-chloro-1-(2-methyl-1-(pyridin-2-yl)propylamino)-8-phenylisoquinolin-4-yl)pyridine-3-sulfonamide;
5-(8-phenyl-1-((tetrahydro-2H-pyran-2-yl)methylamino) isoquinolin-4-yl)pyridine-3-sulfonamide;
N-benzyl-3-chloro-4-(3,6-dihydro-2H-pyran-4-yl)-8-phenylisoquinolin-1-amine;
3-(3-chloro-8-phenyl-1-(pyridin-2-ylmethylamino)isoquinolin-4-yl)benzenesulfonamide; or
3-(8-phenyl-1-(pyridin-2-ylmethylamino)isoquinolin-4-yl)benzenesulfonamide.

11. A pharmaceutical composition comprising a therapeutically effective amount of at least one compound of claim 1.

12. The pharmaceutical composition of claim 11, further comprising at least one other therapeutic agent, wherein the other therapeutic agent is an anti-arrhythmic agent, a calcium channel blocker, an anti-platelet agent, an anti-hypertensive agent, an anti thrombotic/anti thrombolytic agent, an anti coagulant, a HMG-CoA reductase inhibitor, an anti diabetic agent, a thyroid mimetic, a mineralocorticoid receptor antagonist, or a cardiac glycoside.

13. A pharmaceutical composition comprising a therapeutically effective amount of at least one compound of claim 10.

14. The pharmaceutical composition of claim 13, further comprising at least one other therapeutic agent, wherein the other therapeutic agent is an anti-arrhythmic agent, a calcium channel blocker, an anti-platelet agent, an anti-hypertensive agent, an anti thrombotic/anti thrombolytic agent, an anti coagulant, a HMG-CoA reductase inhibitor, an anti diabetic agent, a thyroid mimetic, a mineralocorticoid receptor antagonist, or a cardiac glycoside.

15. A method of treating arrhythmia comprising administering to a patient in need thereof an effective amount of at least one compound of claim 1.

16. A method of controlling heart rate comprising administering to a patient in need thereof an effective amount of at least one compound of claim 1.

17. A method of treating arrhythmia comprising administering to a patient in need thereof an effective amount of at least one compound of claim 10.

18. A method of controlling heart rate comprising administering to a patient in need thereof an effective amount of at least one compound of claim 10.

\* \* \* \* \*

UNITED STATES PATENT AND TRADEMARK OFFICE
CERTIFICATE OF CORRECTION

PATENT NO. : 9,458,133 B2  
APPLICATION NO. : 14/771902  
DATED : October 4, 2016  
INVENTOR(S) : Heather Finlay et al.

Page 1 of 1

It is certified that error appears in the above-identified patent and that said Letters Patent is hereby corrected as shown below:

In the Claims

In Claim 1, Column 137, Line 50 (Approx.), delete "$C_{6-10}arylC_{1-10}alkyl,$" and insert -- $C_{6-10}aryl, C_{1-10}alkyl,$ --, therefor.

In Claim 10, Column 142, Line 9 (Approx.), delete "-(2-" and insert -- -((2- --, therefor.

Signed and Sealed this  
Ninth Day of June, 2020

Andrei Iancu  
*Director of the United States Patent and Trademark Office*